United States Patent
Lorenzo et al.

(10) Patent No.: US 12,214,189 B2
(45) Date of Patent: Feb. 4, 2025

(54) FOURIER ANALYSIS SPECTROSCOPY FOR MONITORING TISSUE IMPEDANCE CHANGES AND TREATMENT OUTCOME DURING ELECTROPORATION-BASED-THERAPIES

(71) Applicants: Virginia Tech Intellectual Properties, Inc., Blacksburg, VA (US); Angio Dynamics, Inc., Latham, NY (US)

(72) Inventors: Melvin F. Lorenzo, Blacksburg, VA (US); Christopher B. Arena, Burlington, NC (US); Suyashree Bhonsle, Menlo Park, CA (US); Natalie White, Christiansburg, VA (US); Lucy Epshteyn, Blacksburg, VA (US); Rafael V. Davalos, Blacksburg, VA (US)

(73) Assignees: Virginia Tech Intellectual Properties, Inc., Blacksburg, VA (US); Angio Dynamics, Inc., Latham, NY (US)

(*) Notice: Subject to any disclaimer, the term of this patent is extended or adjusted under 35 U.S.C. 154(b) by 1107 days.

(21) Appl. No.: 16/938,778

(22) Filed: Jul. 24, 2020

(65) Prior Publication Data
US 2021/0023362 A1    Jan. 28, 2021

Related U.S. Application Data

(60) Provisional application No. 62/895,652, filed on Sep. 4, 2019, provisional application No. 62/878,194, filed on Jul. 24, 2019.

(51) Int. Cl.
*A61B 18/12* (2006.01)
*A61N 1/08* (2006.01)
(Continued)

(52) U.S. Cl.
CPC ............ *A61N 1/08* (2013.01); *A61B 18/12* (2013.01); *A61N 1/327* (2013.01);
(Continued)

(58) Field of Classification Search
CPC . A61B 18/12; A61B 18/1206; A61B 18/1233; A61B 18/14; A61B 18/1402;
(Continued)

(56) References Cited

U.S. PATENT DOCUMENTS

| | | | |
|---|---|---|---|
| 1,653,819 A | 12/1927 | Northcott | |
| 3,730,238 A | 5/1973 | Butler | |

(Continued)

FOREIGN PATENT DOCUMENTS

| | | | |
|---|---|---|---|
| AU | 7656800 A | 4/2001 | |
| AU | 2002315095 A1 | 12/2002 | |

(Continued)

OTHER PUBLICATIONS

Huang, et al., Micro-Electroporation: Improving the Efficiency and Understanding of Electrical Permeabilization of Cells, Biomedical Microdevices, vol. 2, pp. 145-150, 1999.

(Continued)

*Primary Examiner* — Thomas A Giuliani
(74) *Attorney, Agent, or Firm* — New River Valley IP Law, P.C.; Michele L. Mayberry; Ashley M. Gates

(57) ABSTRACT

Electroporation-based therapies (EBTs) employ high voltage pulsed electric fields (PEFs) to permeabilize tumor tissue, resulting in changes in passive electrical properties detectable using electrical impedance spectroscopy (EIS). Currently, commercial potentiostats for EIS are limited by impedance spectrum acquisition time (~10 s); this timeframe is much larger than pulse periods used with EBTs (~1 s). Fourier Analysis SpecTroscopy (FAST) is introduced as a methodology for monitoring tissue inter-burst impedance (Continued)

(diagnostic FAST) and intra-burst impedance (therapeutic FAST) during EBTs. FAST is a rapid-capture (<<1 s) technique which enables monitoring of inter-burst and intra-burst impedance during EBTs in real-time. FAST identified a frequency which delineates thermal effects from electroporation effects in measured impedance. Significance: FAST demonstrates the potential to perform EIS, in addition to intra-burst impedance spectroscopy, using existing pulse generator topologies.

18 Claims, 44 Drawing Sheets

(51) Int. Cl.
  *A61N 1/32* (2006.01)
  *A61B 17/00* (2006.01)
  *A61B 18/00* (2006.01)
(52) U.S. Cl.
  CPC ............ *A61B 2017/00039* (2013.01); *A61B 2017/0019* (2013.01); *A61B 2018/00613* (2013.01); *A61B 2018/00708* (2013.01); *A61B 2018/00761* (2013.01); *A61B 2018/00875* (2013.01); *A61N 2001/083* (2013.01)
(58) Field of Classification Search
  CPC .......... A61B 2018/00708; A61B 2018/00898; A61B 2018/00613; A61B 2018/00761; A61B 2018/00875; A61B 2018/00684; A61B 2018/00642; A61B 2018/00702; A61B 2018/00791; A61B 2018/124; A61B 2018/143; A61B 2018/00666; A61B 2017/00039; A61B 2017/0019; A61N 1/327; A61N 2001/083
  USPC ............ 606/32–35, 38, 42; 607/98–101, 115
  See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |

(56) References Cited

U.S. PATENT DOCUMENTS

| | | |
|---|---|---|
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Aufer |
| 5,957,963 A | 9/1999 | Dobak, III |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,135,999 A | 10/2000 | Fanton et al. |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |

(56) References Cited

U.S. PATENT DOCUMENTS

| | | |
|---|---|---|
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |

(56) References Cited

U.S. PATENT DOCUMENTS

| | | |
|---|---|---|
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,700,368 B2 | 7/2017 | Callas et al. |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 | 11/2019 | Sano et al. |
| 10,537,379 B2 | 1/2020 | Sano et al. |
| 10,694,972 B2 | 6/2020 | Davalos et al. |
| 10,702,326 B2 | 7/2020 | Neal et al. |
| 10,828,085 B2 | 11/2020 | Davalos et al. |
| 10,828,086 B2 | 11/2020 | Davalos et al. |
| 10,959,772 B2 | 3/2021 | Davalos et al. |
| 11,254,926 B2 | 2/2022 | Garcia et al. |
| 11,272,979 B2 | 3/2022 | Garcia et al. |
| 11,311,329 B2 | 4/2022 | Davalos et al. |
| 11,382,681 B2 | 7/2022 | Arena et al. |
| 11,406,820 B2 | 8/2022 | Sano et al. |
| 11,453,873 B2 | 9/2022 | Davalos et al. |
| 11,607,271 B2 | 3/2023 | Garcia et al. |
| 11,607,537 B2 | 3/2023 | Latouche et al. |
| 11,638,603 B2 | 5/2023 | Sano et al. |
| 11,655,466 B2 | 5/2023 | Neal et al. |
| 11,737,810 B2 | 8/2023 | Davalos et al. |
| 11,890,046 B2 | 2/2024 | Neal et al. |
| 11,903,690 B2 | 2/2024 | Davalos et al. |
| 11,925,405 B2 | 3/2024 | Davalos et al. |
| 11,974,800 B2 | 5/2024 | Sano et al. |
| 12,059,197 B2 | 8/2024 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Edward |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |

(56) References Cited

U.S. PATENT DOCUMENTS

| | | |
|---|---|---|
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | McHale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0112141 A1 | 5/2005 | Terman |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016125 A1 | 1/2007 | Wong et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129720 A1 | 6/2007 | Demarais et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bomzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |

(56) References Cited

U.S. PATENT DOCUMENTS

| | | |
|---|---|---|
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326570 A1 | 12/2009 | Brown |
| 2010/0004623 A1 | 1/2010 | Hamilton, Jr. et al. |
| 2010/0006441 A1 | 1/2010 | Renaud et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1 | 4/2011 | Nuccitelli et al. |
| 2011/0106221 A1 | 5/2011 | Neal et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |
| 2011/0176037 A1 | 7/2011 | Benkley, III |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071870 A1 | 3/2012 | Salahieh et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0023871 A1 | 1/2013 | Collins |
| 2013/0030239 A1 | 1/2013 | Weyh et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0276748 A1 | 9/2014 | Ku et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1* | 3/2016 | Neal, II ............ A61B 18/1477 606/34 |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Onik et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0319851 A1 | 11/2017 | Athos et al. |
| 2017/0348525 A1 | 12/2017 | Sano et al. |
| 2017/0360326 A1 | 12/2017 | Davalos |
| 2018/0036529 A1* | 2/2018 | Jaroszeski ............ C12M 35/02 |
| 2018/0071014 A1 | 3/2018 | Neal et al. |
| 2018/0125565 A1 | 5/2018 | Sano et al. |
| 2018/0132922 A1* | 5/2018 | Neal, II ............ A61N 1/0412 |
| 2018/0161086 A1 | 6/2018 | Davalos et al. |

(56) References Cited

U.S. PATENT DOCUMENTS

| | | |
|---|---|---|
| 2018/0198218 A1 | 7/2018 | Regan et al. |
| 2019/0023804 A1 | 1/2019 | Onik et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0076528 A1 | 3/2019 | Soden et al. |
| 2019/0083169 A1 | 3/2019 | Single et al. |
| 2019/0133671 A1 | 5/2019 | Davalos et al. |
| 2019/0175248 A1 | 6/2019 | Neal, II |
| 2019/0175260 A1 | 6/2019 | Davalos |
| 2019/0223938 A1 | 7/2019 | Arena et al. |
| 2019/0232048 A1 | 8/2019 | Latouche et al. |
| 2019/0233809 A1 | 8/2019 | Neal et al. |
| 2019/0256839 A1 | 8/2019 | Neal et al. |
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |
| 2020/0405373 A1 | 12/2020 | O'Brien et al. |
| 2021/0022795 A1 | 1/2021 | Davalos et al. |
| 2021/0052882 A1 | 2/2021 | Wasson et al. |
| 2021/0113265 A1 | 4/2021 | D'Agostino et al. |
| 2021/0137410 A1 | 5/2021 | O'Brien et al. |
| 2021/0186600 A1 | 6/2021 | Davalos et al. |
| 2021/0361341 A1 | 11/2021 | Neal et al. |
| 2021/0393312 A1 | 12/2021 | Davalos et al. |
| 2022/0151688 A1 | 5/2022 | Garcia et al. |
| 2022/0161027 A1 | 5/2022 | Aycock et al. |
| 2022/0290183 A1 | 9/2022 | Davalos et al. |
| 2022/0362549 A1 | 11/2022 | Sano et al. |
| 2023/0157759 A1 | 5/2023 | Garcia et al. |
| 2023/0212551 A1 | 7/2023 | Neal et al. |
| 2023/0248414 A1 | 8/2023 | Sano et al. |
| 2023/0355293 A1 | 11/2023 | Davalos et al. |
| 2023/0355968 A1 | 11/2023 | Davalos et al. |
| 2024/0008911 A1 | 1/2024 | Davalos et al. |
| 2024/0074804 A1 | 3/2024 | Neal et al. |
| 2024/0173063 A1 | 5/2024 | Neal, II et al. |
| 2024/0268878 A1 | 8/2024 | Davalos et al. |
| 2024/0277245 A1 | 8/2024 | Davalos et al. |
| 2024/0299076 A1 | 9/2024 | O'Brien et al. |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A1 | 1/2011 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 863111 | 1/1953 |
| DE | 4000893 A1 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |

(56) References Cited

FOREIGN PATENT DOCUMENTS

| WO | 02100459 A | 12/2002 |
|---|---|---|
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |
| WO | 2017117418 A1 | 7/2017 |
| WO | 2020061192 A1 | 3/2020 |
| WO | 2022066768 A1 | 3/2022 |
| WO | 2023172773 A1 | 9/2023 |
| WO | 2024081749 A2 | 4/2024 |

OTHER PUBLICATIONS

Hughes, et al., An Analysis of Studies Comparing Electrical Impedance Tomography with X-Ray Videofluoroscopy in the Assessment of Swallowing, Physiol. Meas. 15, 1994, pp. A199-A209.

Ibey et al., "Selective cytotoxicity of intense nanosecond-duration electric pulses in mammalian cells." Biochimica Et Biophysica Acta-General Subjects, vol. 1800, pp. 1210-1219 (2010).

Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.

Ivanuša, et al., MRI Macromolecular Contrast Agents as Indicators of Changed Tumor Blood Flow, Radiol. Oncol. 2001; 35(2): 139-47.

Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.

Ivorra et al., "In vivo electric impedance measurements during and after electroporation of rat live." Bioelectrochemistry, vol. 70, pp. 287-295 (2007).

Ivorra et al., "In vivo electrical conductivity measurements during and after tumor electroporation: conductivity changes reflect the treatment outcome." Physics in Medicine and Biology, vol. 54, pp. 5949-5963 (2009).

Ivorra, "Bioimpedance monitoring for physicians: an overview." Biomedical Applications Group, 35 pages (2002).

Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).

Jarm et al., "Antivascular effects of electrochemotherapy: implications in treatment of bleeding metastases." Expert Rev Anticancer Ther. vol. 10, pp. 729-746 (2010).

Jaroszeski, et al., In Vivo Gene Delivery by Electroporation, Advanced Drug Delivery Review, vol. 35, pp. 131-137, 1999.

Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).

Jordan, D.W., et al., "Effect of pulsed, high-power radiofrequency radiation on electroporation of mammalian cells". Ieee Transactions on Plasma Science, 32(4): p. 1573-1578 (2004).

Jossinet et al., Electrical Impedance Endo-Tomography: Imaging Tissue From Inside, IEEE Transactions on Medical Imaging, vol. 21, No. 6, Jun. 2002, pp. 560-565.

Katsuki, S., et al., "Biological effects of narrow band pulsed electric fields", Ieee Transactions on Dielectrics and Electrical Insulation,. 14(3): p. 663-668 (2007).

Kingham et al., "Ablation of perivascular hepatic malignant tumors with irreversible electroporation." Journal of the American College of Surgeons, 2012. 215(3), p. 379-387.

Kinosita and Tsong, "Formation and resealing of pores of controlled sizes in human erythrocyte membrane." Nature, vol. 268 (1977) pp. 438-441.

Kinosita and Tsong, "Voltage-induced pore formation and hemolysis of human erythrocytes." Biochimica et Biophysica Acta (BBA)-Biomembranes, 471 (1977) pp. 227-242.

Kinosita et al., "Electroporation of cell membrane visualized under a pulsed-laser fluorescence microscope." Biophysical Journal, vol. 53, pp. 1015-1019 (1988).

Kinosita, et al., Hemolysis of Human Erythrocytes by a Transient Electric Field, Proc. Natl. Acad. Sci. USA, vol. 74, No. 5, pp. 1923-1927, 1977.

Kirson et al., "Alternating electric fields arrest cell proliferation in animal tumor models and human brain tumors." Proceedings of the National Academy of Sciences vol. 104, pp. 10152-10157 (2007).

Kolb, J.F., et al., "Nanosecond pulsed electric field generators for the study of subcellular effects", Bioelectromagnetics, 27(3): p. 172-187 (2006).

Kotnik and Miklavcic, "Theoretical evaluation of voltage inducement on internal membranes of biological cells exposed to electric fields." Biophysical Journal, vol. 90(2), pp. 480-491 (2006).

Kotnik et al., "Sensitivity of transmembrane voltage induced by applied electric fields—A theoretical analysis", Bioelectrochemistry and Bioenergetics, vol. 43, Issue 2, 1997, pp. 285-291.

Kotnik, T. and D. Miklavcic, "Theoretical evaluation of the distributed power dissipation in biological cells exposed to electric fields", Bioelectromagnetics, 21(5): p. 385-394 (2000).

Kotnik, T., et al., "Cell membrane electropermeabilization by symmetrical bipolar rectangular pulses. Part II. Reduced electrolytic contamination", Bioelectrochemistry, 54(1): p. 91-5 (2001).

Kotnik, T., et al., "Role of pulse shape in cell membrane electropermeabilization", Biochimica Et Biophysica Acta-Biomembranes, 1614(2): p. 193-200 (2003).

Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.

Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).

Lackovic, I., et al., "Three-dimensional Finite element Analysis of Joule Heating in Electrochemotherapy and in vivo Gene Electrotransfer", Ieee Transactions on Dielectrics and Electrical Insulation, 16(5): p. 1338-1347 (2009).

(56) References Cited

OTHER PUBLICATIONS

Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Laufer et al., "Electrical impedance characterization of normal and cancerous human hepatic tissue." Physiological Measurement, vol. 31, pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, E. W et al. Advanced Hepatic Ablation Technique for Creating Complete Cell Death : Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Lee, R. C., D. J. Canaday, and S. M. Hammer. Transient and stable ionic permeabilization of isolated skeletal muscle cells after electrical shock. J. Burn Care Rehabil. 14:528-540, 1993.
Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses". Ieee Transactions on Biomedical Engineering, 58(8) (2011).
Lundqvist, et al., Altering the Biochemical State of Individual Cultured Cells and Organelles with JItramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal pf General Physiology, vol. 26, 179-193, 1942.
Maek Lebar and Miklavi, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
(Arena, Christopher B. et al.) Co-pending U.S. Appl. No. 15/186,653, filed Jun. 20, 2016, and published as U.S. Publication No. 2016/0287314 on Oct. 6, 2016, Specification, Claims, Figures.
(Arena, Christopher B. et al.) Co-pending U.S. Appl. No. 16/372,520, filed Apr. 2, 2019, which published as 20190223938 on Jul. 25, 2019, Specification, Claims, Figures.
(Arena, Christopher B. et al.) Co-Pending Application No. PCT/US11/66239, filed Dec. 20, 2011, Specification, Claims, Figures.
(Arena, Christopher B. et al.) Co-Pending Application No. U.S. Appl. No. 13/332,133, filed Dec. 20, 2011 and published as U.S. Publication No. 2012/0109122 on May 3, 2012, Specification, Claims, Figures.

(Davalos, Rafael et al.) Co-pending U.S. Appl. No. 10/571,162, filed Oct. 18, 2006 (published as 2007/0043345 on Feb. 22, 2007), Specification, Figures, Claims.
(Davalos, Rafael et al.) Co-Pending U.S. Appl. No. 12/757,901, filed Apr. 9, 2010, Specification, Claims, Figures.
(Davalos, Rafael et al.) Co-Pending Application No. PCT/US04/43477, filed Dec. 21, 2004, Specification, Claims, Figures.
(Davalos, Rafael V. et al.) Co-Pending Application No. PCT/US10/53077, filed Oct. 18, 2010, Specification, Claims, Figures.
(Davalos, Rafael V. et al.) Co-Pending U.S. Appl. No. 12/491,151, filed Jun. 24, 2009, and published as U.S. Publication No. 2010/0030211 on Feb. 4, 2010, Specification, Claims, Figures.
(Davalos, Rafael V. et al.) Co-Pending U.S. Appl. No. 12/609,779, filed Oct. 30, 2009, and published as U.S. Publication No. 2010/0331758 on Dec. 30, 2010, Specification, Claims, Figures.
(Davalos, Rafael V. et al.) Co-Pending U.S. Appl. No. 13/919,640, filed Jun. 17, 2013, and published as U.S. Publication No. 2013/0281968 on Oct. 24, 2013, Specification, Claims, Figures.
(Davalos, Rafael V. et al.) Co-Pending U.S. Appl. No. 14/686,380, filed Apr. 14, 2015 and Published as US 2015/0289923 on Oct. 15, 2015, Specification, Claims, Figures.
(Davalos, Rafael V. et al.) Co-pending U.S. Appl. No. 15/424,335, filed Feb. 3, 2017, and published as U.S. Publication No. 2017/0189579 on Jul. 6, 2017, Specification, Claims, Figures.
(Davalos, Rafael V. et al.) Co-pending U.S. Appl. No. 15/536,333, filed Jun. 15, 2017, and published as U.S. Publication No. 2017/0360326 on Dec. 21, 2017, Specification, Claims, Figures.
(Davalos, Rafael V. et al.) Co-pending U.S. Appl. No. 15/881,414, filed Jan. 26, 2018, and published as U.S. Publication No. 2018/0161086 on Jun. 14, 2018, Specification, Claims, Figures.
(Davalos, Rafael V. et al.) Co-pending U.S. Appl. No. 16/177,745, filed Nov. 1, 2018, and published as U.S. Publication No. 2019/0069945 on Mar. 7, 2019, Specification, Claims, Figures.
(Davalos, Rafael V. et al.) Co-pending U.S. Appl. No. 16/232,962, filed Dec. 26, 2018, and published as U.S. Publication No. 2019/0133671 on May 9, 2019, Specification, Claims, Figures.
(Davalos, Rafael V. et al.) Co-pending U.S. Appl. No. 16/275,429, filed Feb. 14, 2019, which published as 2019/0175260 on Jun. 13, 2019, Specification, Claims, Figures.
(Davalos, Rafael V. et al.) Co-pending U.S. Appl. No. 16/352,759, filed Mar. 13, 2019, Specification, Claims, Figures.
(Davalos, Rafael V. et al.) Co-pending U.S. Appl. No. 16/535,451, filed Aug. 8, 2019, and Published as U.S. Publication No. 2019/0376055 on Dec. 12, 2019, Specification, Claims, Figures.
(Davalos, Rafael V. et al.) Co-pending U.S. Appl. No. 16/865,031, filed May 1, 2020, Specification, Claims, Figures.
(Davalos, Rafael V. et al.) Co-pending U.S. Appl. No. 17/069,359, filed Oct. 13, 2020, Specification, Claims, Drawings.
(Davalos, Rafael V. et al.) Co-Pending Application No. AU 2009243079, filed Apr. 29, 2009 (see PCT/US2009/042100 for documents as filed), Specification, Claims, Figures.
(Davalos, Rafael V. et al.) Co-Pending Application No. PCT/US09/62806, filed Oct. 30, 2009, Specification, Claims, Figures.
(Davalos, Rafael V. et al.) Co-Pending Application No. PCT/US10/30629, filed Apr. 9, 2010, Specification, Claims, Figures.
(Davalos, Rafael V. et al.) Co-pending application No. PCT/US19/51731 filed Sep. 18, 2019, Specification, Claims, Figures.
(Davalos, Rafael V. et al.) Co-Pending U.S. Appl. No. 14/017,210, filed Sep. 3, 2013, and published as U.S. Publication No. 2014/0039489 on Feb. 6, 2014, Specification, Claims, Figures.
(Davalos, Rafael V. et al.) Co-Pending U.S. Appl. No. 14/627,046, filed Feb. 20, 2015, and published as U.S. Publication No. 2015/0164584 on Jun. 18, 2015, Specification, Claims, Figures.
(Davalos, Rafael V. et al.) Co-Pending International Application No. PCT/US15/65792, filed Dec. 15, 2015, Specification, Claims, Drawings.
(Davalos, Rafael V.) Co-Pending U.S. Appl. No. 12/432,295, filed Apr. 29, 2009, and published as U. S. Publication No. 2009/0269317-A1 on Oct. 29, 2009, Specification, Figures, Claims.
(Davalos, Rafael V.) Co-pending U.S. Appl. No. 15/423,986, filed Feb. 3, 2017, and published as U.S. Publication No. 2017/0209620 on Jul. 27, 2017, Specification, Claims, Figures.

(56) References Cited

OTHER PUBLICATIONS (Davalos, Rafael V.) Co-Pending Application No. CA 2,722,296, filed Apr. 29, 2009, Amended Claims (7 pages), Specification, Figures (See PCT/US2009/042100 for Specification and figures as filed).
(Davalos, Rafael V.) Co-Pending Application No. EP 09739678.2 filed Apr. 29, 2009, Amended Claims (3 pages), Specification and Figures (See PCT/US2009/042100).
(Davalos, Rafael V.) Co-Pending Application No. PCT/US09/42100, filed Apr. 29, 2009, Specification, Claims, Figures.
(Davalos, Rafael V.) Co-Pending U.S. Appl. No. 14/012,832, filed Aug. 28, 2013, and published as U.S. Publication No. 2013/0345697 on Dec. 26, 2013, Specification, Claims, Figures.
(Davalos, Rafael V.) Co-Pending U.S. Appl. No. 14/558,631, filed Dec. 2, 2014, and published as U.S. Publication No. 2015/0088120 on Mar. 26, 2015, Specification, Claims, Figures.
Kgarcia, Paulo A. et al.) Co-Pending U.S. Appl. No. 15/011,752, filed Feb. 1, 2016, and published as U.S. Publication No. 2016/0143698 on May 26, 2016, Specification, Claims, Figures.
(Garcia, Paulo A. et al.) Co-Pending U.S. Appl. No. 16/655,845, filed Oct. 17, 2019, Specification, Claims, Figures.
(Garcia, Paulo A. et al.) Co-pending U.S. Appl. No. 16/152,743, filed Oct. 5, 2018, Specification, Claims, Figures.
(Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.
(Mahajan, Roop L. et al.) Co-Pending U.S. Appl. No. 13/958,152, filed Aug. 2, 2013, Specification, Claims, Figures.
(Neal, Robert E. et al.) Co-Pending U.S. Appl. No. 12/906,923, filed Oct. 18, 2010, Specification, Claims, Figures.
(Neal, Robert E. et al.) Co-Pending U.S. Appl. No. 14/808,679, filed Jul. 24, 2015 and Published as U.S. Publication No. 2015/0327944 on Nov. 19, 2015, Specification, Claims, Figures.
(Neal, Robert E. et al.) Co-pending U.S. Appl. No. 16/375,878, filed Apr. 5, 2019, which published on Aug. 1, 2019 as US 2019-0233809 A1, Specification, Claims, Figures.
(Neal, Robert E. et al.) Co-pending U.S. Appl. No. 16/404,392, filed May 6, 2019, and published as U. S. Publication No. 2019/0256839 on Aug. 22, 2019, Specification, Claims, Figures.
(Neal, Robert E. et al.) Co-Pending U.S. Appl. No. 16/865,772, filed May 4, 2020, Specification, Claims, Figures.
(Neal, Robert E. et al.) Co-Pending U.S. Appl. No. 13/550,307, filed Jul. 16, 2012, and published as U.S. Publication No. 2013/0184702 on Jul. 18, 2013, Specification, Claims, Figures.
(Neal, Robert E. et al.) Co-Pending U.S. Appl. No. 14/940,863, filed Nov. 13, 2015 and Published as US 2016/0066977 on Mar. 10, 2016, Specification, Claims, Figures.
(Neal, Robert E. et al.) Co-pending U.S. Appl. No. 16/280,511, filed Feb. 20, 2019, and published as U. S. Publication No. 2019/0175248 on Jun. 13, 2019, Specification, Claims, Figures.
(Neal, Robert E. et al.) Co-Pending Application No. EP 10824248.8, filed May 9, 2012, Amended Claims (3 pages), Specification and Figures (See PCT/US10/53077).
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Martinsen, O. G. and Grimnes, S., Bioimpedance and bioelectricity basics. Academic press, 2011.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185, 2008.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal II, R. E., et al. In Vitro and Numerical Support for Combinatorial Irreversible Electroporation and Electrochemotherapy Glioma Treatment. Annals of Biomedical Engineering, Oct. 29, 2013, 13 pages.
Neal II, R. E., et al., "Successful Treatment of a Large Soft Tissue Sarcoma with Irreversible Electroporation", Journal of Clinical Oncology, 29:13, e372-e377 (2011).
Neal II, R. E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal Re II, et al. (2013) Improved Local and Systemic Anti-Tumor Efficacy for Irreversible Electroporation in Immunocompetent ver-

(56) References Cited

OTHER PUBLICATIONS sus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
O'Brien, T. J. et al., "Effects of internal electrode cooling on irreversible electroporation using a perfused organ model," Int. J. Hyperth., vol. 35, No. 1, pp. 44-55, 2018.
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pakhomova, O. N., Gregory, B., Semenov I., and Pakhomov, A. G., BBA—Biomembr., 2014, 1838, 2547-2554.
Paszek et al., "Tensional homeostasis and the malignant phenotype." Cancer Cell, vol. 8, pp. 241-254 (2005).
Pavselj, N. et al. The course of tissue permeabilization studied on a mathematical model of a subcutaneous tumor in small animals. IEEE Trans Biomed Eng 52, 1373-1381 (2005).
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT Application No. PCT/2011/062067, International Preliminary Report on Patentability dated May 28, 2013.
PCT Application No. PCT/2011/066239, International Preliminary Report on Patentability dated Jun. 25, 2013.
PCT Application No. PCT/US09/62806, International Search Report (Jan. 19, 2010), Written Opinion (Jan. 19, 2010), and International Preliminary Report on Patentability (Jan. 4, 2010), 15 pgs.
PCT Application No. PCT/US10/53077, International Search Report (Aug. 2, 2011), Written Opinion (Aug. 2, 2011), and International Preliminary Report on Patentability (Apr. 17, 2012).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747, First Office Action (Translation) dated Feb. 21, 2019, 5 pages.
Pending Application No. JP 2016-567747, First Office Action dated Feb. 21, 2019, 4 pages.
Pending Application No. JP 2019-133057, amended claims (English language version) filed Aug. 14, 2019, 5 pages.
Pending Application No. JP 2019-133057, Office Action dated Sep. 14, 2020, 5 pages (and English translation, 6 pages).
Phillips, M., Maor, E. & Rubinsky, B. Non-Thermal Irreversible Electroporation for Tissue Decellularization. J. Biomech. Eng, doi: 10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).
Rajagopal, V. and S.G. Rockson, Coronary restenosis: a review of mechanisms and management, The American Journal of Medicine, 2003, 115(7): p. 547-553.
Reberek, M. and D. Miklavčič, "Advantages and Disadvantages of Different Concepts of Electroporation Pulse Generation," Automatika 52(2011) 1, 12-19.
Ringel-Scaia, V. M. et al., High-frequency irreversible electroporation is an effective tumor ablation strategy that Induces immunologic cell death and promotes systemic anti-tumor immunity. EBioMedicine, 2019, 44, 112-125.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
SAI Infusion Technologies, "Rabbit Ear Vein Catheters", https://www.sai-infusion.com/products/rabbit-ear-catheters, Aug. 10, 2017 webpage printout, 5 pages.
Salford, L.G., et al., "A new brain tumour therapy combining bleomycin with in vivo electropermeabilization", Biochem. Biophys. Res. Commun., 194(2): 938-943 (1993).

(56) References Cited

OTHER PUBLICATIONS

Salmanzadeh et al., "Investigating dielectric properties of different stages of syngeneic murine ovarian cancer cells" Biomicrofluidics 7, 011809 (2013), 12 pages.

Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).

Salmanzadeh et al., "Sphingolipid Metabolites Modulate Dielectric Characteristics of Cells in a Mouse Ovarian Cancer Progression Model." Integr. Biol., 5(6), pp. 843-852 (2013).

Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.

Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601, 2011.

Sano et al., "Contactless Dielectrophoretic Spectroscopy: Examination of the Dielectric Properties of Cells Found in Blood." Electrophoresis, 32, pp. 3164-3171, 2011.

Sano et al., "In-vitro bipolar nano- and microsecond electro-pulse bursts for irreversible electroporation therapies." Bioelectrochemistry vol. 100, pp. 69-79 (2014).

Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).

Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.

Saur et al., "CXCR4 expression increases liver and lung metastasis in a mouse model of pancreatic cancer." Gastroenterology, vol. 129, pp. 1237-1250 (2005).

Schmukler, Impedance Spectroscopy of Biological Cells, Engineering in Medicine and Biology Society, Engineering Advances: New Opportunities for Biomedical Engineers, Proceedings of the 16th Annual Internal Conference of the EEE, vol. 1, p. A74, downloaded from IEEE Xplore website, 1994.

Schoenbach et al., "Intracellular effect of ultrashort electrical pulses." Bioelectromagnetics, 22 (2001) pp. 440-448.

Seibert et al., "Clonal variation of MCF-7 breast cancer cells in vitro and in athymic nude mice." Cancer Research, vol. 43, pp. 2223-2239 (1983).

Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).

Sel, D. et al. Sequential finite element model of tissue electropermeabilization. IEEE Transactions on Biomedical Engineering 52, 816-827, doi:10.1109/tbme.2005.845212 (2005).

Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).

Sersa, et al., Reduced Blood Flow and Oxygenation in SA-1 Tumours after Electrochemotherapy with Cisplatin, British Journal of Cancer, 87, 1047-1054, 2002.

Sersa, et al., Tumour Blood Flow Modifying Effects of Electrochemotherapy: a Potential Vascular Targeted Mechanism, Radiol. Oncol., 37(1): 43-8, 2003.

Shao, Qi et al. Engineering T cell response to cancer antigens by choice of focal therapeutic conditions, International Journal of Hyperthermia, 2019, DOI: 10.1080/02656736.2018.1539253.

Sharma, A., et al., "Review on Thermal Energy Storage with Phase Change Materials and Applications", Renewable Sustainable Energy Rev. 13(2), 318-345 (2009).

Sharma, et al., Poloxamer 188 Decreases Susceptibility of Artificial Lipid Membranes to Electroporation, Biophysical Journal, vol. 71, No. 6, pp. 3229-3241, Dec. 1996.

Shiina, S., et al, Percutaneous ethanol injection therapy for hepatocellular carcinoma: results in 146 patients. AJR, 1993, 160: p. 1023-8.

Pending U.S. Appl. No. 17/172,731, Preliminary Amendment, filed Jun. 27, 2022, 9 pages.

Pending U.S. Appl. No. 17/172,731, Preliminary Amendment, filed Sep. 17, 2021, 7 pages.

Pending U.S. Appl. No. 17/172,731, Response to Feb. 15, 2023 Non-Final Office Action, dated May 15, 2023, 8 pages.

Pending U.S. Appl. No. 17/172,731, Response to Jul. 12, 2023 Final Office Action, dated Oct. 12, 2023, 10 pages.

Pending U.S. Appl. No. 17/277,662 Non-Final Office Action dated May 5, 2023, 9 pages.

Pending U.S. Appl. No. 17/277,662 Notice of Allowance dated Oct. 2, 2023, 7 pages.

Pending U.S. Appl. No. 17/277,662 Preliminary Amendment filed Mar. 18, 2021, 8 pages.

Pending U.S. Appl. No. 17/277,662 Response to May 5, 2023 Non-Final Office Action, dated Aug. 7, 2023, 8 pages.

Pending U.S. Appl. No. 17/338,960, Ex Parte Quayle Action dated May 24, 2023, 6 pages.

Pending U.S. Appl. No. 17/338,960, Response to May 24, 2023 Ex Parte Quayle Action, dated Aug. 8, 2023, 6 pages.

Pending U.S. Appl. No. 17/338,960, Response to Notice to File Missing Parts and Amendment, filed Aug. 16, 2021, 7 pages.

Pending U.S. Appl. No. 17/591,992, Preliminary Amendment dated Sep. 20, 2023, 9 pages.

Pending U.S. Appl. No. 18/027,824, Preliminary Amendment dated Mar. 22, 2023, 8 pages.

Pending U.S. Appl. No. 18/100,835, Preliminary Amendment filed Jan. 26, 2023, 8 pages.

Pending U.S. Appl. No. 18/100,835, Second Preliminary Amendment filed Feb. 6, 2023, 6 pages.

Pending U.S. Appl. No. 18/120,158, Preliminary Amendment dated Mar. 13, 2023, 195 pages.

Pending U.S. Appl. No. 18/123,719, Preliminary Amendment dated Jun. 6, 2023, 6 pages.

Pending U.S. Appl. No. 18/130,330, Preliminary Amendment dated Jun. 20, 2023, 8 pages.

Pending U.S. Appl. No. 18/348,605, Preliminary Amendment dated Oct. 31, 2023, 7 pages.

Pending U.S. Appl. No. 18/502,967, Preliminary Amendment filed Nov. 6, 2023, 6 pages.

Pending Application No. 19861489.3 Extended European Search Report dated May 16, 2022 (8 pages).

Pending Application No. 19861489.3 Response to Communication pursuant to Rules 161(2) and 162 EPC, filed Nov. 16, 2021, 7 pages.

Pending Application No. 19861489.3 Response to May 16, 2022 Extended European Search Report, dated Dec. 13, 2022, 136 pages.

Pending Application No. AU 2015259303, Certificate of Grant dated Feb. 10, 2022, 1 page.

Pending Application No. AU 2015259303, Notice of Acceptance and Allowed Claims, dated Oct. 15, 2021, 7 pages.

Pending Application No. AU 2015259303, Response to First Examination Report dated Sep. 20, 2021, 126 pages.

Pending Application No. CN 201580025135.6, First Office Action, dated Sep. 25, 2019 (Chinese and English Versions, each 6 pages).

Pending Application No. CN 201580025135.6, Response to First Office Action, Feb. 7, 2020, (Chinese Vrsion, 13 pages, and English Version, 10 pages).

Pending Application No. CN 201580025135.6, Second Office Action, dated Apr. 29, 2020 (Chinese Version, 4 pages, and English Version, 7 pages).

Pending Application No. CN 202011281572.3, Amendment filed Sep. 8, 2021 (16 pages) with English Version of the Amended Claims (7 pages).

Pending Application No. EP 15793361.5, Communication Pursuant to Article 94(3) EPC, dated Apr. 4, 2023, 4 pages.

Pending Application No. EP 15793361.5, Communication Pursuant to Article 94(3) EPC, dated May 3, 2021, 4 pages.

(56) References Cited

OTHER PUBLICATIONS

Pending Application No. EP 15793361.5, Response to Apr. 4, 2023 Communication Pursuant to Article 94(3) EPC, dated Oct. 16, 2023, 13 pages.
Pending Application No. EP 15793361.5, Response to May 3, 2021 Communication Pursuant to Article 94(3) EPC, dated Nov. 12, 2021, 12 pages.
Pending Application No. JP 2019-133057, Office Action dated Sep. 1, 2021, 3 pages (and English translation, 4 pages).
Pending Application No. JP 2019-133057, Request for Amendment and Appeal filed Dec. 23, 2021 (8 pages) with English Translation of the Amended Claims (2 pages).
Pending Application No. JP 2019-133057, Response to Sep. 14, 2020 Office Action filed Mar. 18, 2021 (6 pages) with English Version of claims and response (5 pages).
Pending Application No. PCT/US21/51551, International Search Report and Written Opinion dated Dec. 29, 2021, 14 pages.
Pending Application No. PCT/US23/15118, International Search Report and Written Opinion dated Jul. 31, 2023, 18 pages.
Pending Application No. PCT/US23/15118, Invitation to Pay Additional Fees dated May 17, 2023, 3 pages.
Polajžer, T. et al., "Cancellation effect is present in high-frequency reversible and irreversible electroporation," Bioelectrochemistry, vol. 132, 2020, 11 pages.
Reilly, J. P. et al., "Sensory Effects of Transient Electrical Stimulation—Evaluation with a Neuroelectric Model," IEEE Trans. Biomed. Eng., vol. BME-32, No. 12, 1001-1011, 1985, 11 pages.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
Rubinsky, L. et al., "Electrolytic Effects During Tissue Ablation by Electroporation," Technol. Cancer Res. Treat., vol. 15, No. 5, NP95-103, 2016, 9 pages.
Sano, M. B. et al., "Burst and continuous high frequency irreversible electroporation protocols evaluated in a 3D tumor model," Phys. Med. Biol., vol. 63, No. 13, 2018, 17 pages.
Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.
U.S. Appl. No. 14/808,679 (U.S. Pat. No. 11,655,466), file history through Aug. 2022, 253 pages.
U.S. Appl. No. 16/152,743 (U.S. Pat. No. 11,272,979), file history through Jan. 2022, 89 pages.
U.S. Appl. No. 16/210,771 U.S. Pat. No. 11,607,537), file history through Dec. 2022, 139 pages.
U.S. Appl. No. 16/275,429 (U.S. Pat. No. 10,959,772), file history through Feb. 2021, 18 pages.
U.S. Appl. No. 16/280,511, file history through Aug. 2021, 31 pages.
U.S. Appl. No. 16/352,759 (U.S. Pat. No. 11,311,329), file history through Mar. 2022, 258 pages.
U.S. Appl. No. 16/372,520 (U.S. Pat. No. 11,382,681), file history through Jun. 2022, 107 pages.
U.S. Appl. No. 16/404,392 (U.S. Pat. No. 11,254,926), file history through Jan. 2022, 153 pages.
U.S. Appl. No. 16/443,351 (U.S. Pat. No. 11,638,603), file history through Mar. 2023, 114 pages.
U.S. Appl. No. 16/520,901 (U.S. Pat. No. 11,406,820) file history through May 2022, 39 pages.
U.S. Appl. No. 16/535,451 (U.S. Pat. No. 11,453,873), file history through Aug. 2022, 85 pages.
U.S. Appl. No. 16/655,845 (U.S. Pat. No. 11,607,271), file history through Jan. 2023, 68 pages.
U.S. Appl. No. 17/069,359 (U.S. Pat. No. 11,737,810), file history through Apr. 2023, 27 pages.
Valdez, C. M. et al., "The interphase interval within a bipolar nanosecond electric pulse modulates bipolar cancellation," Bioelectromagnetics, vol. 39, No. 6, 441-450, 2018, 28 pages.
Verma, A. et al., "Primer on Pulsed Electrical Field Ablation: Understanding the Benefits and Limitations," Circ. Arrhythmia Electrophysiol., No. September, pp. 1-16, 2021, 16 pages.
Vižintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Zhao, J. et al. "Irreversible electroporation reverses resistance to immune checkpoint blockade in pancreatic cancer", Nature Communications (2019) 10:899, 14 pages.
Pending U.S. Appl. No. 17/000,049, Non-Final Office Action dated Dec. 11, 2023, 13 pages.
Szot et al., "3D in vitro bioengineered tumors based on collagen I hydrogels." Biomaterials vol. 32, pp. 7905-7912 (2011).
Talele, S. and P. Gaynor, "Non-linear time domain model of electropermeabilization: Effect of extracellular conductivity and applied electric field parameters", Journal of Electrostatics, 66(5-6): p. 328-334 (2008).
Talele, S. and P. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journal of Electrostatics, 68(3): p. 261-274 (2010).
Teissie, J. and T.Y. Tsong, "Electric-Field Induced Transient Pores in Phospholipid-Bilayer Vesicles". Biochemistry, 20(6): p. 1548-1554 (1981).
Tekle, Ephrem, R. Dean Astumian, and P. Boon Chock, Electroporation by using bipolar oscillating electric field: An Improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
Tibbitt et al., "Hydrogels as Extracellular Matrix Mimics for 3D Cell Culture", Jul. 2009, Biotechnol Bioeng, 103 (4),655-663.
U.S. Appl. No. 12/432,295 (U.S. Pat. No. 9,598,691), file history through Jan. 2017, 334 pages.
U.S. Appl. No. 12/491,151 (U.S. Pat. No. 8,992,517), file history through Feb. 2015, 113 pages.
U.S. Appl. No. 12/609,779 (U.S. Pat. No. 8,465,484), file history through May 2013, 100 pages.
U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history through Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.

(56) References Cited

OTHER PUBLICATIONS

U.S. Appl. No. 14/627,046 (U.S. Pat. No. 10,245,105), file history through Feb. 2019, 77 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 bages.
U.S. Appl. No. 15/186,653 (U.S. Pat. No. 10,292,755), file history through Mar. 2019, 21 pages.
U.S. Appl No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
U.S. Appl. No. 15/843,888 (U.S. Pat. No. 10,537,379), file history through Sep. 2019, 83 pages.
U.S. Appl. No. 15/881,414 (U.S. Pat. No. 10,154,874), file history through Nov. 2018, 43 pages.
U.S. Appl. No. 16/177,745 (Patented), file history through Jun. 2020, 57 pages.
U.S. Appl. No. 16/232,962 (Patented), file history through Jun. 2020, 44 pages.
Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.
Verbridge et al., "Oxygen-Controlled Three-Dimensional Cultures to Analyze Tumor Angiogenesis." Tissue Engineering, Part A vol. 16, pp. 2133-2141 (2010).
Vernier, P.T., et al., "Nanoelectropulse-driven membrane perturbation and small molecule permeabilization", Bmc Cell Biology, 7 (2006).
Vidamed, Inc., Transurethral Needle Ablation (TUNA): Highlights from Worldwide Clinical Studies, Vidamed's Office TUNA System, 2001.
Voyer, D., A. Silve, L. M. Mir, R. Scorretti, and C. Poignard, "Dynamical modeling of tissue electroporation," Bioelectrochemistry, vol. 119, pp. 98-110, 2018.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional Intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
PCT Application No. PCT/US15/30429, International Search Report and Written Opinion dated Oct. 16, 2015, 19 pages.
PCT Application No. PCT/US15/30429, International Report on Patentability dated Nov. 15, 2016.
PCT Application No. PCT/US15/65792, International Search Report (Feb. 9, 2016), Written Opinion (Feb. 9, 2016), and International Preliminary Report on Patentability (Jun. 20, 2017), 15 pages.
PCT Application No. PCT/US19/51731, International Search Report and Written Opinion dated Feb. 20, 2020, 19 pgs.
PCT Application No. PCT/US19/51731, Invitation to Pay Additional Search Fees dated Oct. 28, 2019, 2 pgs.
PCT Application No. PCT/US2004/043477, International Search Report (Aug. 26, 2005), Written Opinion (Aug. 26, 2005), and International Preliminary Report on Patentability (Jun. 26, 2006).
PCT Application No. PCT/US2009/042100, International Search Report (Jul. 9, 2009), Written Opinion (Jul. 9, 2009), and International Preliminary Report on Patentability (Nov. 2, 2010).
PCT Application No. PCT/US2010/029243, International Search Report, 4 pgs, (Jul. 30, 2010), Written Opinion, 7 pgs, (Jul. 30, 2010), and International Preliminary Report on Patentability, 8 pgs, (Oct. 4, 2011).
PCT Application No. PCT/US2010/030629, International Search Report (Jul. 15, 2010), Written Opinion (Jul. 15, 2010), and International Preliminary Report on Patentability (Oct. 11, 2011).
PCT Application No. PCT/US2011/062067, International Search Report and Written Opinion dated Jul. 25, 2012.
PCT Application No. PCT/US2011/066239, International Search Report (Aug. 22, 2012), and Written Opinion (Aug. 22, 2012).
Pending U.S. Appl. No. 14/686,380, Final Office Action dated May 9, 2018, 14 pages.
Pending U.S. Appl. No. 14/686,380, Final Office Action dated Oct. 6, 2020, 14 pages.
Pending U.S. Appl. No. 14/686,380, Final Office Action dated Sep. 3, 2019, 28 pages.
Pending U.S. Appl. No. 14/686,380, Non-Final Office Action dated Feb. 13, 2020, 11 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Response to Feb. 13, 2020 Non-Final Office Action, filed Jul. 1, 2020, 8 pages.
Pending U.S. Appl. No. 14/686,380, Response to Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.
Pending U.S. Appl. No. 14/686,380, Response to Non-Final Office Action Filed Aug. 1, 2019, 11 pages.
Pending U.S. Appl. No. 14/686,380, Response to Nov. 22, 2017 Non-Final Office Action dated Mar. 28, 2018, 11 pages.
Pending U.S. Appl. No. 14/686,380, Response to Sep. 3, 2019 Final Office Action, filed Jan. 3, 2020, 10 pages.
Pending U.S. Appl. No. 14/686,380, Restriction Requirement Jul. 19, 2017, 7 pages.
Pending U.S. Appl. No. 14/808,679, Interview Summary, Apr. 26, 2019, 3 pages.
Pending U.S. Appl. No. 14/808,679, Preliminary Amendment Jul. 24, 2015, 6 pages.
Pending U.S. Appl. No. 14/808,679, Restriction Requirement dated Mar. 19, 2018, 7 pages.
Pending U.S. Appl. No. 14/808,679, 3rd Renewed Petition, Dec. 9, 2019 and Petition Decision Dec. 18. 2019, 11 pages.
Pending U.S. Appl. No. 14/808,679, Final Office Action dated Jan. 11, 2019, 12 pages.
Pending U.S. Appl. No. 14/808,679, Interview Summary dated Apr. 26, 2019, 3 pages.
Pending U.S. Appl. No. 14/808,679, Non-Final Office Action dated Jun. 12, 2020, 10 pages.
Pending U.S. Appl. No. 14/808,679, Non-Final Office Action dated Sep. 10, 2018, 12 pages.

(56) References Cited

OTHER PUBLICATIONS

Pending U.S. Appl. No. 14/808,679, Petition Decision, dated Oct. 1, 2019, 5 pages.
Pending U.S. Appl. No. 14/808,679, Petition Decision, dated Oct. 23, 2019, 6 pages.
Pending U.S. Appl. No. 14/808,679, Petition Decision, Dec. 3, 2019, 5 pages.
Pending U.S. Appl. No. 14/808,679, Petition for Priority and Supplemental Response, filed May 8, 2019, 25 pages.
Pending U.S. Appl. No. 14/808,679, Petition Supplement, Sep. 25, 2019, 10 pages.
Pending U.S. Appl. No. 14/808,679, Petition, May 8, 2019, 2 pages.
Pending U.S. Appl. No. 14/808,679, Preliminary Amendment, filed Jul. 27, 2015, 9 pages.
Pending U.S. Appl. No. 14/808,679, RCE filed Apr. 11, 2019, 8 pages.
Pending U.S. Appl. No. 14/808,679, Renewed Petition, filed Oct. 9, 2019, 1 pages.
Pending U.S. Appl. No. 14/808,679, Response to Mar. 19, 2018 Restriction Requirement dated May 21, 2018, 2 pages.
Pending U.S. Appl. No. 14/808,679, Response to Non-Final Office Action dated Jun. 12, 2020, filed Sep. 14, 2020, 9 pages.
Pending U.S. Appl. No. 14/808,679, Response to Sep. 10, 2018 Non-Final Office Action dated Dec. 10, 2018, 9 pages.
Pending U.S. Appl. No. 14/808,679, Second Renewed Petition, filed Oct. 31, 2019, 3 pages.
Pending U.S. Appl. No. 14/808,679, Supplemental Response, May 8, 2019, 16 pages.
Pending U.S. Appl. No. 16/152,743 Preliminary Amendment filed Oct. 5, 2018, 7 pages.
Pending U.S. Appl. No. 16/152,743, Non-Final Office Action dated Sep. 25, 2020, 10 pages.
Pending U.S. Appl. No. 16/152,743, Second Preliminary Amendment filed May 2, 2019, 6 pages.
Pending U.S. Appl. No. 16/210,771, Non-Final Office Action dated Sep. 3, 2020, 9 pages.
Pending U.S. Appl. No. 16/210,771, Preliminary Amendment filed Dec. 5, 2018, 8 pages.
Pending U.S. Appl. No. 16/210,771, Response to Restriction Requirement, filed Jul. 8, 2020, 7 pages.
Pending U.S. Appl. No. 16/210,771, Restriction Requirement, dated Jun. 9, 2020, 7 pages.
Pending U.S. Appl. No. 16/210,771, Second Preliminary Amendment filed Oct. 14, 2019, 7 pages.
Pending U.S. Appl. No. 16/275,429 Notice of Allowance dated Nov. 10, 2020, 9 pages.
Pending U.S. Appl. No. 16/275,429 Preliminary Amendment Filed Mar. 28, 2019, 6 pages.
Pending U.S. Appl. No. 16/280,511, Preliminary Amendment filed Nov. 2, 2020, 6 pages.
Pending U.S. Appl. No. 16/372,520 Preliminary Amendment filed Apr. 9, 2019, 7 pages.
Pending U.S. Appl. No. 16/375,878, Preliminary Amendment, filed Apr. 9, 2019, 9 pages.
Pending U.S. Appl. No. 16/375,878, Second Preliminary Amendment, filed Feb. 5, 2020, 3 pages.
Pending U.S. Appl. No. 16/404,392, Final Office Action dated Mar. 20, 2020, 8pgs.
Pending U.S. Appl. No. 16/404,392, Non-Final Office Action dated Sep. 6, 2019, 8pgs.
Pending U.S. Appl. No. 16/404,392, Petition for Priority, filed Jun. 4, 2019, 2 pages.
Pending U.S. Appl. No. 16/404,392, Preliminary Amendment, filed Jun. 4, 2019, 9 pages.
Pending U.S. Appl. No. 16/404,392, Preliminary Amendment, filed Jun. 6, 2019, 5 pages.
Pending U.S. Appl. No. 16/404,392, Response to Final Office action dated Mar. 20, 2020, filed Sep. 18, 2020, 7 pages.
Pending U.S. Appl. No. 16/404,392, Response to Non-Final Office action dated Sep. 6, 2019, filed Dec. 6, 2019, 8 pages.
Pending U.S. Appl. No. 16/443,351, Preliminary amendment filed Feb. 3, 2020.
Pending U.S. Appl. No. 16/520,901, Preliminary Amendment filed Aug. 14, 2019.
Pending U.S. Appl. No. 16/520,901, Second Preliminary Amendment filed Feb. 4, 2020.
Pending U.S. Appl. No. 16/535,451 Preliminary Amendment filed Aug. 8, 2019, 3 pages.
Pending U.S. Appl. No. 16/535,451 Second Preliminary Amendment filed Oct. 9, 2019, 15 pages.
Pending U.S. Appl. No. 16/535,451 Third Preliminary Amendment filed Nov. 5, 2019, 4 pages.
Pending U.S. Appl. No. 16/655,845, Preliminary Amendment filed Oct. 16, 2020, 6 pages.
Pending U.S. Appl. No. 16/747,219, Preliminary Amendment filed Jan. 20, 2020, 5 pages.
Pending U.S. Appl. No. 16/865,031, Preliminary Amendment filed May 1, 2020, 7 pages.
Pending U.S. Appl. No. 16/865,772, Preliminary Amendment filed May 4, 2020, 6 pages.
Pending U.S. Appl. No. 16/915,760, Preliminary Amendment filed Jul. 6, 2020, 5 pages.
Pending Application No. AU 2009243079, First Examination Report, Jan. 24, 2014, 4 pages.
Pending Application No. AU 2009243079, Voluntary Amendment filed Dec. 6, 2010, 35 pages.
Pending Application No. AU 2015259303, First Examination Report dated Oct. 26, 2020, 6 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application Nov. 14, 2016.
Pending Application No. CN 201580025135.6 Response to Sep. 25, 2019 Office action, filed Feb. 10, 2020, English language version and original document.
Pending Application No. EP 09739678.2 Extended European Search Report dated May 11, 2012, 7 pages.
Pending Application No. EP 09739678.2, Communication pursuant to Rule 94.3, Apr. 16, 2014, 3 pages.
Pending Application No. EP 09739678.2, Office Action dated Apr. 16, 2014, 3 pages.
Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (Jan. 20, 2014), 6 pages.
Pending Application No. EP 10824248.8, Invitation Pursuant to rule 62a(1) EPC (Sep. 25, 2013), 2 pages.
Pending Application No. EP 10824248.8, Communication Pursuant to Rule 70(2) dated Feb. 6, 2014, 1 page.
Pending Application No. EP 10824248.8, Response to Invitation Pursuant to rule 62a(1) EPC (Sep. 25, 2013), Response filed Nov. 18, 2013.
Pending Application No. EP 11842994.3, Communication Pursuant to Rules 70(2) and 70a(2) EPC dated Apr. 28, 2014, 1 page.
Pending Application No. EP 11842994.3, Extended European Search Report dated Apr. 9, 2014, 34 bages.
Pending Application No. EP 15793361.5, Claim amendment filed Jul. 18, 2018, 13 pages.
Pending Application No. EP 15793361.5, European Search Report dated Dec. 4, 2017, 9 pages.
Pending Application No. JP 2013-541050, Voluntary Amendment filed Oct. 29, 2013, 4 pages (with English Version of the Claims, 2 pages).
(O'Brien, Timothy J. et al.) Co-Pending U.S. Appl. No. 16/915,760, filed Jun. 29, 2020, Specification, Claims, Figures.
(Pearson, Robert M. et al) Co-pending Application No. PCT/US2010/029243, filed Mar. 30, 2010, published as WO 2010/117806 on Oct. 14, 2010, Specification, Claims, Figures.

(56) References Cited

OTHER PUBLICATIONS (Pearson, Robert M. et al.) Co-pending U.S. Appl. No. 12/751,826, filed Mar. 31, 2010 (published as 2010/0250209 on Sep. 30, 2010), Specification, Claims, Figures.
(Pearson, Robert M. et al.) Co-pending U.S. Appl. No. 12/751,854, filed Mar. 31, 2010 (published as 2010/0249771 on Sep. 30, 2010), Specification, Claims, Figures.
(Sano, Michael B. et al) Co-Pending Application No. PCT/US2015/030429, Filed May 12, 2015, Published on Nov. 19, 2015 as WO 2015/175570, Specification, Claims, Figures.
(Sano, Michael B. et al.) Co-Pending U.S. Appl. No. 13/989,175, filed May 23, 2013, and published as U.S. Publication No. 2013/0253415 on Sep. 26, 2013, Specification, Claims, Figures.
(Sano, Michael B. et al.) Co-Pending U.S. Appl. No. 15/310,114, filed Nov. 10, 2016, and published as U.S. Publication No. 2017/0266438 on Sep. 21, 2017, Specification, Claims, Figures.
(Sano, Michael B. et al.) Co-pending U.S. Appl. No. 15/843,888, filed Dec. 15, 2017, and published as U.S. Publication No. 2018/0125565 on May 10, 2018, Specification, Claims, Figures.
(Sano, Michael B. et al.) Co-pending U.S. Appl. No. 16/443,351, filed Jun. 17, 2019 (published as 20190328445 on Oct. 31, 2019), Specification, Claims, Figures.
(Sano, Michael B. et al.) Co-pending U.S. Appl. No. 16/520,901, filed Jul. 24, 2019, and published as U.S. Publication No. 2019/0351224 on Nov. 21, 2019, Specification, Claims, Figures.
(Sano, Michael B. et al.) Co-pending U.S. Appl. No. 16/747,219, filed Jan. 20, 2020, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).
(Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-pending Application No. JP 2019-133057 filed Jul. 18, 2019, 155 pgs, Specification, Claims, Figures (See PCT/US15/30429 for English Version of documents as filed).
(Sano, Michael B. et al.) Co-Pending Application No. PCT/US11/62067, filed Nov. 23, 2011, Specification, Claims, Figures.
(Wasson, Elisa M. et al.) Co-pending U.S. Appl. No. 17/000,049, filed Aug. 21, 2020, Specification, Claims, Figures.
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Al-Sakere et al., "Tumor ablation with irreversible electroporation," PLoS ONE, 2, e1135, 2007, 8 pages.
Amasha, et al., Quantitative Assessment of Impedance Tomography for Temperature Measurements in Microwave Hyperthermia, Clin. Phys. Physiol. Meas., 1998, Suppl. A, 49-53.

Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al., "Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)-Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Beebe, S.J., et al.,, "Nanosecond, high-intensity pulsed electric fields induce apoptosis in human cells", FASEB J, 17(9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, E. et al., "Irreversible Electroporation: Treatment Effect Is Susceptible to Local Environment and Tissue Properties," Radiology, vol. 269, No. 3, 2013, 738-747.
Ben-David, E., et al., "Characterization of Irreversible Electroporation Ablation in In Vivo Procine Liver" Am. J. Roentgenol. 198(1), W62-W68 (2012).
Benz, R., et al. "Reversible electrical breakdown of lipid bilayer membranes: a charge-pulse relaxation study". J Membr Biol, 48(2): p. 181-204 (1979).

(56) References Cited

OTHER PUBLICATIONS

Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S., M. F. Lorenzo, A. Safaai-Jazi, and R. V. Davalos, "Characterization of nonlinearity and dispersion in issue impedance during high-frequency electroporation," IEEE Transactions on Biomedical Engineering, vol. 65, No. 10, pp. 2190-2201, 2018.
Blad, et al., Impedance Spectra of Tumour Tissue in Comparison with Normal Tissue; a Possible Clinical Application for Electrical Impedance Tomography, Physiol. Meas. 17 (1996) A105-A115.
Pending U.S. Appl. No. 14/686,380, Response to Oct. 6, 2020 Final Office Action with RCE, dated Jan. 6, 2020, 11 pages.
Pending U.S. Appl. No. 14/686,380, Amendment after Notice of Appeal, dated Oct. 12, 2021, 6 pages.
Pending U.S. Appl. No. 14/686,380, Non-Final Office Action dated May 7, 2021, 17 pages.
Pending U.S. Appl. No. 16/375,878, Applicant-Initiated Interview Summary dated Aug. 23, 2022, 7 pages.
Pending U.S. Appl. No. 16/375,878, Final Office Action dated Apr. 15, 2022, 8 pages.
Pending U.S. Appl. No. 16/375,878, Final Office Action dated Aug. 18, 2023, 11 pages.
Pending U.S. Appl. No. 16/375,878, Non-Final Office Action dated Jan. 23, 2023, 8 pages.
Pending U.S. Appl. No. 16/375,878, Non-Final Office Action dated Jun. 24, 2021, 8 pages.
Pending U.S. Appl. No. 16/375,878, Notice of Allowance dated Nov. 15, 2023, 6 pages.
Pending U.S. Appl. No. 16/375,878, Response to Apr. 15, 2022 Final Office Action, dated Aug. 15, 2022, 8 pages.
Pending U.S. Appl. No. 16/375,878, Response to Aug. 18, 2023 Final Office Action, dated Oct. 18, 2023, 9 pages.
Pending U.S. Appl. No. 16/375,878, Response to Jan. 23, 2023 Non-Final Office Action, dated Apr. 24, 2023, 10 pages.
Pending U.S. Appl. No. 16/375,878, Response to Jun. 24, 2021 Non-Final Office Action, dated Dec. 22, 2021, 8 pages.
Pending U.S. Appl. No. 16/747,219, Applicant-Initiated Interview Summary dated Aug. 3, 2022, 4 pages.
Pending U.S. Appl. No. 16/747,219, Final Office Action dated Nov. 10, 2022, 12 pages.
Pending U.S. Appl. No. 16/747,219, Non-Final Office Action dated Mar. 31, 2022, 12 pages.
Pending U.S. Appl. No. 16/747,219, Non-Final Office Action dated May 25, 2023, 13 pages.
Pending U.S. Appl. No. 16/747,219, Preliminary Amendment filed Jan. 4, 2021, 5 pages.
Pending U.S. Appl. No. 16/747,219, Response to Mar. 31, 2022 Non-Final Office Action, dated Aug. 1, 2022, 8 pages.
Pending U.S. Appl. No. 16/747,219, Response to May 25, 2023 Non-Final Office Action, dated Aug. 25, 2023, 9 pages.
Pending U.S. Appl. No. 16/747,219, Response to Nov. 10, 2022 Final Office Action, dated Feb. 10, 2023, 6 pages.
Pending U.S. Appl. No. 16/865,031, Final Office Action dated May 24, 2023, 18 pages.
Pending U.S. Appl. No. 16/865,031, Non-Final Office Action dated Nov. 28, 2022, 16 pages.
Pending U.S. Appl. No. 16/865,031, Notice of Allowance dated Oct. 4, 2023, 10 pages.
Pending U.S. Appl. No. 16/865,031, Response to May 24, 2023 Final Office Action, dated Jul. 25, 2023, 8 pages.
Pending U.S. Appl. No. 16/865,031, Response to Nov. 28, 2022 Non-Final Office Action, dated Feb. 27, 2023, 10 pages.
Pending U.S. Appl. No. 16/865,031, Second Preliminary Amendment, filed Sep. 17, 2021, 10 pages.
Pending U.S. Appl. No. 16/865,772, Final Office Action dated Aug. 22, 2022, 18 pages.
Pending U.S. Appl. No. 16/865,772, Final Office Action dated Aug. 4, 2023, 19 pages.
Pending U.S. Appl. No. 16/865,772, Non-Final Office Action dated Apr. 11, 2022, 16 pages.
Pending U.S. Appl. No. 16/865,772, Non-Final Office Action dated Jan. 20, 2023, 17 pages.
Pending U.S. Appl. No. 16/865,772, Response to Apr. 11, 2022 Non-Final Office Action, dated Jul. 11, 2022, 8 pages.
Pending U.S. Appl. No. 16/865,772, Response to Aug. 22, 2022 Final Office Action, dated Dec. 22, 2022, 8 pages.
Pending U.S. Appl. No. 16/865,772, Response to Jan. 20, 2023 Non-Final Office Action, dated Apr. 20, 2023, 8 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 16/915,760, Applicant-Initiated Interview Summary dated Aug. 8, 2023, 2 pages.
Pending U.S. Appl. No. 16/915,760, Final Office Action dated Aug. 10, 2023, 9 pages.
Pending U.S. Appl. No. 16/915,760, Final Office Action dated Jun. 2, 2023, 8 pages.
Pending U.S. Appl. No. 16/915,760, Non-Final Office Action dated Jan. 19, 2023, 8 pages.
Pending U.S. Appl. No. 16/915,760, Notice of Allowance dated Nov. 29, 2023, 7 pages.
Pending U.S. Appl. No. 16/915,760, Response to Aug. 10, 2023 Final Office Action, dated Nov. 10, 2023, 6 pages.
Pending U.S. Appl. No. 16/915,760, Response to Jan. 19, 2023 Non-Final Office Action, dated Apr. 19, 2023, 8 pages.
Pending U.S. Appl. No. 16/915,760, Response to Sep. 20, 2022 Restriction Requirement, filed Nov. 21, 2022, 2 pages.
Pending U.S. Appl. No. 16/915,760, Restriction Requirement dated Sep. 20, 2022, 6 pages.
Pending U.S. Appl. No. 17/000,049, Response to Jul. 31, 2023 Restriction Requirement dated Nov. 9, 2023, 8 pages.
Pending U.S. Appl. No. 17/000,049, Restriction Requirement dated Jul. 31, 2023, 6 pages.
Pending U.S. Appl. No. 17/172,731, Final Office Action dated Jul. 12, 2023, 11 pages.
Pending U.S. Appl. No. 17/172,731, Non-Final Office Action dated Feb. 15, 2023, 7 pages.
Pending U.S. Appl. No. 17/172,731, Non-Final Office Action dated Oct. 31, 2023, 13 pages.
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 162-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.

(56) References Cited

OTHER PUBLICATIONS

Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008, 2 pages.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia, et al., "A Parametric Study Delineating Irreversible Electroporation from Thermal Damage Based on a Minimally Invasive Intracranial Procedure," Biomed Eng Online, vol. 10:34, 22 pages, 2011.
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Garcia-Sanchez, T., A. Azan, I. Leray, J. Rosell-Ferrer, R. Bragos, and L. M. Mir, "Interpulse multifrequency electrical Impedance measurements during electroporation of adherent differentiated myotubes," Bioelectrochemistry, vol. 105, pp. 123-135, 2015.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, EEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed, Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. ii114.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Hu, Q., et al., "Simulations of transient membrane behavior in cells subjected to a high-intensity ultrashort electric pulse", Physical Review E, 71(3) (2005).
(Aycock, Kenneth N. et al.) Co-pending U.S. Appl. No. 17/535,742, filed Nov. 26, 2021, Specification, Claims, and Figures.
(Davalos, Rafael et al.) Co-Pending Application No. PCT/US21/51551, filed Sep. 22, 2021, Specification, Claims, Figures.
(Davalos, Rafael et al.) Co-Pending Application No. PCT/US23/15118, filed Mar. 13, 2023, Specification, Claims, Figures.
(Davalos, Rafael et al.) Co-Pending Application No. PCT/US23/76626, filed Oct. 11, 2023, Specification, Claims, Figures.
(Davalos, Rafael V. et al.) Co-pending U.S. Appl. No. 17/172,731, filed Feb. 10, 2021, Specification, Claims, Figures.
(Davalos, Rafael V. et al.) Co-pending U.S. Appl. No. 17/277,662, filed Mar. 18, 2021, Specification, Claims, Figures.
(Davalos, Rafael V. et al.) Co-pending U.S. Appl. No. 18/027,824, filed Mar. 22, 2023, Specification, Claims, and Figures.

(56) References Cited

OTHER PUBLICATIONS (Davalos, Rafael V. et al.) Co-Pending U.S. Appl. No. 18/130,330, filed Apr. 3, 2023, Specification, Claims, Figures.
(Davalos, Rafael V. et al.) Co-pending U.S. Appl. No. 18/348,605, filed Jul. 7, 2023, Specification, Claims, Drawings.
(Davalos, Rafael V. et al.) Co-pending Application No. 19861489.3 filed Apr. 16, 2021, Specification, figures (See PCT/US19/51731), and claims (3 pages).
(Garcia, Paulo A. et al.) Co-Pending U.S. Appl. No. 18/100,835, filed Jan. 24, 2023, Specification, Claims, Figures.
(Garcia, Paulo A. et al.) Co-pending U.S. Appl. No. 17/591,992, filed Feb. 3, 2022, Specification, Claims, Figures.
(Neal, Robert E. et al.) Co-pending U.S. Appl. No. 18/120,158, filed Mar. 10, 2023, Specification, Claims, Figures.
(Neal, Robert et al.) Co-pending U.S. Appl. No. 18/502,967, filed Nov. 6, 2023, Specification, Claims, Figures.
(Neal, Robert et al.) Co-pending U.S. Appl. No. 17/338,960, filed Jun. 4, 2021, Specification, Claims, Figures.
(Neal, Robert et al.) Co-pending U.S. Appl. No. 18/528,051, filed Dec. 4, 2023, Specification, Claims, Figures.
(O'Brien, Timothy J. et al.) Co-Pending U.S. Appl. No. 17/152,379, filed Jan. 19, 2021, Specification, Claims, Figures.
(Sano, Michael B. et al.) Co-pending U.S. Appl. No. 17/862,486, filed Jul. 12, 2022, Specification, Claims, Figures.
(Sano, Michael B. et al.) Co-pending U.S. Appl. No. 18/123,719, filed Mar. 20, 2023, Specification, Claims, Figures.
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
Alinezhadbalalami, N. et al., "Generation of Tumor-activated T cells Using Electroporation", Bioelectrochemistry 142 (2021) 107886, Jul. 13, 2021, 11 pages.
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Buist et al., "Efficacy of multi-electrode linear irreversible electroporation," Europace, vol. 23, No. 3, pp. 464-468, 2021, 5 pages.
Butikofer, R. et al., "Electrocutaneous Nerve Stimulation-I: Model and Experiment," IEEE Trans. Biomed. Eng., vol. BME-25, No. 6, 526-531, 1978, 6 pages.
Butikofer, R. et al., "Electrocutaneous Nerve Stimulation-II: Stimulus Waveform Selection," IEEE Trans. Biomed. Eng., vol. BME-26, No. 2, 69-75, 1979, abstract only, 2 pages.
Cosman, E. R. et al., "Electric and Thermal Field Effects in Tissue Around Radiofrequency Electrodes," Pain Med., vol. 6, No. 6, 405-424, 2005, 20 pages.
Groen, M. H. A. et al., "In Vivo Analysis of the Origin and Characteristics of Gaseous Microemboli during Catheter-Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4, 329-337, 1976, 9 pages.
Mercadal, B. et al., "Avoiding nerve stimulation in irreversible electroporation: A numerical modeling study," Phys. Med. Biol., vol. 62, No. 20, 8060-8079, 2017, 28 pages.
Mercadal, Borja et al. "Dynamics of Cell Death After Conventional IRE and H-FIRE Treatments", Annals of Biomedical Engineering, vol. 48, No. 5, 2020, p. 1451-1462.
Miklavčič, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol., vol. 31, No. 3, 482-491.e4, Mar. 2020, 19 pages.
Patent No. JP 7051188, Notice of Reasons for Revocation dated Jan. 30, 2023 (3 pages) with English translation (5 pages).
Patent No. JP 7051188, Opposition dated Jul. 4, 2022 (16 pages) with English translation (13 pages).
Patent No. JP 7051188, Response to Jan. 30, 2023 Notice of Reasons for Revocation, dated Apr. 27, 2023 (9 pages) with English translation (10 pages).
Patent No. JP 7051188, Response to Opposition dated Aug. 22, 2023 (21 pages) with English translation (25 pages).
PCT Application No. PCT/US19/51731, International Preliminary Report on Patentability dated Mar. 23, 2021, 13 pages.
Pending U.S. Appl. No. 14/686,380, Advisory Action dated Oct. 20, 2021, 3 pages.
Pending U.S. Appl. No. 14/686,380, Amendment After Board Decision dated Apr. 3, 2023, 8 pages.
Pending U.S. Appl. No. 14/686,380, Appeal Brief filed Nov. 5, 2021, 21 pages.
Pending U.S. Appl. No. 14/686,380, Appeal Decision dated Jan. 30, 2023, 15 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Examiner's Answer to Appeal Brief, dated Feb. 18, 2022, 16 pages.
Pending U.S. Appl. No. 14/686,380, Notice of Non-Compliant Amendment dated May 25, 2023, 3 pages.
Pending U.S. Appl. No. 14/686,380, Reply Brief, dated Apr. 12, 2022, 4 pages.
Zhang, Y., et al., MR imaging to assess immediate response to irreversible electroporation for targeted ablation of liver issues: preclinical feasibility studies in a rodent model. Radiology, 2010. 256(2): p. 424-32.
Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819, 2017.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp 894-899.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.
Boone, K., Barber, D. & Brown, B. Review—Imaging with electricity: report of the European Concerted Action on Impedance Tomography. J. Med. Eng. Technol. 21, 201-232 (1997).

(56) References Cited

OTHER PUBLICATIONS

Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Bulvik, B. E. et al. "Irreversible Electroporation versus Radiofrequency Ablation □: A Comparison of Local and Systemic Effects in a Small Animal Model," Radiology, vol. 280, No. 2, 2016, 413-424.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Castellvi, Q., B. Mercadal, and A. Ivorra, "Assessment of electroporation by electrical impedance methods," in Handbook of electroporation. Springer-Verlag, 2016, pp. 671-690.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W., et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Corovic et al., "Analytical and numerical quantification and comparison of the local electric field in the tissue for different electrode configurations," Biomed Eng Online, 6, 14 pages, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos et al., "Theoretical analysis of the thermal effects during in vivo tissue electroporation." Bioelectrochemistry, vol. 61(1-2): pp. 99-107, 2003.
Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04. 046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap functional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd et al., "Mathematical modeling of irreversible electroporation for treatment planning." Technology in Cancer Research and Treatment, vol. 6, No. 4, pp. 275-286 (2007).
Edd, J., et al., In-Vivo Results of a New Focal Tissue Ablation Technique: Irreversible Electroporaton, IEEE Trans. Biomed. Eng. 53 (2006) p. 1409-1415.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
(Davalos, Rafael V. et al.) Co-pending U.S. Appl. No. 18/402,231, filed Jan. 2, 2024, Specification, Claims, Figures.
(Davalos, Rafael V. et al.) Co-pending U.S. Appl. No. 18/404,473, filed Jan. 4, 2024, Specification, Claims, Figures.
(O'Brien, Timothy J. et al.) Co-Pending U.S. Appl. No. 18/608,958, filed Mar. 19, 2024, Specification, Claims, Figures.

(56) References Cited

OTHER PUBLICATIONS

Bondarenko, A. and G. Ragoisha, Eis spectrum analyser (the program is available online at http://www.abc.chemistry.bsu.by/vi/analyser/) (Accessed Aug. 28, 2020).

Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.

Pending U.S. Appl. No. 16/747,219, Notice of Allowance dated Dec. 26, 2023, 12 pages.

Pending U.S. Appl. No. 17/000,049, Final Office Action dated Mar. 29, 2024, 15 pages.

Pending U.S. Appl. No. 17/000,049, Response to Dec. 11, 2023 Non-Final Office Action, dated Mar. 11, 2024, 9 pages.

Pending U.S. Appl. No. 17/172,731, Response to Oct. 31, 2023 Non-Final Office Action, dated Jan. 31, 2024, 7 pages.

Pending U.S. Appl. No. 17/591,992, Non-Final Office Action dated Feb. 23, 2024, 9 pages.

Pending U.S. Appl. No. 17/591,992, Non-Final Office Action dated Jan. 24, 2024, 7 pages.

Pending U.S. Appl. No. 18/130,330, Second Preliminary Amendment dated Feb. 26, 2024, 3 pages.

Pending U.S. Appl. No. 18/402,231, Preliminary Amendment dated Mar. 5, 2024, 5 pages.

Pending Application No. EP 15793361.5, Communication dated Feb. 8, 2024, 4 pages.

Pending Application No. JP 2016-567747, Decision to Grant with English Version of allowed claims, dated Aug. 26, 2019, 9 pages.

Pending Application No. PCT/US23/76626, Invitation to Pay Additional Fees dated Feb. 21, 2024, 2 pages.

U.S. Appl. No. 14/686,380, file history through Dec. 2023, 265 pages.

U.S. Appl. No. 16/865,772, file history through Aug. 2023, 110 pages.

(Davalos, Rafael V. et al.) Co-pending U.S. Appl. No. 18/767,746) filed Jul. 9, 2024, Specification, Claims, Figures.

Pending U.S. Appl. No. 17/000,049, Examiner Interview Summary dated Jul. 8, 2024, 7 pages.

Pending U.S. Appl. No. 17/152,379, Non-Final Office Action dated Apr. 23, 2024, 14 pages.

Pending U.S. Appl. No. 17/172,731, Notice of Allowance dated Jun. 27, 2027, 7 pages.

Pending U.S. Appl. No. 17/172,731, Response to Apr. 10, 2024 Final Office Action, dated Jun. 10, 2024, 6 pages.

Pending U.S. Appl. No. 17/591,992, Response to Feb. 23, 2024 Non-Final Office Action dated May 23, 2024, 10 pages.

Pending U.S. Appl. No. 18/100,835, Restriction Requirement dated Jun. 28, 2024, 6 pages.

Pending U.S. Appl. No. 18/120,158, Non-Final Office Action dated Jun. 20, 2024, 13 pages.

Pending U.S. Appl. No. 18/404,473, Preliminary Amendment dated May 13, 2024, 6 pages.

Pending U.S. Appl. No. 18/502,967, Non-Final Office Action dated Jun. 18, 2024, 25 pages.

Pending Application No. PCT/US23/76626, International Search Report and Written Opinion, dated Apr. 17, 2024, 12 pages.

Pending U.S. Appl. No. 17/152,379), Response to Apr. 23, 2024 Non-Final Office Action, filed Aug. 23, 2024, 7 pages.

Pending U.S. Appl. No. 17/591,992, Final Office Action dated Jul. 30, 2024, 10 pages.

Pending U.S. Appl. No. 18/120,158, Response to Jun. 20, 2024 Non-Final Office Action, dated Sep. 20, 2024, 8 pages.

Pending U.S. Appl. No. 18/348,605, Non-Final Office Action dated Sep. 5, 2024, 10 pages.

Pending U.S. Appl. No. 18/502,967, Response to Jun. 18, 2024 Non-Final Office Action dated Sep. 18, 2024, 12 pages.

Pending U.S. Appl. No. 18/846,198, Preliminary Amendment dated Sep. 11, 2024, 8 pages.

Pending Application No. EP 15793361.5, Brief Communication from the EPO, dated Aug. 19, 2024, 1 page.

Pending Application No. EP 15793361.5, EPO Result of Consultation, Aug. 12, 2024, 3 pages.

Pending Application No. EP 15793361.5, Response to Feb. 8, 2024 Communication, Filed Aug. 2, 2024, 40 pages.

Pending Application No. EP 15793361.5, Supplemental Response to Feb. 8, 2024 Communication, Filed Aug. 16, 2024, 9 pages.

* cited by examiner

Additional examples of charge-balanced rectangular chirp diagnostic FAST 0.1-0.5-0.1-50 (200 cycles) + 5-1-5-50 (50 cycles)

20-10-20-10 (50 cycles) + 100-10-100-10 (10 cycles)

0.5-1-0.5-50 (500 cycles)+1000-5-1000-5 (1 cycle)

0.5-1-0.5-50 (100 cycles)+1-5-1-50 (20 cycles) + 10-5-10-50 (10 cycles) + 250-10-250-10 (1 cycle)

First round of treatment

Second round of treatment

Example of additional/optional waveforms for FAST

Pulsed Triangular

Pulsed Sawtooth

Pulsed multi-stage

Multisine chirp

Square chirp
(Continuous)

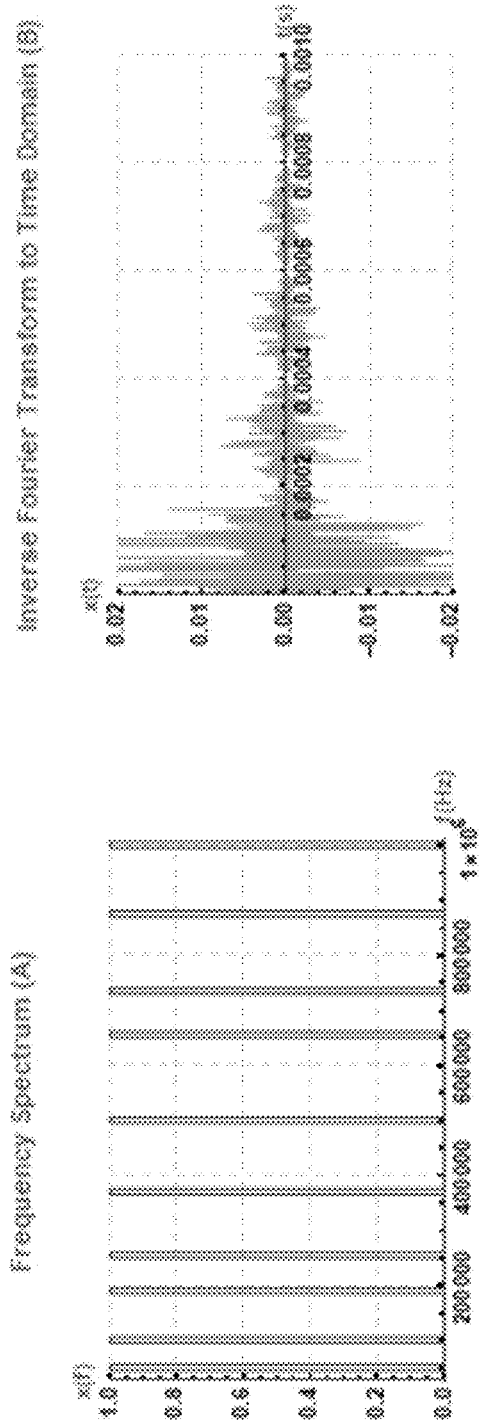
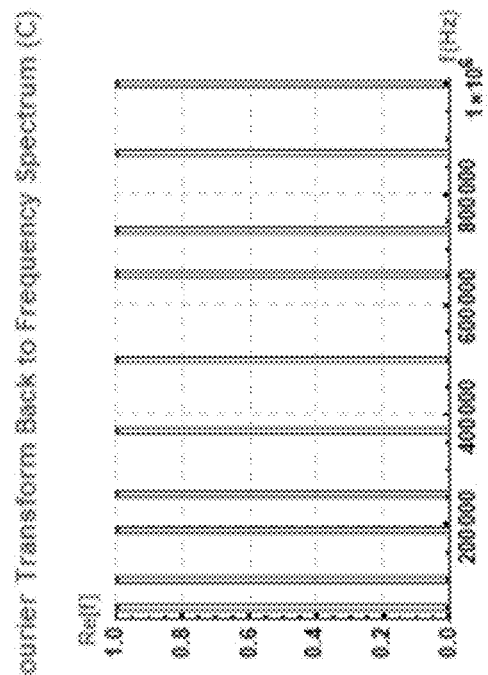
FIG. 19A
FIG. 19B
FIG. 19C

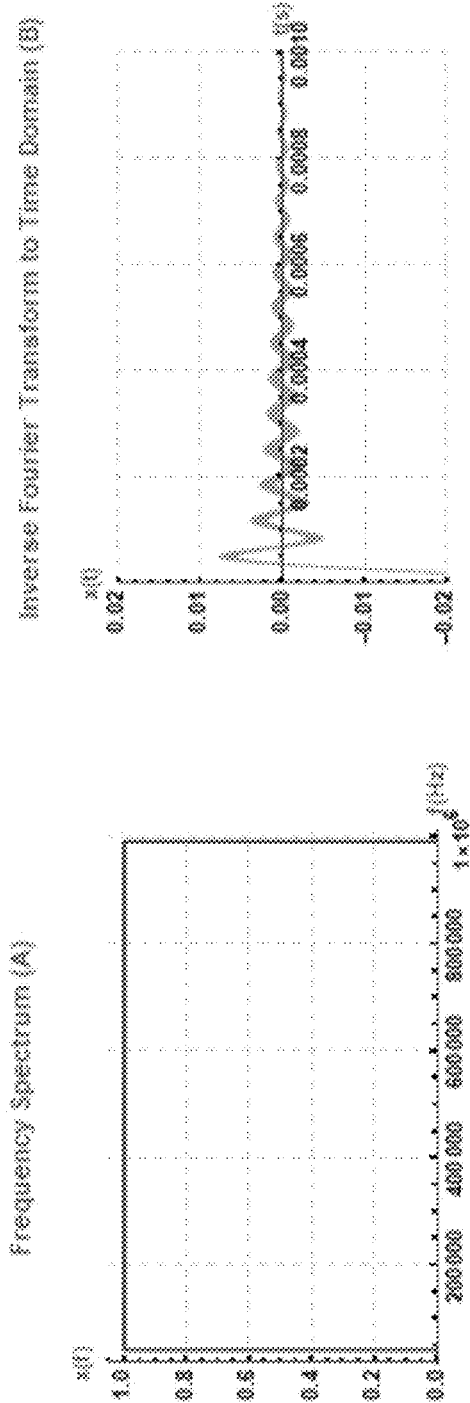
FIG. 20A
FIG. 20B
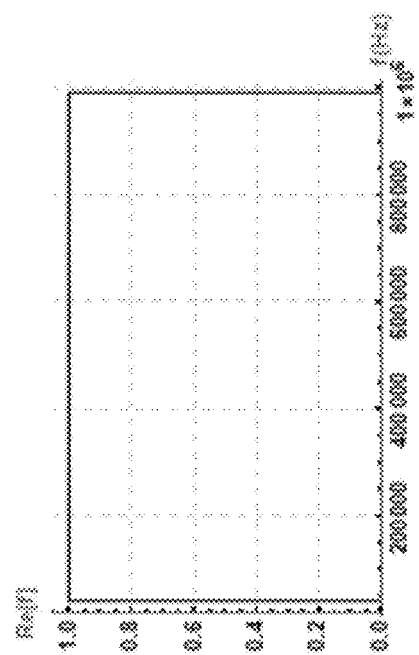
FIG. 20C

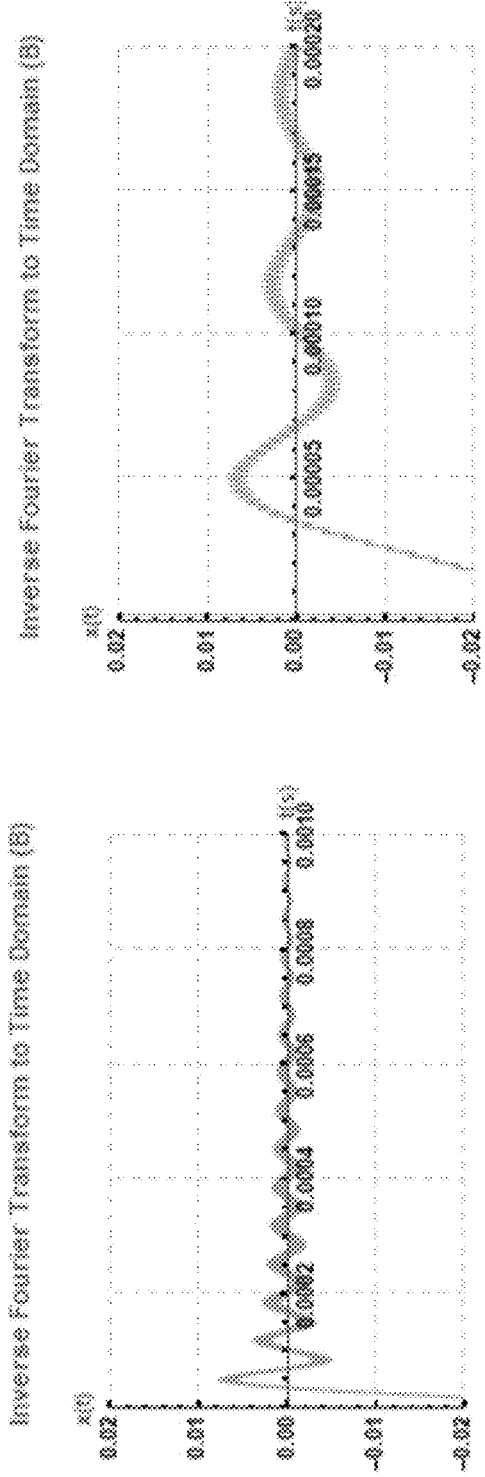
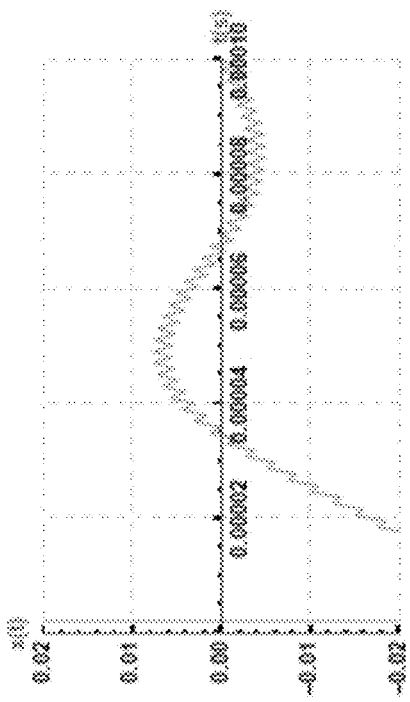
FIG. 21A
FIG. 21B
FIG. 21C

FOURIER ANALYSIS SPECTROSCOPY FOR MONITORING TISSUE IMPEDANCE CHANGES AND TREATMENT OUTCOME DURING ELECTROPORATION-BASED-THERAPIES

CROSS-REFERENCE TO RELATED APPLICATIONS

The present application relies on the disclosure of and claims priority to and the benefit of the filing date of U.S. Provisional Patent Application No. 62/895,652, filed Sep. 4, 2019 and U.S. Provisional Patent Application No. 62/878, 194, filed Jul. 24, 2019, both of which are hereby incorporated by reference herein in their entireties. Additionally, the present application is related to U.S. Pat. Nos. 8,465,484, 8,814,860, 8,926,606, 8,992,517, 9,198,733, 9,283,051, 9,598,691, 9,867,652, 10,117,707, 10,154,874, 10,238,447, 10,245,098, 10,245,105, 10,272,178, 10,286,108, 10,292, 755, 10,448,989, 10,470,822, 10,471,254, 10,537,379, and 10,694,972; U.S. Patent Publication Nos. 2013/0184702, 2015/0289923, 2019/0029749, 2019/0069945, 2020/0093541, 2019/0133671, 2019/0175248, 2019/0175260, 2019/0223938, 2019/0232048, 2019/0233809, 2019/0256839, 2019/0282294, 2019/0328445, 2019/0351224, 2019/0376055, 2020/0046432, and 2020/0197073; International Patent Publication Nos. WO2009/134876, WO2010/118387, WO2010/151277, WO2011/047387, WO2012/0088149, WO2012/071526, WO2015/175570, and WO2020/061192; U.S. patent application Ser. Nos. 13/958, 152, 16/865,031, 16/865,772, and 16/915,760, each of which is incorporated by reference herein in its entirety.

BACKGROUND OF THE INVENTION

Field of the Invention

Treatment options for nonresectable tumors are restricted due to multiple clinical factors, most notably the presence of tumors near critical structures (large blood vessels and nerve bundles), extensive tumor volumes, and/or metastases. Alternate therapies like microwave ablation, radiofrequency ablation, and cryoablation are also limited by tumor location, and thermal therapies are indiscriminate and can easily damage these critical structures. In contrast, electroporation-based therapies (EBTs) are appealing and have proven advantageous for treating or ablating nonresectable tumors due to their nonthermal mechanisms of cell death, which spare proteinaceous structures including nerves and vasculature.

Clinically, EBTs are applied using one or more array of needle electrodes placed in and around the target tissue site. High amplitude (up to 3000 V), short duration (50-100 μs) pulsed electric fields (PEFs) are applied across the electrodes, exposing target tissues to high local field strengths. This results in an increased voltage drop across the cell membrane (transmembrane potential) and gives rise to the creation of defects on the cell membrane. Depending on the pulsing protocol, these defects are either transient or can lead to irrevocable damage.

In a systematic review, electrochemotherapy (ECT), which utilizes reversible electroporation (RE) for enhanced drug delivery, demonstrates an increased overall complete response rate of 59.4% compared to 8.0% with chemotherapy alone, regardless of tumor type. Conversely, irreversible electroporation (IRE) utilizes higher field strengths and increased pulse number to irreversibly disrupt the cell membrane. As the electric fields applied for IRE also encompass fields which generate RE, IRE can be utilized as a combinatorial therapy to ablate a central tumor core with peritumoral RE for enhanced delivery of adjuvant molecular agents. Notably, combinatorial treatment of locally advanced pancreatic cancer with standard-of-care and IRE demonstrated nearly double median overall survival compared to standard-of-care alone. In addition, preclinical trials in a spontaneous canine GBM model have yielded complete responses, demonstrating the effectiveness of IRE as a therapy for intracranial tumors. (Rossmeisl, John H., et al. "Safety and feasibility of the NanoKnife system for irreversible electroporation ablative treatment of canine spontaneous intracranial gliomas." *J. neurosurgery* 123.4 (2015): 1008-1025.)

More recently, a second generation IRE therapy known as High Frequency IRE (H-FIRE) has emerged as an ablation modality that incorporates beneficial aspects of nonthermal ablation improving upon traditional IRE. H-FIRE utilizes bursts of bipolar pulses (~0.5-10 μs) to destabilize cellular membrane structures within the therapeutic field, inhibiting tumor growth. H-FIRE for the treatment of spontaneous intracranial malignancies, for example, is highly efficacious due to compounding effects that alter the highly resistive, invasive, and immunosuppressive environment protecting glioblastoma (GBM) and other brain tumors.

H-FIRE forms a predominantly nonthermal ablation within heterogenous tumors such as GBM, regardless of chemotherapeutic resistance. In addition, prior in vitro studies demonstrate lower therapeutic electric fields are required to induce cell death in malignant brain cell lines compared to healthy brain cell lines, suggesting preferential targeting of malignant phenotypes.

Sub-H-FIRE electric fields are known to cause a reversible electroporation (RE) effect where cells are temporarily permeabilized to larger, normally impermeable chemotherapeutics. In vitro experiments have demonstrated cell-impermeable dye uptake within hours of treatment with RE fields.

Recent investigations have elucidated a long-lived disruption of the blood-brain-barrier (BBB), resulting in enhanced molecular diffusion of impermeable hydrophilic molecules into the brain parenchyma. Finally, recent investigations have elucidated a shift in the tumor microenvironment from immunosuppressive to pro-inflammatory after treatment with an EBT, suggesting that combinatorial H-FIRE and immunotherapy may have a synergistic effect. Thus, tumor ablation with H-FIRE provides multiple avenues for the treatment of non-resectable, highly resistive tumors.

Despite widespread use, EBTs face a unique challenge: intraoperative monitoring of treatment progression towards the determination of a clinical endpoint. Current approaches to determine extent of ablation rely either on postoperative procedures, including imaging with MRI and ultrasound techniques or intraoperative electrical characterization techniques based on a pre-defined change in tissue resistance/current. (W. van den Bos, D. M. de Bruin, A. van Randen, M. R. Engelbrecht, A. Postema, B. Muller, I. Varkarakis, A. Skolarikos, C. Savci-Heijink, R. Jurhill et al., "MRI and contrast-enhanced ultrasound imaging for evaluation of focal irreversible electroporation treatment: results from a phase i-ii study in patients undergoing ire followed by radical prostatectomy," European radiology, vol. 26, no. 7, pp. 2252-2260, 2016.) For example, an absolute change in current/resistance is used to determine a clinical endpoint. The current implementation of this technique, using 50-100 μs IRE/ECT pulses, utilizes direct current (DC) current/ resistance measurements which are highly coupled (electroporation+Joule heating) and would make it impossible to differentiate between electroporation induced changes in impedance and temperature-induced changes in impedance. Here, the inventors provide a method which uses a high-frequency reference, which is not susceptible to electroporation effects (FIGS. 11F-G), to decouple the low-frequency impedance measurements. This allows for thermal impedance changes to be removed and then use the electroporation effects to determine a clinical endpoint. In contrast to EBTs, thermal ablation modalities utilize intraoperative temperature measurements coupled with Arrhenius damage models to predict the treatment volume in real-time. (B. D. de Senneville, C. Mougenot, B. Quesson, I. Dragonu, N. Grenier, and C. T. Moonen, "MR thermometry for monitoring tumor ablation," European radiology, vol. 17, no. 9, pp. 2401-2410, 2007.) Analogous to this approach, proposed methods for EBTs rely on detection of electrical impedance changes as an indicator to EP. The rationale behind using impedance measurements is as follows.

Within the β-dispersion frequency band (~1 kHz-100 MHz), biological tissue can be represented as a 3-domain system, where a high impedance cell membrane separates the intracellular and extracellular spaces. (D. Voyer, A. Silve, L. M. Mir, R. Scorretti, and C. Poignard, "Dynamical modeling of tissue electroporation," Bioelectrochemistry, vol. 119, pp. 98-110, 2018; Q. Castellvi, B. Mercadal, and A. Ivorra, "Assessment of electroporation by electrical impedance methods," in Handbook of electroporation. Springer-Verlag, 2016, pp. 671-690; O. G. Martinsen and S. Grimnes, Bioimpedance and bioelectricity basics. Academic press, 2011.) Prior to electroporation (EP), the intact cell membrane impedes low frequency currents, restricting current flow to the extracellular domain (FIG. 1A). High frequency currents short the membrane reactance, allowing the current to span both intracellular and extracellular domains (FIG. 1B), effectively negating membrane effects. Taken together, biological tissue demonstrates a characteristic impedance spectrum like that shown in FIG. 1D. Alternatively, throughout PEF treatment, permeabilization of the cell membrane causes changes in the impedance either due to decreased membrane resistance and/or exchange of intra- and extracellular ionic content; the integrity of the cell membrane directly impacts the measured electrical impedance spectrum. This change in impedance is the target for monitoring progression of EBTs. Therefore, the recovery of the cell membrane (membrane resealing) can be quantified as this recovery is reflected in the electrical impedance measurements. Cell membrane resealing/recovery is captured as a recovery of the impedance spectrum to its baseline, un-electroporated value.

The analysis of tissue impedance with bursts of bipolar pulses can be characterized into two categories: 1) intra-burst (in-pulse) impedance measurements, the impedance analysis of the EBT waveform, and 2) inter-burst impedance measurements, the impedance analysis at discrete timepoints between therapeutic PEFs. An application for intra-burst impedance has focused on quantifying changes in tissue conductivity during the EBT pulses (N. Beitel-White, S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173; A. Ivorra, B. Al-Sakere, B. Rubinsky, and L. M. Mir, "In vivo electrical conductivity measurements during and after tumor electroporation: conductivity changes reflect the treatment outcome," Physics in Medicine & Biology, vol. 54, no. 19, p. 5949, 2009), aimed towards the creation of accurate pre-treatment planning models (Y. Zhao, S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, no. 8, pp. 1810-1819, 2017; R. E. Neal II, P. A. Garcia, J. L. Robertson, and R. V. Davalos, "Experimental characterization and numerical modeling of tissue electrical conductivity during pulsed electric fields for irreversible electroporation treatment planning," IEEE Transactions on Biomedical Engineering, vol. 59, no. 4, pp. 1076-1085, 2012).

As mentioned previously, inter-burst impedance measurements have been used to gauge the extent of EP. While H-FIRE addresses intricacies associated with current IRE technology (i.e., H-FIRE mitigates muscle excitation, field distortions in heterogenous tissues, and potential cardiac arrythmias), challenges in determining a clinical endpoint with all EBTs still exist. Proposed solutions towards determining a clinical endpoint of EBTs include monitoring changes in bulk tissue impedance/resistance and changes in tissue conductivity distribution. This includes:

1) Electrical impedance tomography (EIT) which utilizes an array of current injection electrodes to reconstruct an impedance map following treatment (R. V. Davalos, D. M. Otten, L. M. Mir, and B. Rubinsky, "Electrical impedance tomography for imaging tissue electroporation," IEEE Transactions on Biomedical Engineering, vol. 51, no. 5, pp. 761-767, 2004; Y. Granot, A. Ivorra, E. Maor, and B. Rubinsky, "In vivo imaging of irreversible electroporation by means of electrical impedance tomography," Physics in Medicine & Biology, vol. 54, no. 16, p. 4927, 2009). EIT has been proposed to monitor impedance changes before and after EBTs to visualize areas impacted by electroporation.

2) Electrical impedance spectroscopy (EIS) either with current carrying electrodes (A. Ivorra and B. Rubinsky, "In vivo electrical impedance measurements during and after electroporation of rat liver," Bioelectrochemistry, vol. 70, no. 2, pp. 287-295, 2007) or with an impedance sensing array (Smart Probe, M. Bonakdar, E. L. Latouche, R. L. Mahajan, and R. V. Davalos, "The feasibility of a smart surgical probe for verification of ire treatments using electrical impedance spectroscopy," IEEE Transactions on Biomedical Engineering, vol. 62, no. 11, pp. 2674-2684, 2015) to measure impedance changes along the length of a single insertion device. Impedance measurements along this impedance sensor array before and after treatment allows for a spatial resolution of tissues impacted by electroporation.

3) Current Density Imaging in conjunction with Bz-based Magnetic Resonance EIT (MREIT) to solve for the electric field distribution and predict cell kill (M. Kranjc, S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, no. 1, pp. 1-10, 2017).

While these technologies have been successful in predicting cell kill in their respective experimental setups, there are limitations in the equipment required to implement these procedures. For example, although these technologies are successful in mapping tissue impedance changes following treatment, there exists difficulties in integrating these technologies with existing pulse generators, there is typically additional cost or expense associated with additional equipment, and the impedance spectrum acquisition timeframe (~10 s) is typically much larger than that between pulse periods (~1 s) used with EBTs.

Here, the present inventors introduce Fourier Analysis SpecTroscopy (FAST) as an impedance spectroscopy methodology for monitoring tissue impedance changes during EBTs in real-time. Specifically, the development of both diagnostic FAST, aimed towards monitoring inter-burst impedance, and therapeutic FAST, aimed towards inducing tissue EP while simultaneously monitoring high voltage intra-burst tissue impedance (FIG. 1D) are discussed. Diagnostic FAST is achieved by delivering a low-voltage, wideband signal composed of rectangular bipolar pulses; voltage and current capture followed by discrete Fourier transform for analysis in the frequency domain allows for real-time EIS with wide frequency bands. Therapeutic FAST is achieved by delivering a high-voltage burst of bipolar PEFs; therapeutic FAST is an adaptation of a traditional high-frequency IRE burst, modified to maximize the frequency bandwidth and resolution to enable intra-burst impedance spectroscopy. Impedance analysis with therapeutic FAST is distinguished from diagnostic FAST as diagnostic FAST measures impedance following significant pore resealing and membrane recovery, while investigations from therapeutic FAST theoretically incorporate impedance change during pore formation and pore expansion.

DESCRIPTION OF RELATED ART

To this end, methods for rapid bioimpedance measurements have been previously proposed. In summary, rapid EIS measurements are dependent on applying low-voltage or low-current stimulus, subsequent Fourier Transform, followed by analysis in the frequency domain. Above all else, these methods should be performed to minimize inclusion of significant nonlinearities (membrane resealing). Several stimulation signals have been proposed, including multisine waves (B. Sanchez, G. Vandersteen, R. Bragos, and J. Schoukens, "Optimal multisine excitation design for broadband electrical impedance spec-troscopy," Measurement Science and Technology, vol. 22, no. 11, p. 115601, 2011), Gaussian pulses (M. Min, U. Pliquett, T. Nacke, A. Barthel, P. Annus, and R. Land, "Broadband excitation for short-time impedance spectroscopy," Physio-logical measurement, vol. 29, no. 6, p. S185, 2008), rectangular chirps (M. Min, A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88), maximum length binary sequences (S. Gawad, T. Sun, N. G. Green, and H. Morgan, "Impedance spectroscopy using maximum length sequences: Application to single cell analysis," Review of Scientific Instruments, vol. 78, no. 5, p. 054301, 2007), and white-noise (S. C. Creason, J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, no. 1, pp. 9-46, 1973). Particularly in the field of electroporation, only modest works have been conducted to investigate inter-burst impedance changes throughout the entirety of treatment.

Previously, García-Sánchez et al. proposed utilization of a multi-sine burst for impedance analysis between 5 kHz to 1.313 MHz at 21 discrete frequencies. (T. García-Sánchez, A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.) Preference to using rectangular waveforms, over sinusoidal excitation signals (B. Sanchez, G. Vandersteen, R. Bragos, and J. Schoukens, "Basics of broadband impedance spectroscopy measurements using periodic excitations," Measurement Science and Technology, vol. 23, no. 10, p. 105501, 2012), is such that rectangular waveforms are easily integrated into existing pulse generator topologies for EBTs as the pulse widths implemented are similar to those delivered with nanosecond PEFs, high-frequency bipolar PEFs, and monopolar PEFs. Ultimately, the inventors aim to minimize the excitation of cardiomyocytes, skeletal muscle fibers, and nerve fibers during impedance characterization with diagnostic FAST; for example through the use of a charge balanced bipolar chirp waveform, the stimulation of excitable tissues will be kept to a minimum. This would further extend applicability into techniques such as cardiac ablation. FAST introduces a novel application of high-frequency tissue impedance measurements as an indicator of the extent of Joule heating effects during EP. Although low-frequency impedance measurements are sensitive to both EP effects and Joule heating, the inventors have found that high frequency currents, which short the membrane reactance, are less sensitive to EP effects and can uniquely act to distinguish thermal effects (FIGS. 1A-D).

Previously, the inventors utilized a Fourier analysis to quantify intra-burst impedance changes during H-FIRE therapy. (S. Bhonsle, M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, no. 10, pp. 2190-2201, 2017.) By fitting the resulting data to a dispersive parallel RC (resistance and capacitance) tissue model, this technique allowed for quantifying the ex vivo porcine tissue conductivity/permittivity response at varying applied electric fields with an end goal directed towards pre-treatment planning. The goal was to show that the electric field distribution was more homogenous by determining the conductivity function for predicting the electric field.

Here, the inventors' initial findings are extended to develop diagnostic FAST for monitoring inter-burst electrical impedance spectra directed towards monitoring treatment outcome with EBTs and therapeutic FAST for monitoring intra-burst impedance directed towards characterizing biological tissue response during EP. Their findings suggest acquisition of an impedance spectrum (~0.1 kHz-100 MHz), such as a high-bandwidth inter-burst impedance spectrum (between 1.8 kHz-4.93 MHz) and intra-burst impedance spectrum (between 18.3 kHz-1.96 MHz) is possible at >100 discrete frequencies per spectrum and at a capture rate <<1 s. Through the modification of existing H-FIRE waveforms, the inventors demonstrate bipolar pulse schemes of pulse width 1 µs-1 ms enable FAST to capture electrical impedance content at frequencies between 1 kHz-5 MHz. This technique not only enables real-time EIS but allows for novel applications for high-frequency impedance as a parameter to delineate thermal effects from that of EP during EBTs. FAST technologies can be used to monitor EBT treatment outcomes (e.g., when an expected endpoint of treatment has been reached and/or the success of a treatment, such as whether the desired ablation effect has been achieved), EBT treatment progress, and/or detect or warn of thermal effects. FAST technologies are especially suited to provide for such monitoring in real-time during an EBT treatment, which can be very helpful in knowing when to alter treatment parameters, or when to halt treatment temporarily (such as to avoid excess temperatures), or when to stop treatment completely.

SUMMARY OF THE INVENTION

Embodiments of the invention include Aspect 1, which is a method for monitoring administration of electrical pulses comprising: obtaining a baseline impedance spectrum; administering a plurality of electrical pulses; obtaining one or more additional impedance spectrum; identifying any impedance spectrum change relative to the baseline; and monitoring the administering to determine if a desired endpoint is reached as indicated by the impedance spectrum change, and i) adjusting one or more parameters of, ii) stopping, iii) halting, and/or iv) continuing the administering based on the monitoring.

Aspect 2 is the embodiment of Aspect 1, wherein the endpoint for irreversible electroporation is a point during the administering where electroporation no longer contributes to any impedance spectrum change as evidenced by the obtaining of a flat impedance spectrum.

Aspect 3 is the method of Aspect 1 or 2, further comprising halting the administering to allow tissue temperature to reach a desired level, then resuming the administering to the desired endpoint.

Aspect 4 is the method of any of Aspects 1-3, comprising: delivering a low-voltage, wideband signal of electrical pulses; and monitoring treatment outcome through monitoring inter-burst impedance by capturing voltage and current and performing discrete Fourier transform analysis.

Aspect 5 is the method of any of Aspects 1-4, wherein impedance is captured within a frequency range of above 0.1 kHz to 100 MHz, such as between 1.8 kHz and 4.93 MHz.

Aspect 6 is the method of any of Aspects 1-5, wherein delivering of the electrical pulses comprises applying one or more low-voltage pulses interleaved between one or more high-voltage pulses.

Aspect 7 is the method of any of Aspects 1-6, wherein delivering of the electrical pulses comprises applying pulses in the range of 0.1 μs to 10 ms, such as at a high frequency signal of 1-50-1-50 μs, appended to a low frequency signal of 250-10-250-10 μs.

Aspect 8 is the method of any of Aspects 1-7, further comprising: delivering one or more high-voltage burst of pulsed electric fields; and monitoring tissue response through monitoring high-voltage intra-burst impedance by capturing voltage and current and performing discrete Fourier transform analysis.

Aspect 9 is the method of any of Aspects 1-8, wherein impedance is captured within a frequency range of above 0.1 kHz to 100 MHz, such as between 18.3 kHz and 1.96 MHz.

Aspect 10 is the method of any of Aspects 1-9, wherein the delivering comprises a high-frequency irreversible electroporation burst scheme of pulse width and intra-phase delay ranging from 0.1 μs to 10 ms, and inter-pulse delay ranging from 0.1 μs to 1 s, such as delivering high-frequency irreversible electroporation using a 2-5-2 μs scheme, followed by a 100 μs delay.

Aspect 11 is the method of any of Aspects 1-10, wherein the baseline impedance spectrum and/or the additional impedance spectrum is obtained by one or more of: reference to an impedance spectrum based on standard impedance values for a particular material or tissue; measuring impedance of a material or tissue over a selected frequency band; measuring voltage and/or current and calculating impedance therefrom; and/or calculating impedance as a function of frequency using the formula:

$$Z(f) = \frac{V(f)}{I(f)},$$

wherein: Z is impedance; V is voltage; and I is current.

Aspect 12 is the method of any of Aspects 1-11, further comprising using the impedance spectrum change measured at high frequencies to predict a temperature change, such as in tissue, relating to the administering of the electrical pulses.

Aspect 13 is the method of any of Aspects 1-12, wherein the impedance spectrum change indicates one or more of: whether irreversible or reversible electroporation of a tissue has, is or will occur; whether chemical cell death and/or decellularization has, is or will occur; whether death and/or decellularization has, is or will occur due to a physical disruption; whether a tissue is healthy or cancerous; whether a tissue has damage from a stroke and/or traumatic brain injury; whether cell lysis has, is or will occur as evidenced by flattening of the impedance spectrum with no recovery following pulse cessation; whether cell necrosis has, is or will occur as evidenced by flattening of the impedance spectrum with minimal recovery following pulse cessation; and/or whether cell apoptosis has, is or will occur as is evidenced by flattening of the impedance spectrum with moderate recovery following pulse cessation.

Aspect 14 is the method of any of Aspects 1-13, wherein the change in the impedance indicates: whether degradation of a coating has, is or will occur; and/or whether a coating of a material has corrosion and/or a level of the corrosion.

Aspect 15 is the method of any of Aspects 1-14, wherein the monitoring comprises: monitoring tissue decellularization and/or cell death; monitoring gene-transfection efficiency and uptake; monitoring thermal and/or non-thermal tissue ablation for cardiac arrythmias; and/or monitoring cell lysis for immunotherapies.

Aspect 16 is a treatment monitoring system for administering electrical pulses comprising: one or more electrical pulse generator(s); one or more probe(s) capable of connection with the electrical pulse generator(s); one or more controller(s) capable of controlling one or more of the electrical pulse generator(s) and/or one or more of the probe(s) to: administer a plurality of electrical pulses; obtain a baseline impedance spectrum; obtain one or more additional impedance spectrum; and identify any impedance spectrum change relative to the baseline.

Aspect 17 is the treatment monitoring system of any of Aspect 16, further comprising a processing module with a processor in combination with memory and computer-executable instructions configured to process the impedance spectra using a Fourier Transform algorithm.

Aspect 18 is the treatment monitoring system of Aspect 16 or 17, wherein: one or more of the pulse generator(s) is capable of delivering high-voltage pulses; and one or more of the pulse generator(s) is capable of delivering low-voltage pulses.

Aspect 19 is a treatment monitoring system (such as that of any of Aspects 16-18), wherein: one or more controller(s) is a microcontroller capable of connection with: a first 5V H-Bridge circuit for connection with a high-voltage pulse generator; a 15V H-Bridge circuit for connection with a low-voltage pulse generator; and a second 5V H-Bridge circuit for connection with two Reed relays on a high-voltage circuit (HVRR) and two Reed relays on a low-voltage circuit (LVRR); wherein the microcontroller is capable of: triggering the Reed relays on the low-voltage circuit to close; triggering the low-voltage generator to deliver pulses; ceasing the LVRR trigger signal to open the LV and HV circuits; triggering the HVRR Reed relays on the high-voltage circuit to close; triggering the high-voltage generator to deliver pulses.

Aspect 20 is the treatment monitoring system of any of Aspects 16-19, wherein one or more of the controller(s) is capable of i) adjusting one or more parameters of, ii) stopping, iii) halting, and/or iv) continuing the triggering of the low-voltage and/or high-voltage generators based on the impedance spectrum change.

Aspect 21 is a system comprising: one or more probe(s) providing functionality for: delivering a plurality of electrical pulses to a tissue; and measuring electrical impedance relating to the tissue; wherein the functionality is on the same probe or different probes; an impedance analyzer coupled to one or more of the impedance measuring probes; a low voltage power supply and a high voltage power supply coupled to one or more of the probes and configured to deliver a low voltage and/or high voltage energy to the probe(s); one or more waveform generator coupled to one or more of the probes and the low and/or high voltage power supplies; and one or more switch coupled to the low voltage and high voltage power supplies, and configured to perform the delivering of the plurality of electrical pulses in the form of low voltage pulses and/or high voltage pulses, and configured to enable switching between HV and LV.

BRIEF DESCRIPTION OF THE DRAWINGS

The accompanying drawings illustrate certain aspects of embodiments of the present invention, and should not be used to limit the invention. Together with the written description, the drawings serve to explain certain principles of the invention.

FIGS. 19A-C are graphs showing wide-bandwidth waveform definition for FAST data acquisition, including a defined frequency spectrum (FIG. 19A); an inverse Fourier Transform of the frequency domain signal to obtain the desired time domain waveform (FIG. 19B); return to the defined frequency spectrum by taking the Fourier Transform of the time domain signal (FIG. 19C).

FIGS. 20A-C are graphs showing the wide-bandwidth waveform definition for FAST data acquisition, including the defined frequency spectrum (FIG. 20A); the inverse Fourier Transform of the frequency domain signal to obtain the desired time domain waveform (FIG. 20B); and return to the defined frequency spectrum by taking the Fourier Transform of the time domain signal (FIG. 20C).

FIGS. 21A-C are graphs depicting zoomed in data for FIG. 20B, with FIG. 21A showing 0-0.001 s; FIG. 21B showing 0-0.0002 s; and FIG. 21C showing 0-0.0001 s.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Definitions:

The term "pulse" refers to an electrical signal with a single phase (monopolar, unipolar) or more than one phase (bi-polar). If bi-polar, there can be a delay between phases or the switch between phases can be immediate (no intra-pulse delay).

The term "burst" refers to a set of pulses, a group of pulses, or a pulse group.

The term "intra-pulse delay" refers to the condition where no energy is applied for a period of time during the bipolar pulses.

The term "inter-pulse delay" refers to the condition where no energy is applied for a period of time between one bipolar pulse or set of bipolar pulses and another bipolar pulse.

The term "intra-burst delay" refers to the condition where no energy is applied for a period of time between one or more bursts.

The term "inter-burst delay" refers to the condition where no energy is applied for a period of time within a burst and in some cases may be the same as an intra- or inter-pulse delay.

Figure 22:
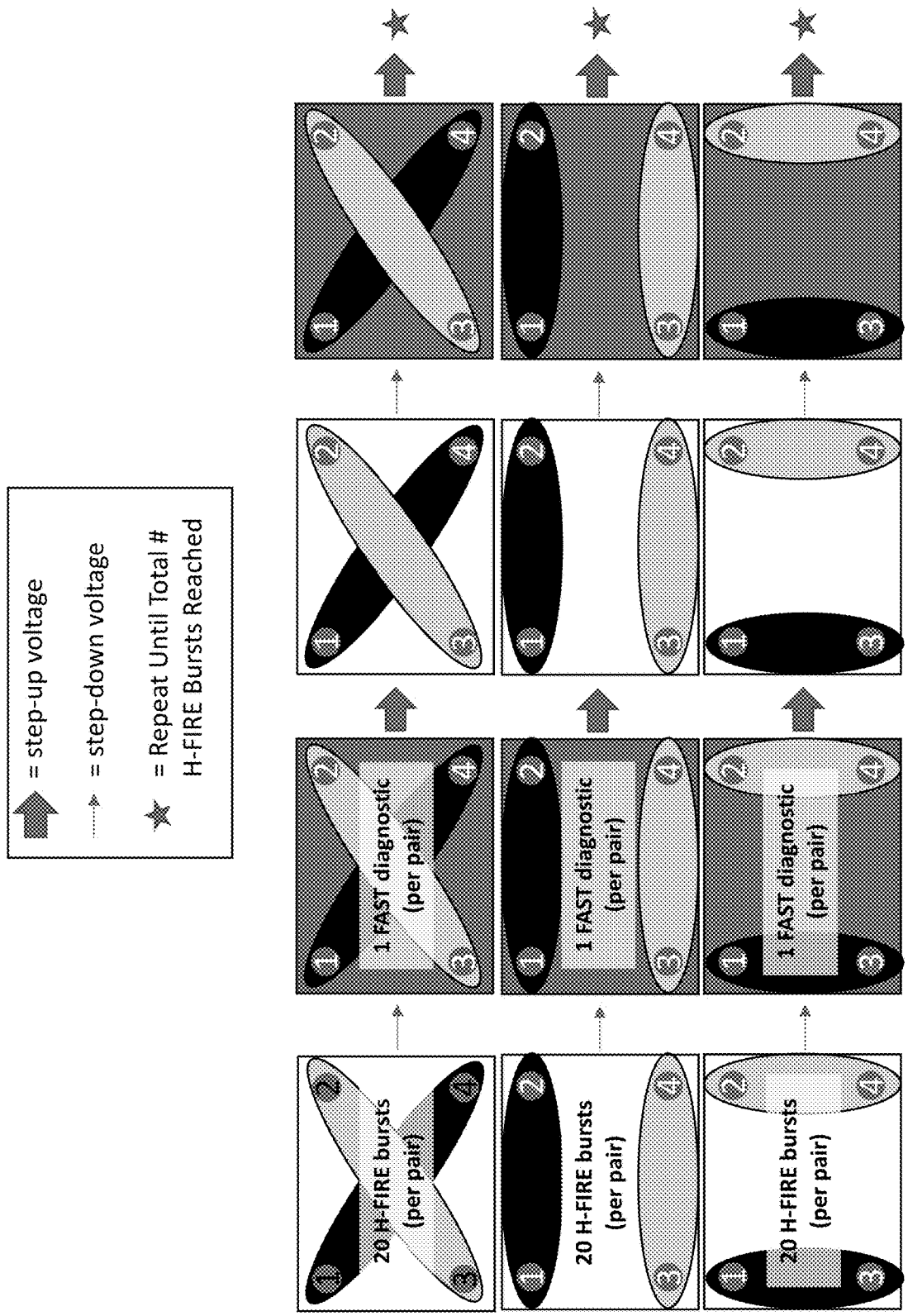
FIG. 22 is a diagram depicting a 4-probe array for a "cycled pulsing" FAST protocol.

The term "cycled pulsing scheme" or "cycles" refers to a pulse scheme in which the total number of pulses are delivered over more than one cycle. The total number of pulses per cycle is calculated by dividing the total number of desired pulses by the number of cycles. The term may be used interchangeably with "cycled pulsing protocol," "cycled pulsing sequence," "cycled pulsing," "cycled pulsing paradigm," "cycled pulsing embodiment," "cycled pulse sequencing," "cycled pulse paradigm," or "cycled pulsing pattern." For example, a cycled pulsing scheme is shown in FIG. 22.

The term "total on time" or "combined signal duration" or "energized time" refers to the time associated with energizing an electrode. For example, a single 1-50-1-50 µs burst scheme would have a total on time of 2 µs for each burst, whereas a 250-10-250-10 µs burst would have a total on time of 500 µs for each burst.

The term "pulse protocol" or "pulsing scheme" or "pulsing protocol" or "pulse scheme" refers to a protocol defined by any one or more of or all of the following: the number of pulses; the duration of each pulse; any inter-pulse, intra-pulse, inter-burst, or intra-burst delay; the number of bursts; and the number of cycles, if applicable.

The term "saturation" refers to an impedance measurement or spectrum matching or converging with another impedance measurement or spectrum. For example, low frequency impedance can be monitored for saturation to the high frequency impedance, meaning a low frequency impedance measurement can be taken and compared with a previous baseline and/or reference high frequency impedance measurement.

Embodiments of the invention provide a Fourier Analysis SpecTroscopy (FAST) technique as an impedance spectroscopy methodology for monitoring impedance changes in a material or tissue, such as during electroporation-based therapies (EBTs) in real-time. Included within embodiments are a diagnostic FAST methodology and a therapeutic FAST methodology.

The term "diagnostic FAST" refers to a pulse scheme designed for monitoring inter-burst impedance of a material or tissue, such as during EBTs, including IRE and/or H-FIRE treatments. Diagnostic FAST can be achieved by delivering a low-voltage (0 V to 100 V), wideband signal (e.g., comprising rectangular bipolar pulses) and performing voltage and current capture followed by discrete Fourier transform for analysis in the frequency domain. Diagnostic FAST can be applied prior to treatment, to determine the impedance spectrum of the tissue in an intact state, during treatment in between high voltage pulses, to continually monitor changes in impedance due to electroporation pulses, immediately after treatment to measure the final state of the tissue, and in the time following treatment to measure the recovery of the cell membrane and recovery of the impedance spectrum. This will be described in more detail below.

In embodiments, the low-voltage electrical pulses/bursts can be applied using a voltage of above 0 V to 100 V, such as up to 10 V, up to 15 V, up to 20 V, up to 30 V, up to 40 V, up to 50 V, up to 60 V, up to 70 V, up to 80 V, up to 90 V, or from 5-85 V, or from 12-55 V, or from 35-75 V, or from 15-45 V, or any range in between any of these ranges or endpoints, including as endpoints any number encompassed thereby. Additionally, although rectangular pulses are more typical, the signal can comprise a waveform with any step, square, sinusoidal, ramp, Gaussian, or sinc function having constant, increasing, or decreasing frequency, or any arbitrary signal designed to achieve a desired frequency spectrum, such as in the range of 0.1 kHz to 100 MHz.

Diagnostic FAST comprises a pulse protocol (typically administering at a low-voltage) constructed by concatenating a high-frequency signal to low-frequency signal to form the final waveform: positive phase–intra-phase delay–negative phase–inter-pulse delay+positive phase–intra-phase delay–negative phase–inter-pulse delay. The set of high-frequency signal(s) (comprising: positive phase–intra-phase delay–negative phase–inter-pulse delay) can be delivered first or after the low-frequency signal(s) (comprising: positive phase–intra-phase delay–negative phase–inter-pulse delay). For example, the pattern can be a set of high-frequency signal(s)+a set of low-frequency signal(s), or low-frequency signal(s)+high frequency signal(s). If desired, multiple pulses, such as rectangular bipolar pulse signals, can be concatenated to form a continuous chirp like that in FIG. 18 "Square Chirp Continuous". The signals can be concatenated in any order, and can be the same or different type, phase, and/or amplitude.

The term "therapeutic FAST" refers to a pulse scheme designed to induce tissue EP while monitoring high voltage intra-burst impedance changes in real time. Therapeutic FAST can be achieved by delivering a high-voltage (100 V to 15,000 V) burst of bipolar PEFs and is an adaptation of a traditional high-frequency IRE burst, modified to maximize the frequency bandwidth and resolution to enable intra-burst impedance spectroscopy. In embodiments, the high-voltage electrical pulses/bursts can be applied using a voltage of 100 V to 15,000 V, such as from 500 V up to 3,000 V, and/or from 1,000 V up to 2,000 V, such as up to 250 V, up to 300 V, up to 350 V, up to 600 V, up to 650 V, up to 800 V, up to 1,200 V, up to 1,500 V, up to 15,000 V, up to 7,500 V, from 4,000 V to 12,000 V, or any range in between any of these ranges or endpoints, including as endpoints any number encompassed thereby. In embodiments, the electrical pulses can be administered using a frequency ranging from 100 Hz to 100 MHz, such as in the Hz range from 100 Hz or 1 Hz up to 100 Hz, or from 2 Hz to 100 Hz, or from 3 Hz to 80 Hz, or from 4 Hz to 75 Hz, or from 15 Hz to 80 Hz, or from 20 Hz to 60 Hz, or from 25 Hz to 33 Hz, or from 30 Hz to 55 Hz, or from 35 Hz to 40 Hz, or from 28 Hz to 52 Hz, or any range in between any of these ranges or endpoints, including as endpoints any number encompassed thereby. Additionally, pulses can be administered using a frequency in the kHz or MHz range, such as from 1 kHz to 10 kHz, or from 2 kHz to 8 kHz, or from 3 kHz to 5 kHz, or from 4 kHz to 15 kHz, or from 6 kHz to 20 kHz, or from 12 kHz to 30 kHz, or from 25 kHz to 40 kHz, or from 5 kHz to 55 kHz, or from 50 kHz to 2 MHz, including any range in between, such as from 75 kHz to 150 kHz, or from 100 kHz to 175 kHz, or from 200 kHz to 250 kHz, or from 225 kHz to 500 kHz, or from 250 kHz to 750 kHz, or from 500 kHz to 1 MHz, or any range in between any of these ranges or endpoints, including as endpoints any number encompassed thereby.

FAST schemes can be employed to measure the electrical impedance of testing loads which include, but are not limited to, biological tissues. The bandwidth (frequency limits) and the resolution (number of data points within the bandwidth) of the obtained FAST impedance spectrum are dependent on the pulsing schemes applied to the tissue. The characteristic frequency of each burst scheme determines the lowest frequency at which impedance data is attained, the characteristic frequency being defined as:

$$f_{char}=1/(2*\text{pulse width}[\mu s]+\text{intra-phase delay}[\mu s]+\text{interpulse delay}[\mu s]) \text{ kHz}.$$

Therefore, pulsing parameters can be modified to a user-desired frequency bandwidth. A method to verifying frequency content entails taking the Fourier Transform and identifying the high-power signal in the frequency spectrum. The high-power signal is processed, and these frequencies constitute the frequencies at which impedance capture is possible.

Fourier Analysis SpecTroscopy (FAST) can be used as a methodology utilizing modified EBT waveforms to conduct low voltage inter-burst (diagnostic FAST) and high-voltage intra-burst (therapeutic FAST) impedance spectroscopy. Diagnostic FAST is the state of the tissue following pore resealing, while therapeutic FAST is a snapshot of the impedance during the pulse, a state when the pores are forming/formed.

Figure 3A:
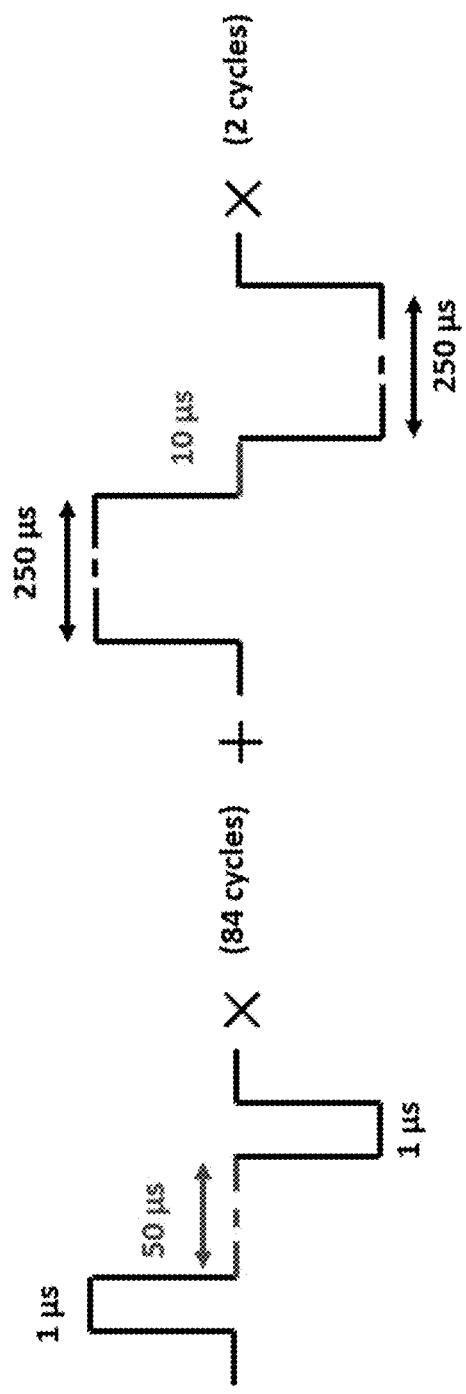
FIGS. 3A-B are diagrams of representative diagnostic and therapeutic FAST schemes, including a diagnostic FAST scheme comprising a 1-50-1-50 µs burst scheme (84 cycles) appended to a 250-10-250-10 µs (2 cycles) for a total signal duration <10 ms (FIG. 3A), and a therapeutic FAST scheme comprising a 2-5-2 µs H-FIRE scheme, modified to 2-5-2-100 µs incorporate a 100 µs extended delay after a set of bipolar pulses (FIG. 3B).
Figure 4A:
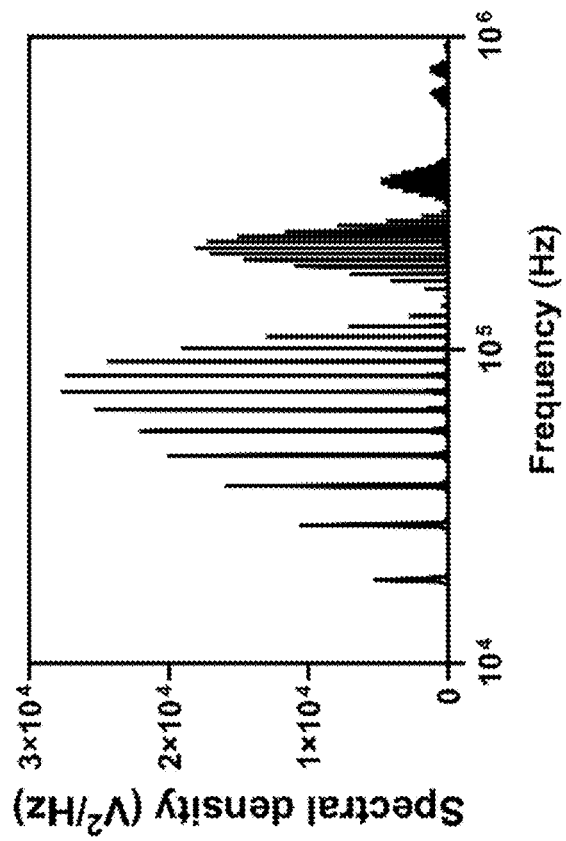
FIGS. 4A-B are graphs depicting the power spectral density of the MATLAB developed ideal voltage waveforms.

For example, a 1-50-1-50+250-10-250 µs diagnostic FAST burst scheme can be used to measure frequencies ranging from above 0.1 kHz to 100 MHz, such as between ~2 kHz-5 MHz (FIG. 3A), which exhibit high frequency content (i.e., high resolution) at low and high frequencies ranging from ~2 kHz to 5 MHz (FIG. 4A). This particular burst scheme, 1-50-1-50+250-10-250 µs, is not meant to be restrictive or meant to limit the signal variations for FAST. The pulse width and/or the width of inter-pulse, intra-pulse, inter-burst, and/or intra-burst delays can be selected/modified to comply with other treatment-specific requirements. A diagnostic FAST scheme can be used at any point during treatment, for example, before, during, after high-voltage pulsing, such as immediately after consecutive pulsing.

Figure 3B:
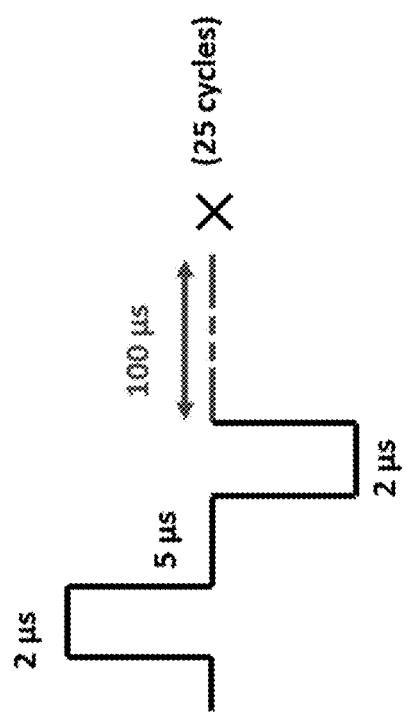

A therapeutic FAST/H-FIRE burst scheme can be used to ablate and capture impedance information with FAST, for example simultaneously. A 2-5-2-100 µs pulse protocol can be used as the therapeutic FAST scheme, with changes in tissue impedance being monitored preferably in real-time (FIG. 3B). This particular therapeutic FAST scheme (2-5-2-100 µs) shows high resolution extending up to ~ 2 MHz (FIG. 4B), yet other pulsing protocols can also be used. Although lower resolution spectra can be used in some applications, higher resolution results typically will provide the user/practitioner with a greater confidence level relating to the treatment (e.g., a greater confidence level that a particular outcome or effect has been achieved or is occurring during treatment). Like H-FIRE, the pulse width can be modified, for example, to include: 1) 1-5-1--100 µs, 2) 5-5-5--100 µs, 3) 10-5-10--100 µs, the intra-phase delay can also be modified to include, for example: 1) 2-1-2--100 µs, 2) 2-10-2--100 µs, 3) 2-100-2--100 µs, as well as the inter-pulse delay, which can for example include: 1) 2-5-2--1 µs, 2) 2-5-2--10 µs, 3)[-]]2-5-2--100 µs. Pulse width can be in the range of for example 0.1 µs to 10 ms.

Figure 18:
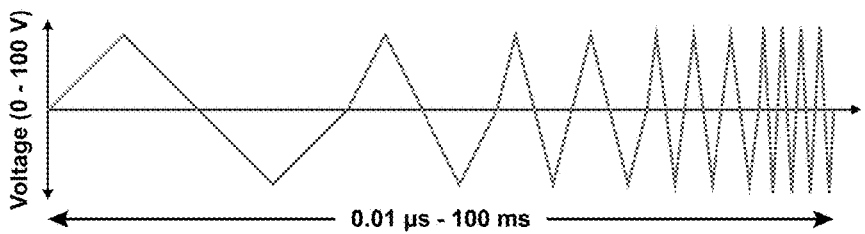
FIG. 18 is a schematic showing an embodiment of the invention using various FAST waveforms, including pulsed triangular, pulsed sawtooth, pulsed multi-stage, multisine bursts, and square waveforms with voltages ranging from 0 V-100 V and pulse lengths of up to 100 ms.
Figure 18:
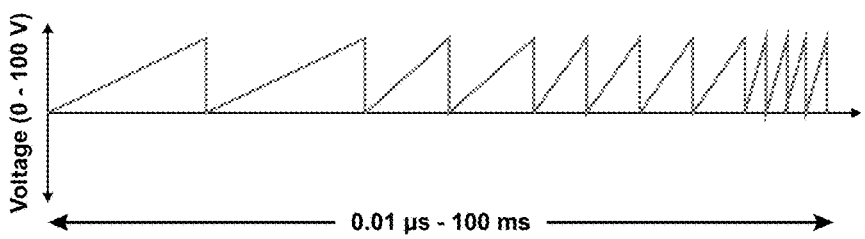
Figure 18:
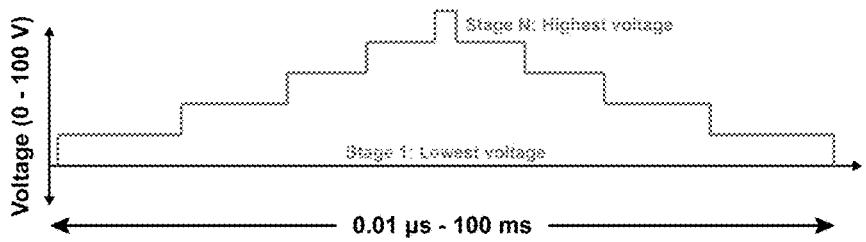
Figure 18:
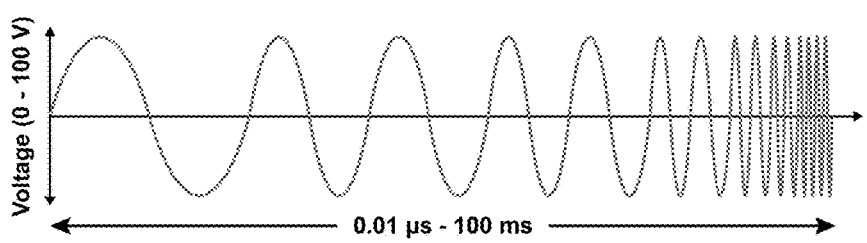
Figure 18:
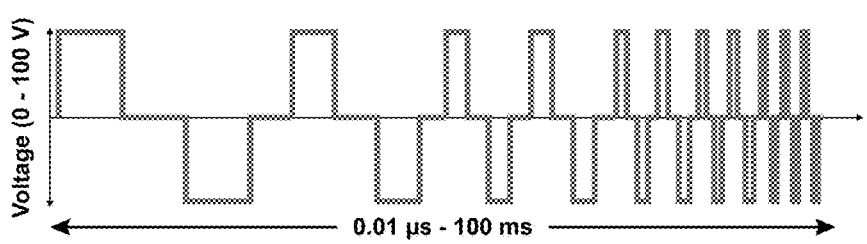

Non-square waveforms (i.e. pulsed triangular waveforms, continuous sawtooth waveforms, multisine bursts, and/or multistage waveforms—FIG. 18) can be used to measure inter-burst impedance with FAST. In embodiments, the waveform can comprise any step, square, sinusoidal, ramp, Gaussian, or sinc function having constant, increasing, or decreasing frequency, or any arbitrary signal designed to achieve a desired frequency spectrum in the range of above 0.1 kHz to 100 MHz. Additionally, diagnostic FAST can be used for a pulse sequence that does not include an intra-pulse delay (e.g., instant charge reversal, or a pulse with no delay between changing from negative to positive polarity).

Figure 7A:
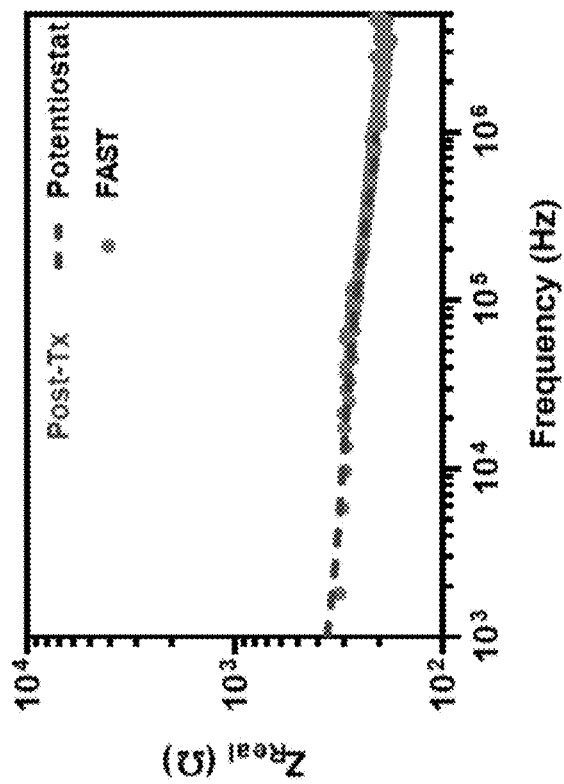
FIGS. 7A-B are graphs comparing diagnostic FAST and a commercial potentiostat to measure bulk potato impedance before (FIG. 7A) and after (FIG. 7B) IRE pulses.
Figure 7B:
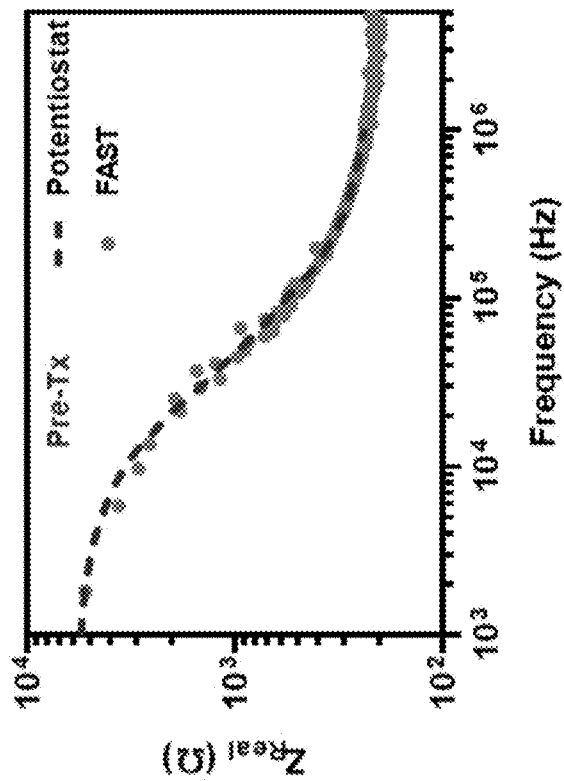
Figure 7D:
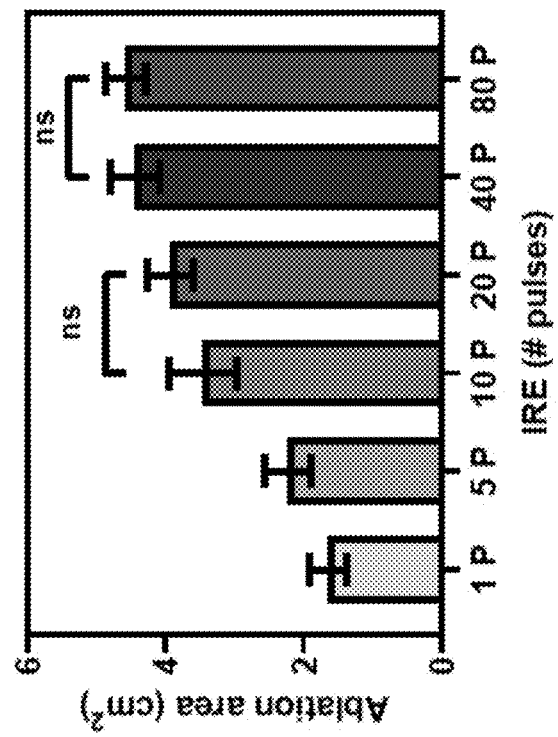
FIG. 7D is a graph showing ablation areas after administration of IRE pulses.
Figure 7C:
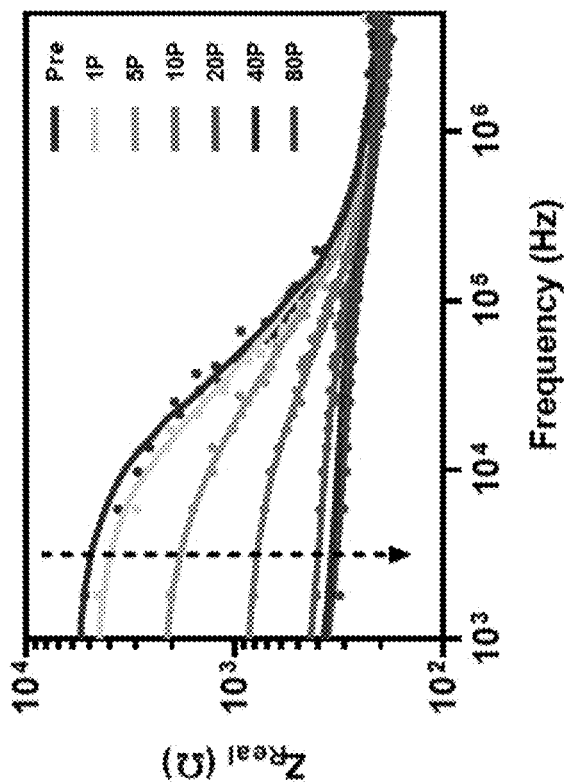
FIG. 7C is a graph showing bulk potato impedance after administration of varying numbers of IRE pulses.

In embodiments, the real impedance data matches that attained from a commercial potentiostat (FIGS. 7A-C). Notably, the commercial potentiostat realized a complete impedance spectrum in >10 s, whereas FAST impedance measurements are realized <<1 s, thereby enabling impedance capture when using electroporation pulsing rates of 1 Hz. FAST can be utilized for monitoring the extent of tissue/cellular recovery or lack thereof during pulsing in real time. As seen in FIG. 7C, the extent of electroporation from IRE treatment can be reliably captured and shows good agreement with the commercial potentiostat (e.g., as shown by the flattening of the impedance curve for 80 pulses as compared with that of 1-20 pulses). In embodiments, the use of dedicated hardware (such as an H-Bridge low-voltage pulse generator, or other low-voltage generator, which can be incorporated into the system with any required drive circuit as a stand-alone component or integrated as part of the generator) can be employed to also apply diagnostic FAST pulses to monitor the recovery (electroporation and/or temperature) during treatment after pulses and/or bursts (such as after every pulse), providing real-time feedback for electroporation-based therapies. This methodology can be achieved by interlacing diagnostic and therapeutic FAST schemes at a desired repetition rate (see, e.g., FIGS. 15 and 22).

Using embodiments of the invention, recovery dynamics can now be explored. A slow tissue impedance recovery (back to baseline) will signify dead/dying tissue, whereas a quick recovery can suggest reversible or minimal electroporation, with such analyses helpful in determining when a particular treatment endpoint has been reached, and/or when a particular treatment should be modified/adjusted, halted or stopped.

Figure 12A:
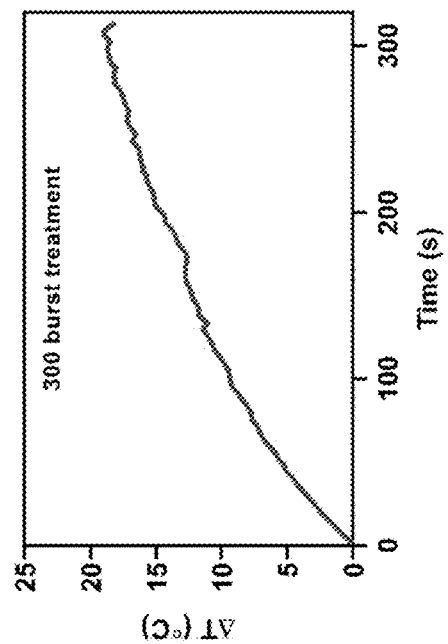
FIGS. 12A-D are graphs of a clinical endpoint for irreversible electroporation, which show impedance after 300 bursts are delivered across a tissue (FIG. 12A); a high increase in temperature following delivery of the 300 burst treatment (FIG. 12B); the FAST-controlled pulsing endpoint as the impedance spectrum saturates to a high-frequency reference (FIG. 12C); and the decrease in total change in temperature using a FAST-controlled treatment protocol (FIG. 12D), where the arrow in FIGS. 12A and 12C indicates the progression of treatment with high-voltage pulses (H-FIRE), which causes a decrease and flattening of tissue inter-burst impedance.
Figure 12B:
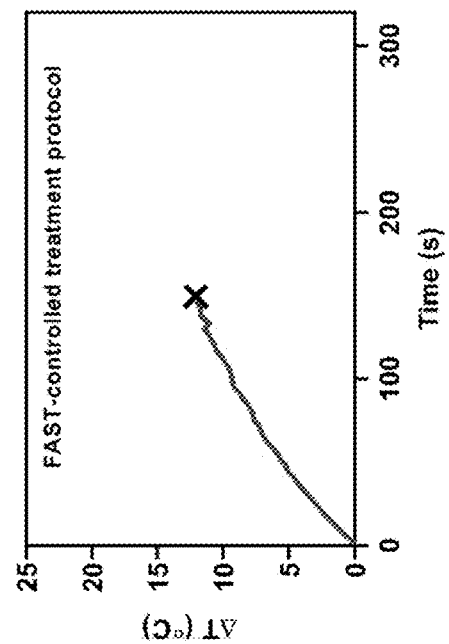
Figure 12C:
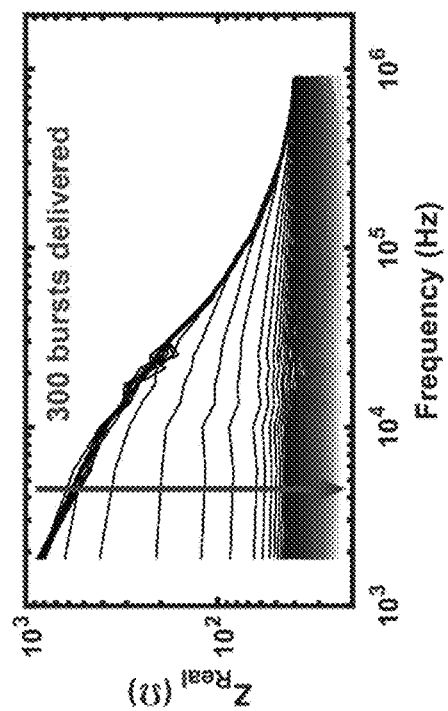
Figure 12D:
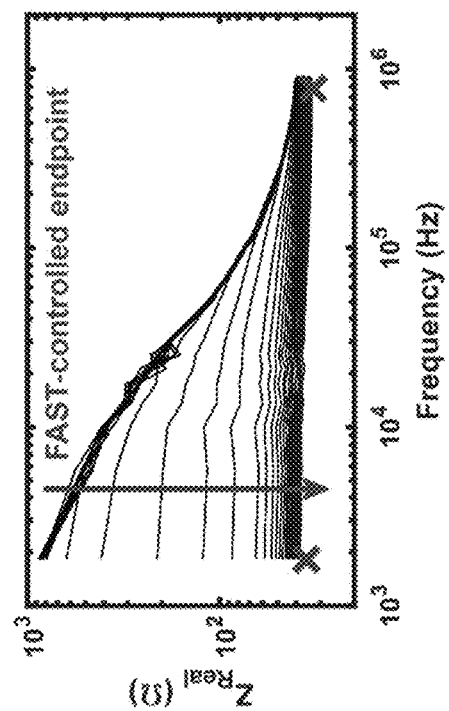
Figure 12F:
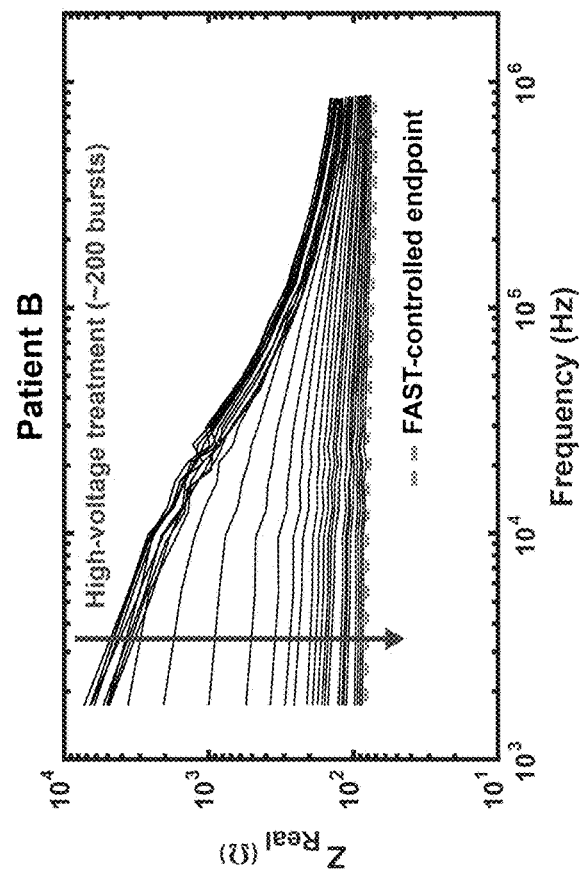
FIGS. 12E-F are graphs demonstrating respective clinical endpoints for patients with different electrical impedance values.
Figure 12E:
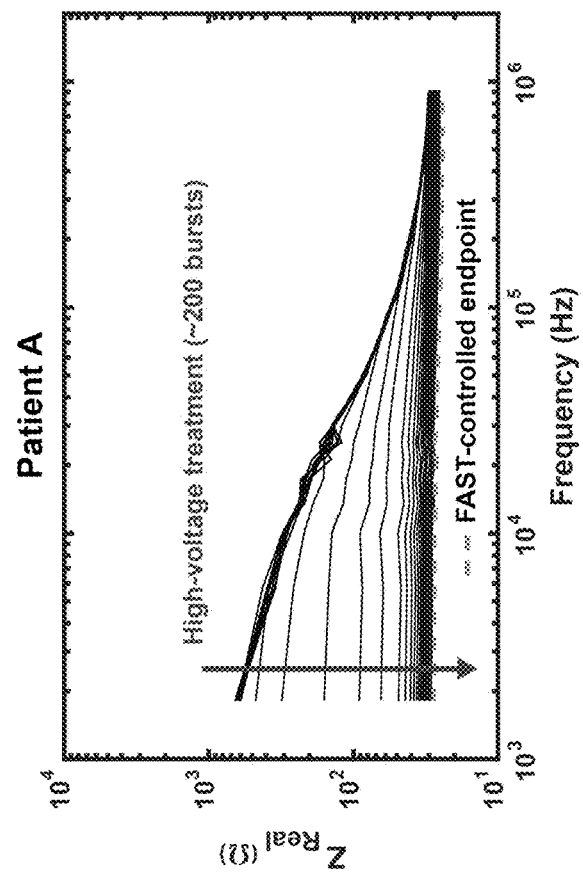

Diagnostic FAST can be used to provide a patient specific endpoint for electroporation-based therapies. While the existence of the beta dispersion within an impedance spectrum of a densely populated cell suspension/tissue is known, FAST allows for detecting the magnitude of the high frequency impedance. Once this value is determined, a low frequency impedance measurement can be monitored for its saturation to the high frequency impedance reference; this will signify ablation of cells within a therapeutic field, as this is an indication of cell membrane damage. The magnitude of this impedance will vary patient to patient, though the saturation of the low frequency to the high frequency impedance can serve as a marker for the endpoint of treatment. For example, as shown in FIGS. 12E-F, different respective clinical endpoints for patients with different electrical impedance values can be expected.

This relationship, saturation of the low frequency (~5 kHz) to high frequency (~2 MHz) impedance, is specific to peripheral tumor tissue, calcified tumor tissue, necrotic tissues, healthy/tumor ischemic tissues, traumatic brain injury, fibrotic tissues, tissue states prior to and after chemotherapy, and tissue states prior to and after radiation. This technique is also applicable to the classification of tissues, such as identifying/determining between various tissue types such as brain, liver, prostate, kidney, pancreas, and tumor tissues arising from unique electrical characteristics of each tissue.

Diagnostic FAST can be fine-tuned and utilized to monitor changes in tissue morphology, edema, perfusion, fluid infusion, thermal necrosis, cell death by electrical, mechanical, or thermal means, identifying cell subtypes, identifying intracellular structures and morphology, gauging efficacy of drug delivery, integrity of the blood-brain-barrier, and tissue heterogeneity. For example, with respect to edema, methods of the invention are capable of detecting increases in conductivity due to edema influx, which is an indication of a positive immune response to the EP treatment. In some embodiments, the methods of treating/monitoring can include treating tissue and/or cells (e.g., a tumor or a cancer) within a target site in a subject by administering a plurality of electrical pulses to the target site which can induce non-thermal electroporation, such as irreversible electroporation (IRE), of the treatment site; measuring a treatment parameter, including, but not limited to, impedance or an impedance spectrum; detecting a change in the measured parameter such as a change in impedance; and performing an additional downstream or secondary treatment as a result of a change in impedance that indicates a positive immune response (such as edema), wherein the downstream or secondary treatment step can include, but is not limited to, tumor resection, thermal ablation, a secondary non-thermal ablation, chemotherapy, radiation therapy, immunotherapy, biologic therapy, genetic therapy (gene editing), and combinations thereof.

In particular, for example, diagnostic FAST can be used to monitor tissue decellularization/cell death as the impedance spectrum/dispersion flattens. This technique can be used for, but is not limited to, monitoring tissue ablation such as irreversible electroporation, chemical cell death/decellularization (e.g., by surfactants, acids, and/or bases), disruption by physical means (such as by high-intensity focused ultrasound (HIFU), Histotripsy, and/or laser ablation), monitoring gene-transfection efficiency and/or uptake, monitoring tissue ablation (nonthermal, thermal) for cardiac arrythmias, monitoring cell lysis for immunotherapies, and monitoring mechanisms of cell death. Prior to tissue damage/decellularization, the impedance spectrum will feature a prominent dispersion. Following tissue damage, the dispersion will flatten, indicative of low cellular integrity or cellular density.

While prior literature has shown EIS as a potential tool for monitoring electroporation, the equipment, complexity, and more importantly the time required to implement EIS substantially limits applicability and does not currently allow for real-time measurements. This is true if the application of EIS is for monitoring impedance changes during treatment, as opposed to before and/or immediately after a series of ~100 pulses are delivered. In addition, this invention includes using electrical measurements to monitor temperature changes with existing IRE technology.

With respect to monitoring cell death, lysis will be represented as a flattening of the impedance spectrum/dispersion with no recovery following pulse cessation. As cell lysis involves immediate destruction of the cell membrane, the measurement of impedance recovery, or lack thereof, will be possible on within minutes after treatment. Necrosis will be represented as a flattening of the impedance spectrum/dispersion with minimum recovery following pulse cessation. This assumes pore-formation does not recover and cell is essentially in a lysed state. Apoptosis will be represented as a flattening of the impedance spectrum/dispersion with moderate recovery following pulse cessation. This assumes pore-formation recovery, where the cell dies due to intracellular signaling. As this process occurs on a timescale of hours following treatment, impedance measurements with FAST can be conducted to monitor recovery of the cell membrane within minutes following the end of treatment. Pro-inflammatory forms of cell death, such as necroptosis/necrosis, will aid in determination of administration of immunologic agents.

High frequency tissue impedance measurements can be used to approximate changes in tissue temperature and gauge nonthermal ablation. For example, a 2-5-2-100 μs therapeutic FAST scheme can be used to monitor changes in high-frequency tissue impedance due to temperature. Since changes in temperature are approximated as having a linear impact on the tissue impedance, changes in tissue temperature can be approximated by monitoring the changes in high frequency impedance and using an appropriate temperature coefficient of resistance for the tissue in question:

$$Z_T = Z \cdot (1 + \alpha \cdot \Delta T) \quad (1)$$

Here, $Z_T$ is the conductivity of the tissue at an elevated change in temperature $\Delta T$, Z the baseline conductivity, and α the temperature coefficient of resistance. For potatoes, an alpha value of 2.25%/° C. was used.

As explained in greater detail below, the inventors employ: 1) numerical methods to examine various FAST schemes in regards to the maximum attainable frequency range and resolution, 2) a flat-plate electrode configuration using potato tissue to validate FAST-measured impedance against a commercial potentiostat using the selected diagnostic and therapeutic FAST from numerical methods, 3) a two-needle configuration in potato tissue to monitor impedance changes during IRE therapy and validate FAST-measured impedance against a commercial potentiostat, 4) a flat-plate electrode configuration to heat potato tissue using therapeutic FAST, with the goal of using the measured impedance to delineate thermal effects from those of EP.

In all cases presented, the extraction of impedance from the numerically simulated or experimentally recorded voltage waveforms V(t) and current waveforms I(t) is as follows. V(t) and I(t) were analyzed in MATLAB vR2018a (MathWorks Inc., Natick, MA, US) using the Fast Fourier Transform (FFT) algorithm, in which the length of the FFT was defined as the next power of 2 from the length of the voltage signal. This resulted in V(f) and I(f), thereafter the magnitude of V(f), labeled as $V_{FFT}$, was defined. To identify and isolate high-power peaks in $V_{FFT}$, a peak extraction algorithm in MATLAB was implemented; a single data point was extracted from each high-power peak if the power of the peak was a threshold value 2% of max($V_{FFT}$). The data points identified were subsequently extracted from V(f) and I(f), where the impedance was calculated using Ohm's law:

$$Z(f) = \frac{V(f)}{I(f)} \quad (2)$$

MATLAB functions "real( )" and "imag( )" were used to analyze the real and imaginary parts of the impedance, respectively.

Numerical Testing to Determine the Desired FAST Schemes

Preliminary studies to determine the frequency content of various FAST schemes in the absence of instrument/measured noise were conducted using MATLAB and COMSOL Multiphysics v5.5 (COMSOL Inc., Stockholm, Sweden). Voltage waveforms V(t) of amplitude 15 V were constructed in MATLAB using a series of concatenated rectangular pulses with 80 ns rise/fall-times. These V(t) waveforms were imported into COMSOL for numerical analysis. A 0D circuit model was constructed in the "Electrical Circuit" module for the circuit shown in FIG. 1C and a time-dependent study implemented to attain the current response I(t) from this circuit model. The V(t) and I(t) were then processed to extract the real and imaginary impedance. The parameters for this circuit model, $R_e$, $R_i$, $R_m$, and $C_m$, were fit to the impedance spectrum attained from experimental investigations; here, the variable resistance was assumed constant as EP-effect were omitted. Open-sourced software "EIS Spectrum Analyser" was used to fit this impedance data to the circuit model (A. Bondarenko and G. Ragoisha, "Eis spectrum analyser (the program is available online at http://www.abc.chemistry.bsu.by/vi/analyser/)," Progress in Chemometrics Research, p. 89-102, 2005.). Since the previous experiments were conducted using a 2-electrode configuration, double layer capacitance effects were present and therefore extracted using a constant phase element (CPE); this CPE was omitted from circuit analysis in COMSOL. In addition, the EIS Analyser was used to generate the impedance spectrum of comparison.

Preliminary investigations of various FAST schemes were conducted using MATLAB vR2018a (MathWorks Inc., Natick, MA, US); determination of optimal pulse schemes included minimizing total signal duration (<10 ms) and frequency content following a Fast Fourier Transform (FFT). In MATLAB, ideal voltage waveforms with 8 ns risetimes were produced using a series of concatenated square waves of pulse-widths 1 µs to 1 ms. Similar to H-FIRE bipolar burst schemes, FAST schemes were designed using a (positive phase-intrapulse delay-negative phase) scheme to maintain the clinically beneficial aspects of H-FIRE. Two sets of FAST schemes were constructed to satisfy the following two experimental investigations.

Figure 2A:
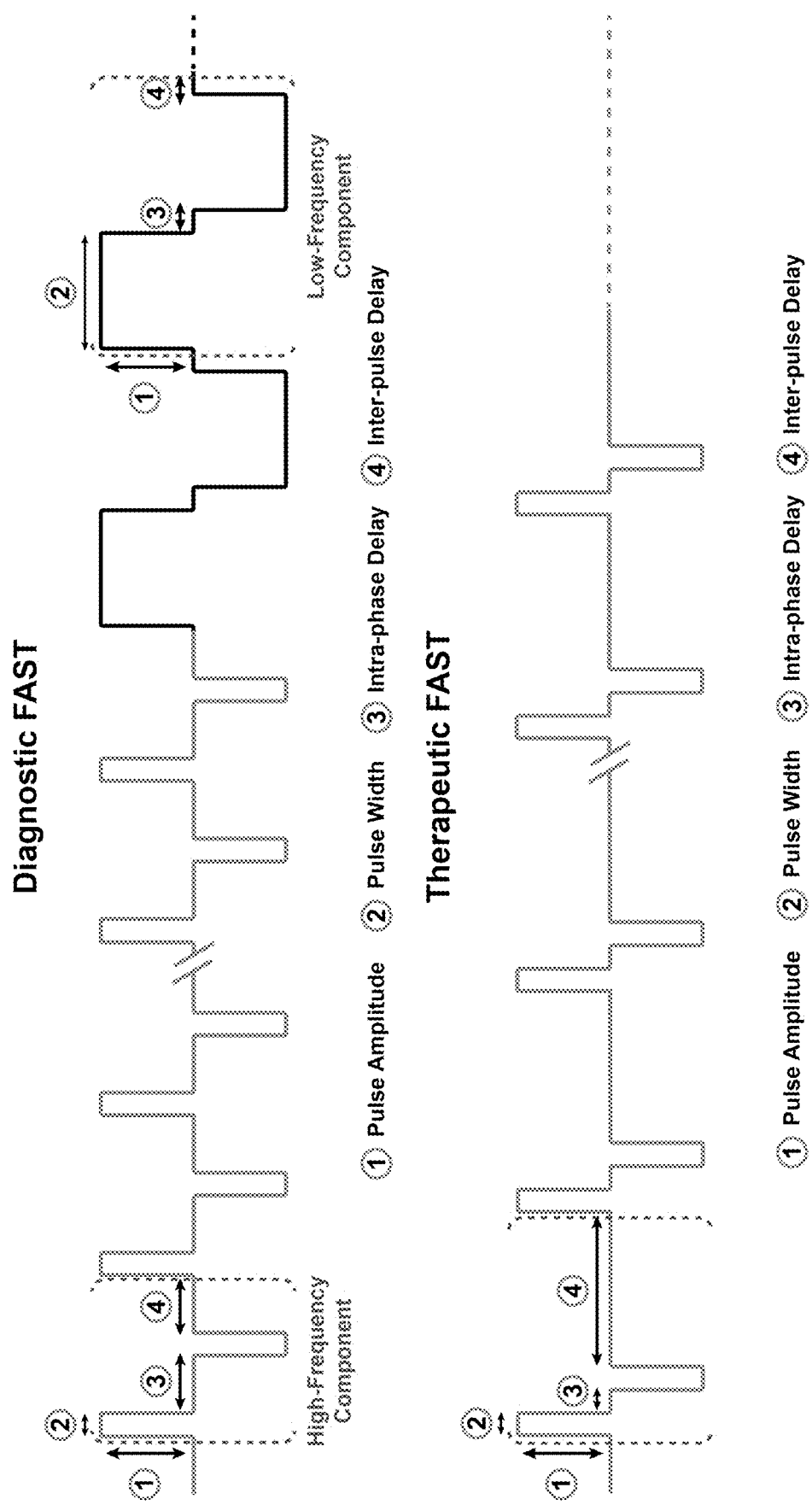
FIG. 2A is a diagram showing representative diagnostic FAST and therapeutic FAST pulse delivery schemes.

Both diagnostic and therapeutic FAST were produced to follow a positive phase–intra-phase delay–negative phase–inter-pulse delay pattern (FIG. 2A), where the pulse-widths and intra-phase/inter-pulse delays were varied ranging for example from 0.1 µs to 1 ms. The representative diagnostic FAST scheme shown in FIG. 2A shows a high-frequency component appended to low-frequency component. In embodiments, and as shown in FIG. 2A, the waveforms can be bipolar, square waveforms. The therapeutic FAST scheme shown in FIG. 2A shows a bipolar square waveform. In other embodiments, the waveforms can be unipolar. With respect to each waveform, the following criteria were imposed:

1) The diagnostic FAST was constructed to attain an impedance spectrum with a desired frequency range of above 0.1 kHz to 100 MHz, such as ~2 kHz-5 MHz. As this waveform is to be applied immediately following an EBT therapeutic pulse, only the total duration of the signal (~10 ms) and the voltage amplitude (15 V) were restricted. The diagnostic FAST was constructed by concatenating a high-frequency signal to low-frequency signal, so two burst schemes are used to describe the final waveform (positive phase–intra-phase delay–negative phase–inter-pulse delay+positive phase–intra-phase delay–negative phase–inter-pulse delay). The inter-burst measurements from this scheme would allow for continuous monitoring of impedance changes during treatment with an EBT. In some embodiments, the energized time for these schemes was not restricted, only to the total duration of the signal (10 ms). A pulsing scheme of a 1-50-1-50 µs (84 cycles) and of 250-10-250-10 µs (2 cycles) was selected (FIG. 3A).

2) The therapeutic FAST was constructed to simultaneously ablate cells/tissue while monitoring intra-burst impedance changes in real-time. To maintain nonthermal ablation, the energized time of each voltage waveform was restricted to 100 µs as is typical with H-FIRE. Additionally, to mitigate muscle excitation, the intra-phase delay of this bipolar burst scheme was restricted to a maximum 5 µs, though the inter-pulse delay was not restricted. In one embodiment, the therapeutic FAST scheme consisted of a 2-5-2 µs H-FIRE pulsing scheme (positive phase, intra-phase delay, negative phase), modified to incorporate a 100 µs extended delay after a set of bipolar pulses (e.g., 100 µs delay after the 2-5-2 µs set of pulses); this delay intentionally zero pads the signal, providing higher resolution in the frequency domain. A representative 2-5-2-100 µs waveform is depicted in FIG. 3B.

Once ideal voltage waveforms were created, an FFT algorithm was implemented to determine the frequency content and power spectral density (PSD) of various burst schemes. The PSD was computed by taking the magnitude of the voltage FFT squared and dividing by the length of the time vector.

Figure 4B:
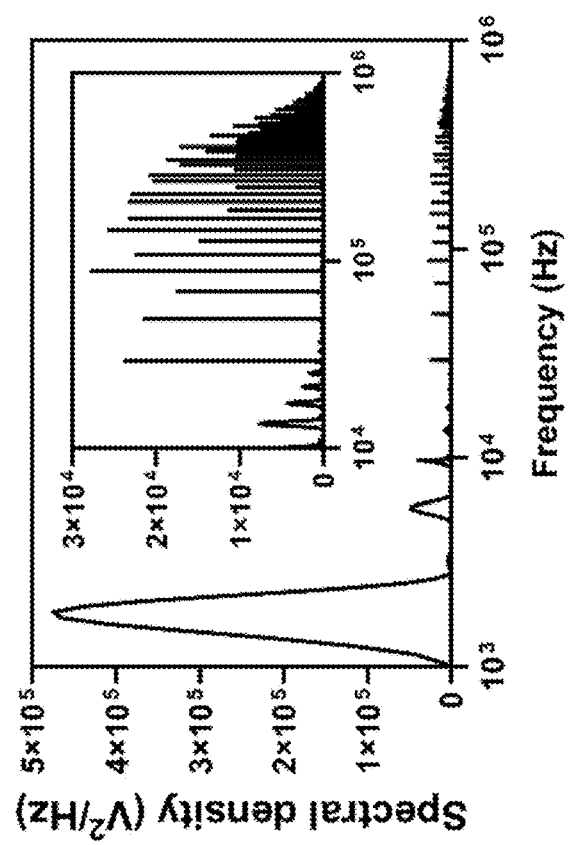

The PSD reveals the frequencies at which data acquisition, the impedance spectrogram, is possible for the 1-50-1-50+250-10-250-10 µs diagnostic FAST scheme (FIG. 4A) and the 2-5-2-100 µs therapeutic FAST scheme (FIG. 4B). As outlined below, it was found that data extracted at frequencies which contain peaks and have a power of at least 2.5% the maximum power of the highest signal provides reliable impedance data that does not differ significantly from data acquired using a commercial potentiostat. Thus, the lowest frequency content with sufficient power for data extraction is located at ~1.8 kHz using the diagnostic FAST, although lower frequencies could be used (such as above 0.1 kHz up to 5 kHz). Above 100 kHz, there are numerous peaks and extends beyond 4 MHz; the upper limit at which the PSD still meets the inventors' criteria was found at 4.8 MHz.

Based on the results, the desired diagnostic and therapeutic FAST which maximized the frequency range and frequency resolution for impedance capture were identified and selected. In embodiments, the desired frequency range for impedance capture and the corresponding selection of pulsing scheme pulse width, intraphase delay, and interpulse delay (diagnostic FAST) can be determined prior to treatment. The impedance extracted from the low-voltage pulse is then used to inform treatment endpoint, which can be controlled by personal or software/hardware.

Validation of Low-Voltage FAST Against a Commercial Potentiostat in Potato Tissue Using Flat Plate Electrodes Following computational investigations in MATLAB, therapeutic and diagnostic FAST schemes were characterized using an in vitro potato tuber tissue model. Like biological tissues, potato tissue is composed of cells embedded within a fibrous matrix, this system loosely represents the macroscopic composition of biological tissues and similarly undergo electroporation. As a result, impedance changes due to electroporation and tissue ablation in potatoes resemble that of biological tissues. Potato tissue ablation occurs through an enhanced oxidative mechanism involving the release of intracellular enzymes that results in a rapid black oxidation of the tissue exposed to higher therapeutic fields; this rapidly oxidized tissue area represents the ablative region.

Select FAST schemes were further tested using a vegetal potato tuber model for validation of FAST-measured impedance against a commercial potentiostat. The system shown in FIG. 2B comprised a function generator programmed to deliver low voltage FAST prior to and following high voltage pulse delivery, an oscilloscope for recording FAST waveforms, a computer capable of processing the waveforms in MATLAB using a Fast Fourier Transform algorithm for decomposition into the frequency domain, and a Gamry Reference 600 potentiostat used to determine accuracy of the FAST-recorded impedance.

A russet potato was sliced to a thickness of 0.7 cm and further sectioned using a cylindrical cutter of diameter 0.8 cm. This tissue sample was placed between two flat plate electrodes (FIG. 2D) with square cross section 2×2 cm (BTX, Harvard Apparatus, Cambridge, MA). A baseline impedance spectrum was measured using a commercial potentiostat Gamry Reference 600 (Gamry, Warminster, PA, US) at a frequency band 1 kHz to 1 MHz at 10 points per decade. The potentiostat impedance spectrum served as a comparison to assess accuracy of the FAST schemes. Following EIS with the commercial potentiostat, low voltage diagnostic and therapeutic FAST schemes were delivered using an AFG31000 series function generator (Tektronix Inc., Beaverton, OR, US) at a voltage 15 V. The voltage and current waveforms were recorded using a WaveSurfer 3024z Oscilloscope (Teledyne LeCroy, Chestnut Ridge, New York) and a 1× current probe (2877, Pearson Electronics, Palo Alto, California). V(t) and I(t) were analyzed. Though therapeutic FAST schemes are ultimately intended to be delivered at higher voltages to generate biophysical tissue changes, a direct comparison to the low-voltage (LV) diagnostic FAST was desired and thus a LV therapeutic FAST was examined. The impedance spectrum acquired from this experiment was used to inform the circuit model fitting for numerical analysis.

Figure 6B:
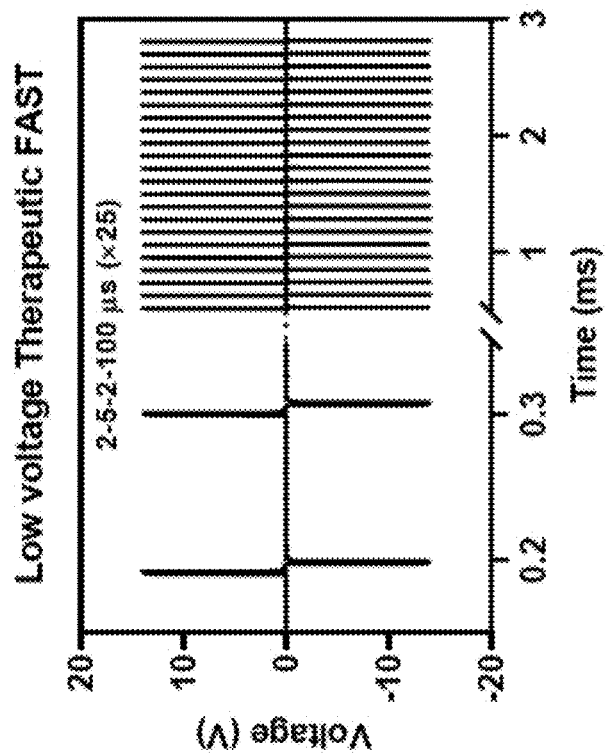
FIGS. 6A-H are graphs depicting an assessment of low voltage diagnostic and therapeutic FAST schemes in 1D potato tissue.
Figure 6A:
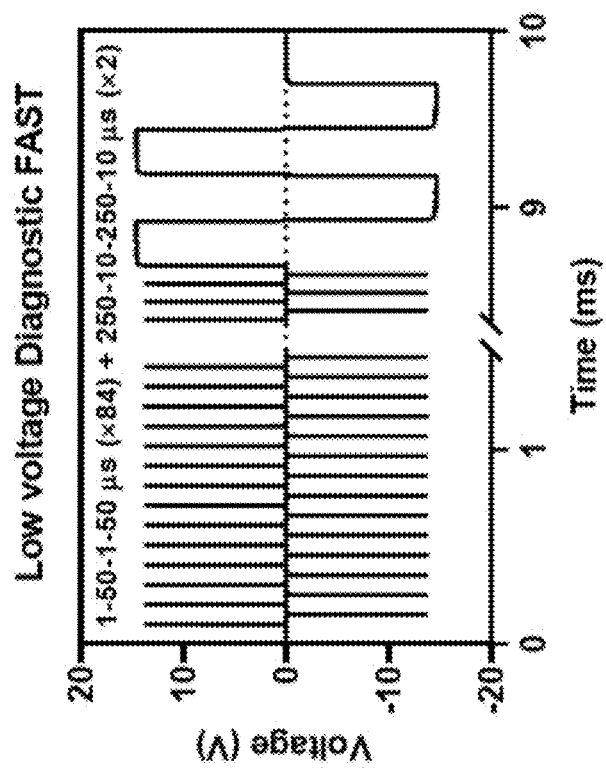
Figure 6D:
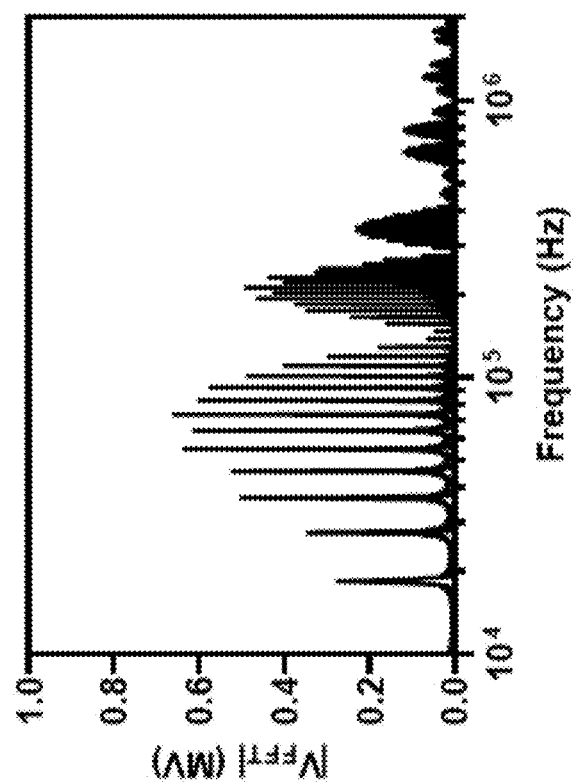
Figure 6C:
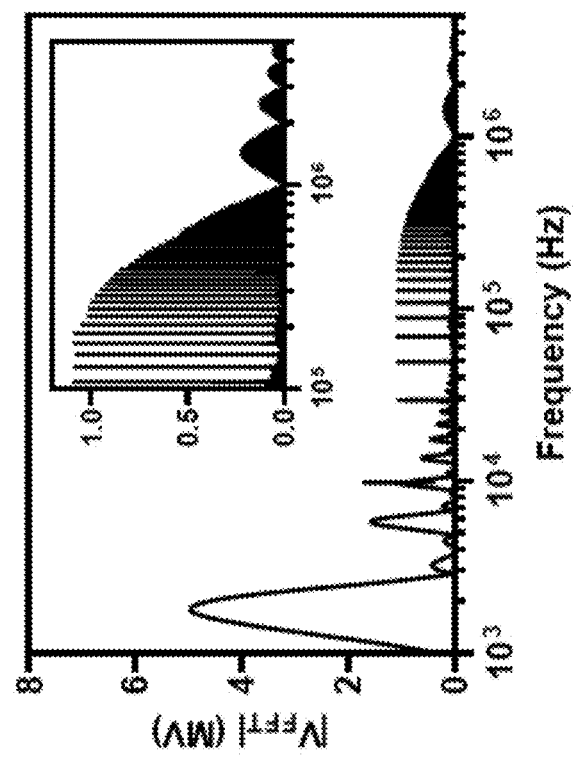

Select diagnostic and therapeutic FAST schemes were tested in potato tissue in vitro (FIG. 6A-B). The diagnostic 1-50-1-50 µs (84 cycles)+250-10-250-10 µs (2 cycles) FAST scheme (FIG. 6A) and therapeutic 2-5-2-100 µs (25 cycles) FAST scheme (FIG. 6B) were delivered across a cylindrical potato section using an arbitrary function generator. Impedance data were extracted from each high-power peak in $V_{FFT}$ and are shown for diagnostic and therapeutic FAST schemes, respectively (FIGS. 6C, 6D) and in comparison to the numerically derived impedance data, the experimental data for $V_{FFT}$ similarly showed an abundance of high-power peaks along the desired frequency range.

The minimum and maximum frequency at which data was extracted for diagnostic FAST were 1.78 kHz and 4.69 MHz, respectively, with 216 data points fitting within this range. For LV therapeutic FAST, the minimum and maximum frequency for data acquisition were 18.3 kHz and 1.82 MHz, respectively, with 170 data points fitting within this range.

Figure 6F:
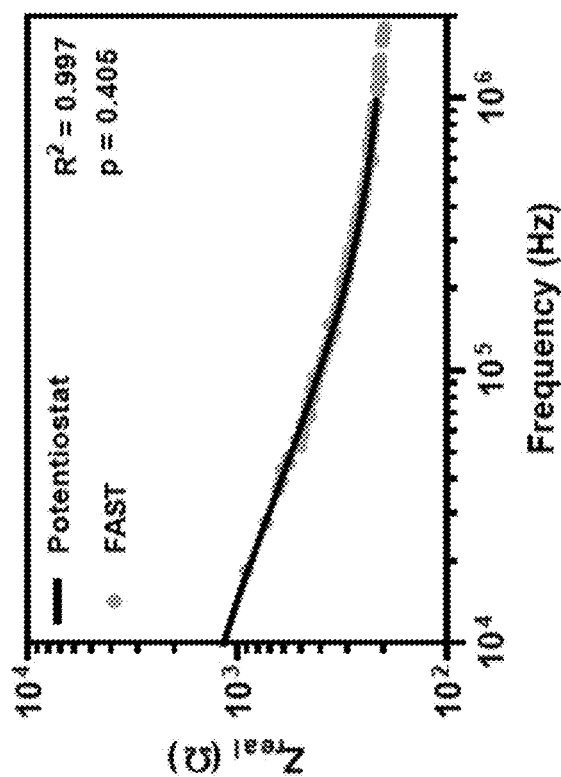
Figure 6E:
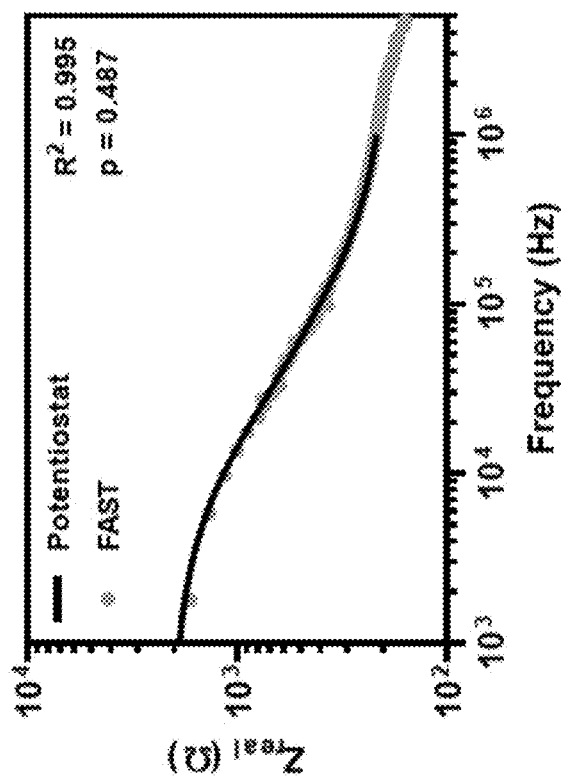
Figure 6H:
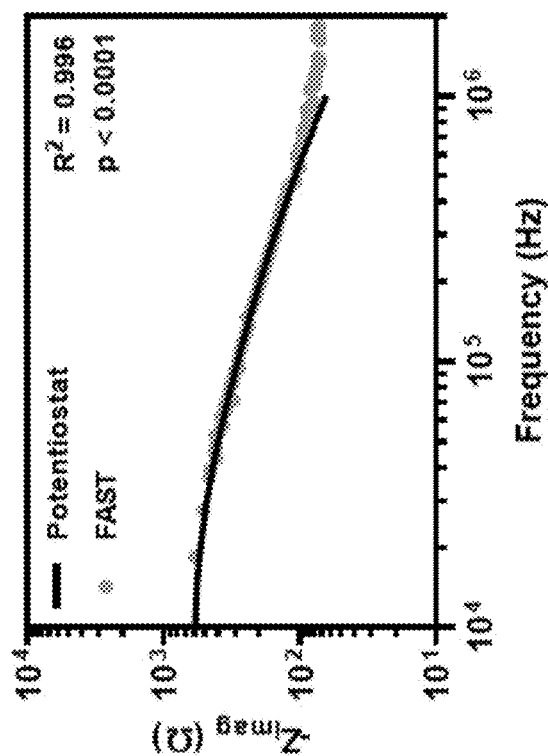
Figure 6G:
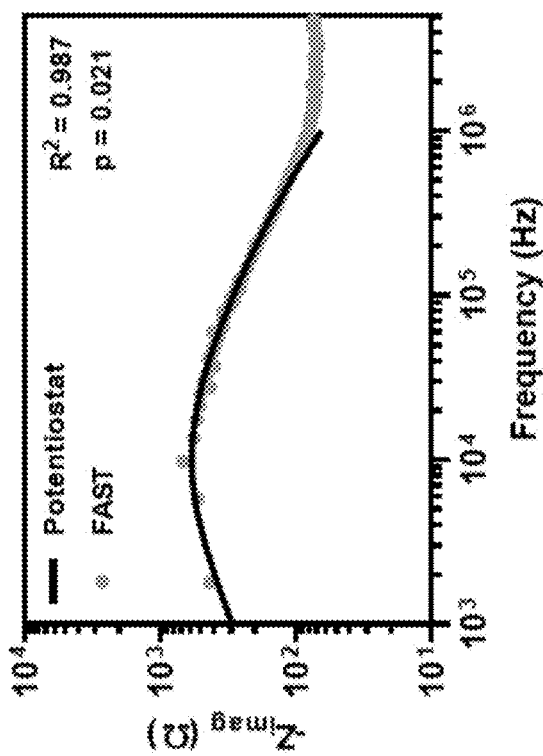

The resultant potato impedance was calculated using Ohm's law; real (tissue resistance) and imaginary (tissue reactance) impedance are shown in FIGS. 6E-H. Nonlinear regression was conducted to test a null hypothesis for a single curve fit being used to describe the potentiostat and FAST generated datasets. For $Z_{real}$ of the diagnostic and LV therapeutic FAST, the null hypotheses were valid: p=0.487 and p=0.405, respectively. The coefficient of determination between the global fits and the FAST-generated $Z_{real}$ data was $R^2$=0.995 for diagnostic FAST and $R^2$=0.997 for LV therapeutic FAST (FIG. 6E-F). In both cases, the null hypothesis for $Z_{imag}$ was rejected, though $R^2$ was determined as 0.987 for diagnostic FAST and 0.996 for LV therapeutic FAST (FIG. 6G-H). In comparison with the numerical investigations, which were performed to test impedance extraction in the absence of noise, 1D experiments demonstrated that noise captured using standard laboratory equipment does not significantly alter the ability to measure impedance.

Diagnostic FAST for Monitoring Ablation Outcome During IRE Therapy with Needle Electrodes in Potatoes Analogous to biological tissue, following PEF treatment, potato tissue undergoes impedance changes due to EP. Therefore, the diagnostic FAST scheme was used to monitor tissue impedance changes and ablation outcome following the application of IRE pulses.

Figure 2B:
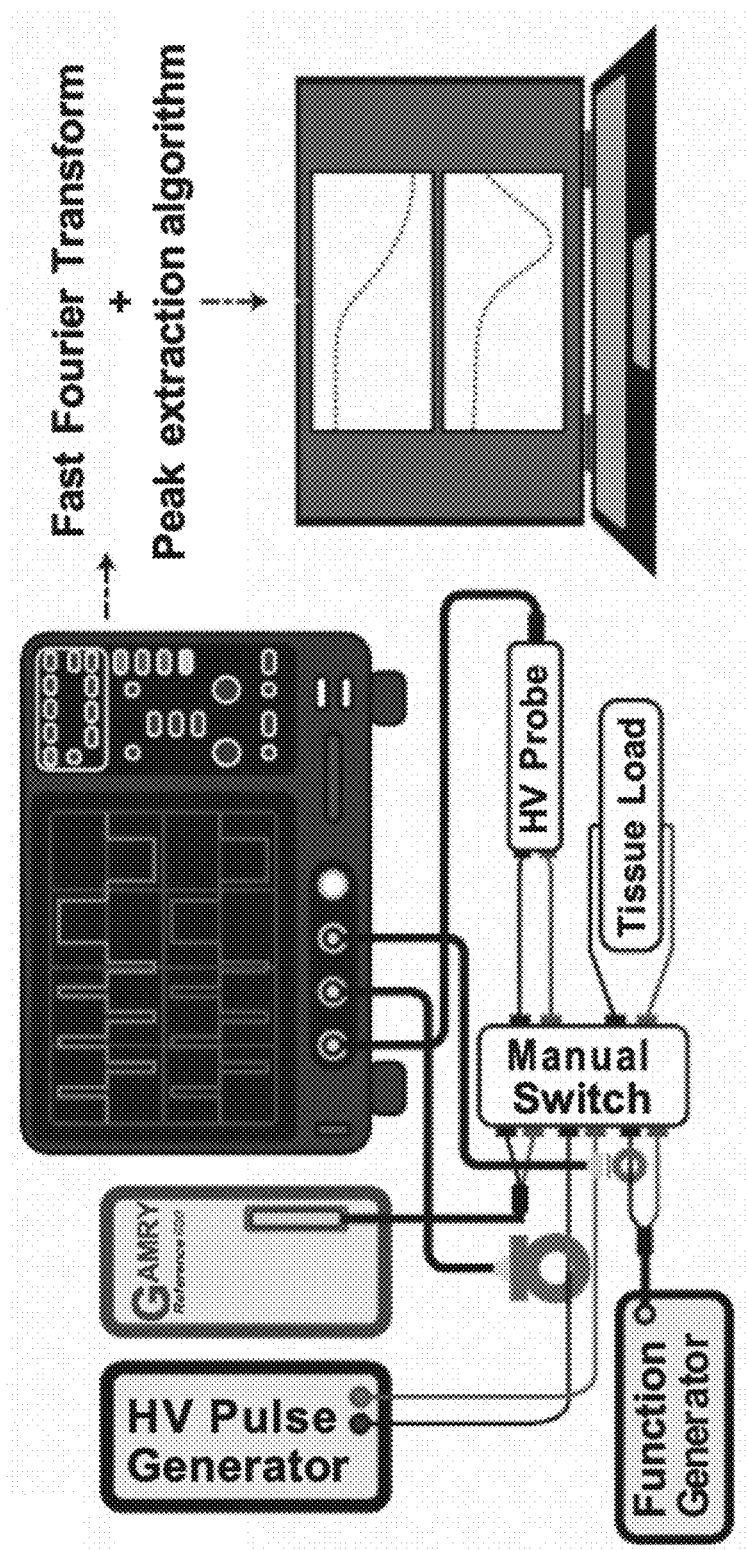
FIG. 2B is an illustration depicting a representative treatment monitoring system according to embodiments of the invention.
Figure 2C:
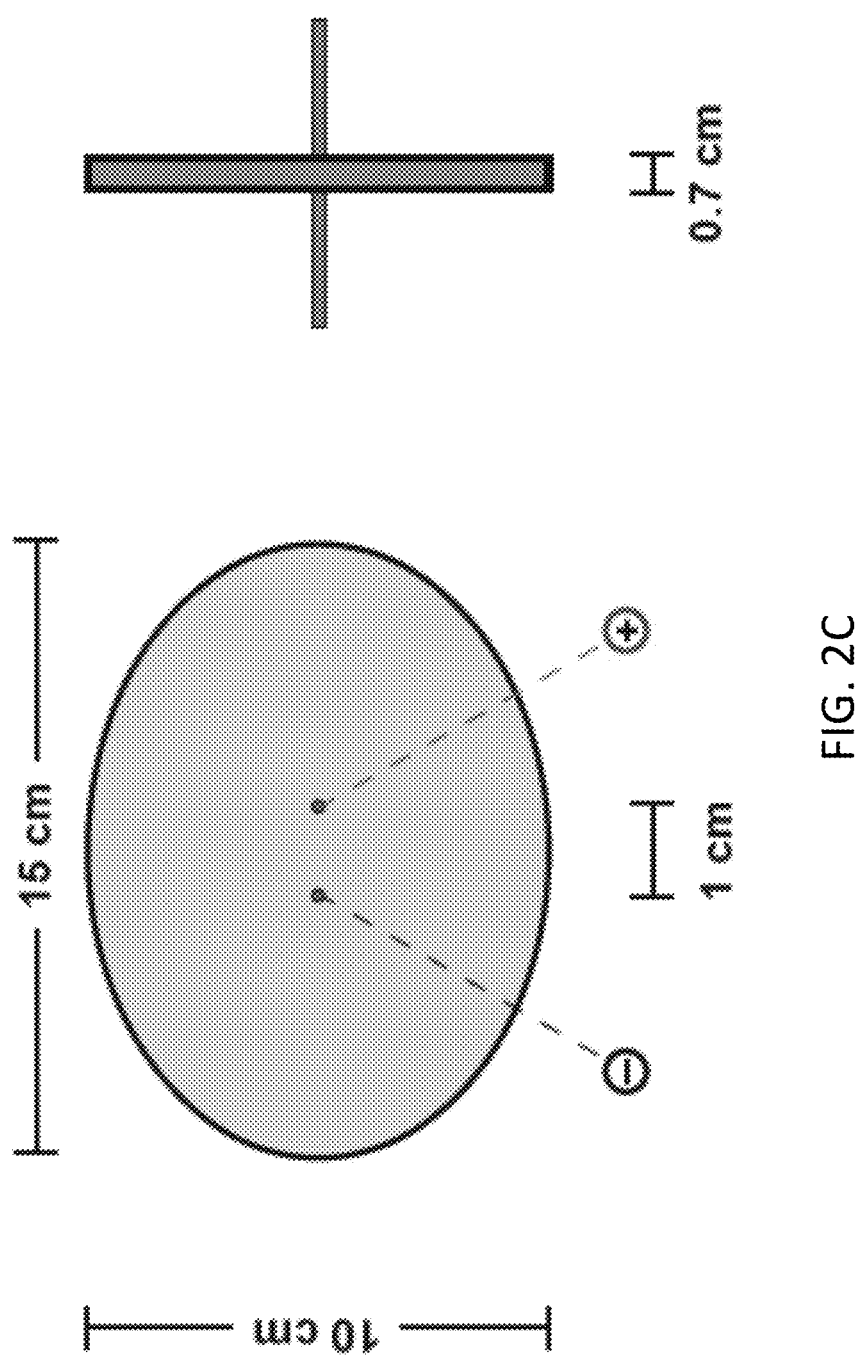
FIG. 2C is an illustration depicting an experimental setup with a 2D configuration to investigate changes in bulk tissue impedance following 1, 5, 10, 20, 40, and 80 IRE pulses.
Figure 2D:
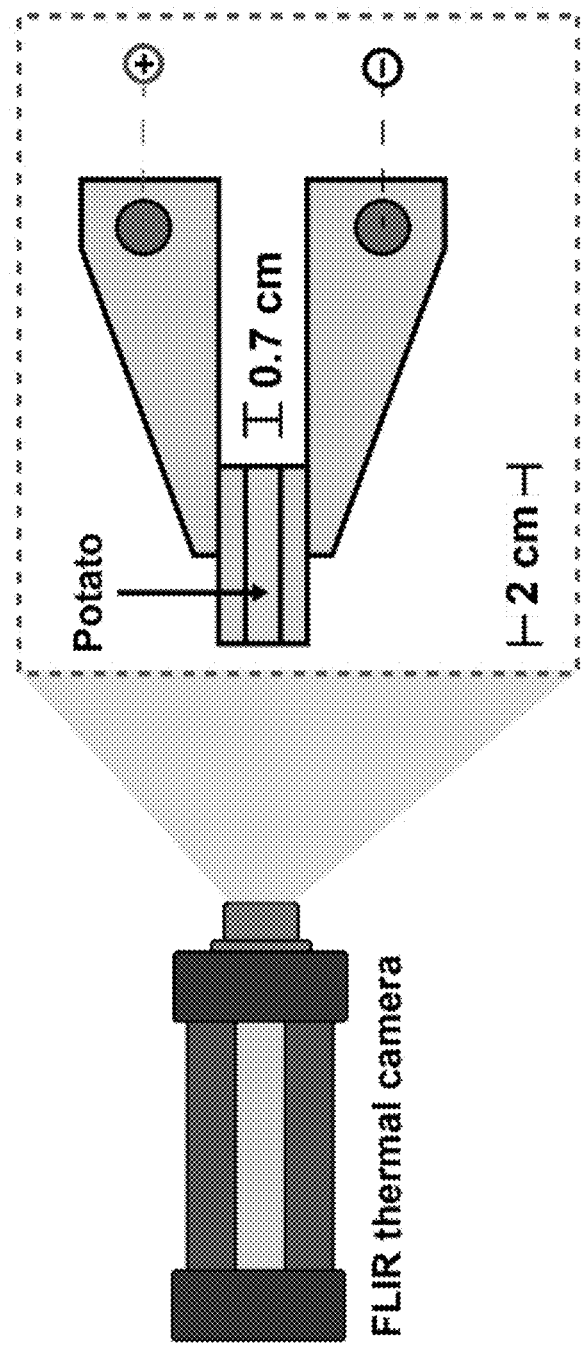
FIG. 2D is an illustration depicting an experimental setup with a 1D configuration aimed towards uniformly heating a potato tissue sample for determination of electroporation and Joule Heating effects.
Figure 2E:
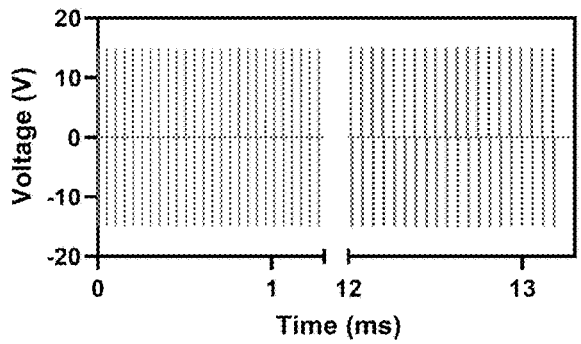
FIG. 2E is a graph depicting examples of diagnostic FAST, with the computed V(f) showing the differences in impedance extraction possible from each waveform.
Figure 2E:
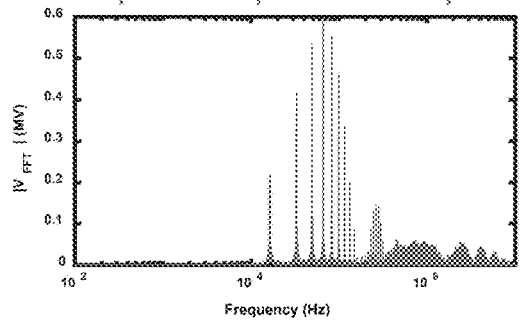
Figure 2E:
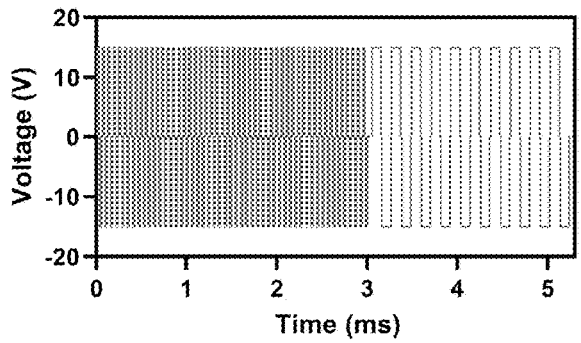
Figure 2E:
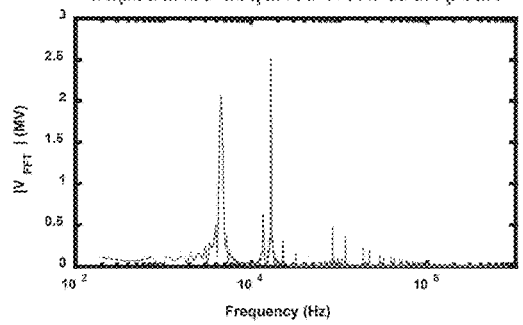
Figure 2E:
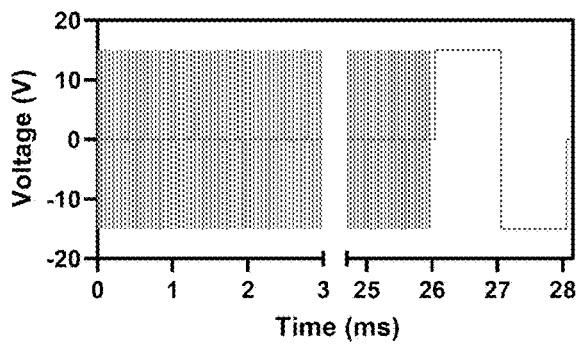
Figure 2E:
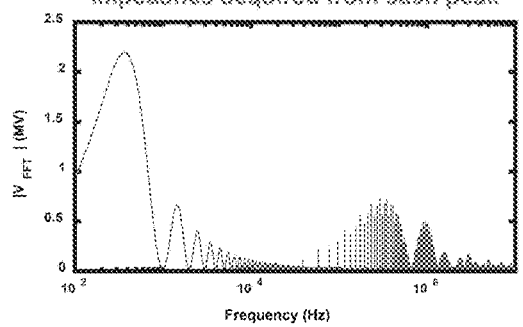
Figure 2E:
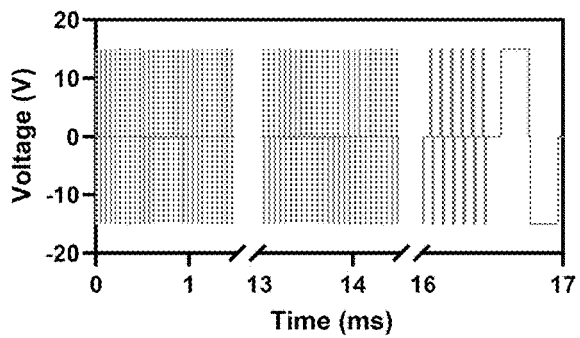
Figure 2E:
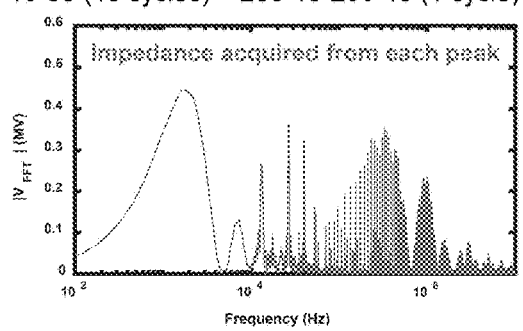

A 2D configuration was implemented to simplify characterization of ablation areas. Potatoes were sectioned uniformly to a 0.7 cm thickness with an ellipsoidal cross section ~15×10 cm using a generic mandolin cutter. Two, 20-gauge cylindrical stainless-steel needle electrodes were inserted at the center of the sample and maintained at a 1 cm spacing; these electrodes were used for both EIS and tissue ablation with IRE (FIG. 2C). Prior to tissue ablation, baseline impedance and diagnostic FAST were implemented. The schematic in FIG. 2B depicts a representative setup.

Prior to tissue ablation, a baseline impedance spectrum was measured using a Gamry Reference 600 (Gamry, Warminster, PA, US) at a frequency band 1 kHz and 1 MHz at 10 points per decade. Thereafter, the diagnostic FAST scheme was also implemented for comparison to the commercial potentiostat. All low voltage FAST schemes were delivered using an AFG3021C function generator (Tektronix Inc., Beaverton, OR, US). The voltage and current waveforms were recorded using a WaveSurfer 3024z Oscilloscope (Teledyne LeCroy, Chestnut Ridge, New York). For high voltage waveforms the voltage was stepped down using a 1000× high voltage probe (Enhancer 3000, BTX, Holliston, MA) while the current was recorded using a 10× current probe (2877, Pearson Electronics, Palo Alto, California). Alternatively, separate LV and HV generators can be used to administer the LV and HV waveforms, respectively.

Following baseline impedance characterization, 1, 5, 10, 20, 40, and 80 IRE pulses were delivered at 1000 V and 100 µs on-time (n=9); additional impedance measurements were taken following each pulse group. To mitigate thermal effects on the measured impedance spectrum, IRE pulses were delivered in sets of 10 where applicable with a 1-minute delay in between each set. The potatoes were covered in plastic wrap and stored overnight to allow for tissue oxidation. The oxidized area in each sample was used to quantify the ablative region and was measured in ImageJ software.

Transitioning to a needle electrode (2D) configuration, FIG. 7A depicts the bulk $Z_{real}$ acquired prior to IRE treatment. Differences between the measured potentiostat impedance were minimal; a single curve fit between potentiostat and FAST-acquired impedance can be described (p=0.216, $R^2$=0.990). A visual comparison between the impedance spectrum acquired using commercial potentiostat and FAST suggests minimal differences. The baseline impedance spectrum (FIG. 7A) as well as after the $1^{st}$, $5^{th}$, $10^{th}$, $20^{th}$, $40^{th}$, and $80^{th}$ pulses (FIG. 7B-C) suggest good agreement across the bandwidth 1.8 kHz-1 MHz. While FAST data was acquired for frequencies up to 4.8 MHz, no direct comparisons for frequencies above 1 MHz were made due to limitations with the potentiostat, however, higher frequencies can be used, such as up to 100 MHz.

IRE was delivered at a pulsing rate 1 Hz; of the 6 treatment groups (Table 1), pulses for groups 4-6 were split into sets of 10 and a 1 minute delay added in between sets to allow for impedance capture with FAST (<1 s) and the potentiostat (>10 s), as well as to allow for heat dissipation. All groups demonstrated an IRE ablation, with 1 pulse (1 P) showing the smallest ablation (1.63±0.26 cm$^2$). As the number of pulses was increased, the ablation area increased: 5 P (2.23±0.34 cm$^2$), 10P (3.45±0.49 cm$^2$), 20 P (3.92±0.33 cm$^2$), 40 P (4.44±0.35 cm$^2$), and lastly the 80 P group resolving in the largest measured ablation (4.57±0.29 cm$^2$) (FIG. 7D).

A one-way ANOVA with Tukey's post hoc multiple comparisons test revealed statistical differences between all treatment groups except for the 10P vs 20 P group (p=0.074) and the 40 P vs 80 P groups (p=0.964). After 20 pulses, there is a slowed progression in ablation size after additional pulses, with the 40 P and 80 P groups showing no statistical differences. Bulk tissue impedance decreased following IRE treatment (FIG. 7B-C). A null hypothesis describing "a single curve fit" between the FAST and potentiostat real impedance was tested; this null hypothesis was valid for the 1 P (p=0.383), 5 P (p=0.675), 10 P (p=0.072), and 20 P (p=0.099) groups. For the 40 P and 80 P groups, the null hypothesis was rejected though $R^2$ to the shared curve fits remained 0.989 (p=0.019) and 0.976 (p=0.003), respectively. In all cases there was good agreement between the potentiostat measured impedance and the FAST calculated impedance.

TABLE 1

Monitoring Extent of Electroporation:
Diagnostic FAST vs. Potentiostat

| Group | 2D ablation with Pulse # × sets | IRE Ablation ($cm^2$) | Nonlinear p-value | Regression $R^2$ |
|---|---|---|---|---|
| 0 | Pre-Tx | 0 | 0.216 | 0.994 |
| 1 | 1 × 1 | 1.63 ± 0.26 | 0.383 | 0.994 |
| 2 | 5 × 1 | 2.23 ± 0.34 | 0.675 | 0.991 |
| 3 | 10 × 1 | 3.45 ± 0.49 | 0.072 | 0.998 |
| 4 | 10 × 2 | 3.92 ± 0.33 | 0.099 | 0.991 |
| 5 | 10 × 4 | 4.43 ± 0.35 | 0.018* | 0.989 |
| 6 | 10 × 8 | 4.57 ± 0.29 | 0.003* | 0.976 |

Mean ± SD;
*p < 0.05, indicates global curve fit is invalid

Delineating Temperature Effects from EP Using High Frequency Impedance

It is known that for a cell suspension and biological tissues, low frequency currents are mostly restricted to the extracellular domain as the intracellular contents are shielded by the highly impeditive cell membrane. At higher frequencies within the beta dispersion band, the cell membrane reactance is essentially shorted and resolves in measurements of a state in which the intracellular and extracellular resistance are in parallel. This state is uniquely realized when tissue is uniformly and nonthermally ablated, such as in tissue ablation with IRE. Once a cell is irreversibly electroporated, electrically, the intracellular and extracellular domains blur; EIS measurements no longer contain a beta dispersion and almost resemble a flat line with the low frequency impedance magnitude converging to that of the high frequency impedance magnitude. Therefore, the relatively unchanged high frequency impedance can be used to monitor changes in temperatures during electroporation-based therapies; this frequency lacks any effects of tissue electroporation, thereby isolating the effects of tissue Joule Heating.

During IRE, the low frequency impedance changes are likely attributed to a combination of tissue electroporation as well as Joule Heating; measuring only the low frequency impedance, as is the standard method with the commercial NanoKnife system, will result in a multivariate signal with no means of separation. The present inventors therefore introduce the measurements of high frequency impedance for isolating impedance changes due solely to Joule Heating. In addition, once the temperature effects on impedance are determined, these temperature effects can then be subtracted from those of the low frequency, effectively isolating the changes in tissue impedance due solely to electroporation.

Figures 1A, 1B, 1C:
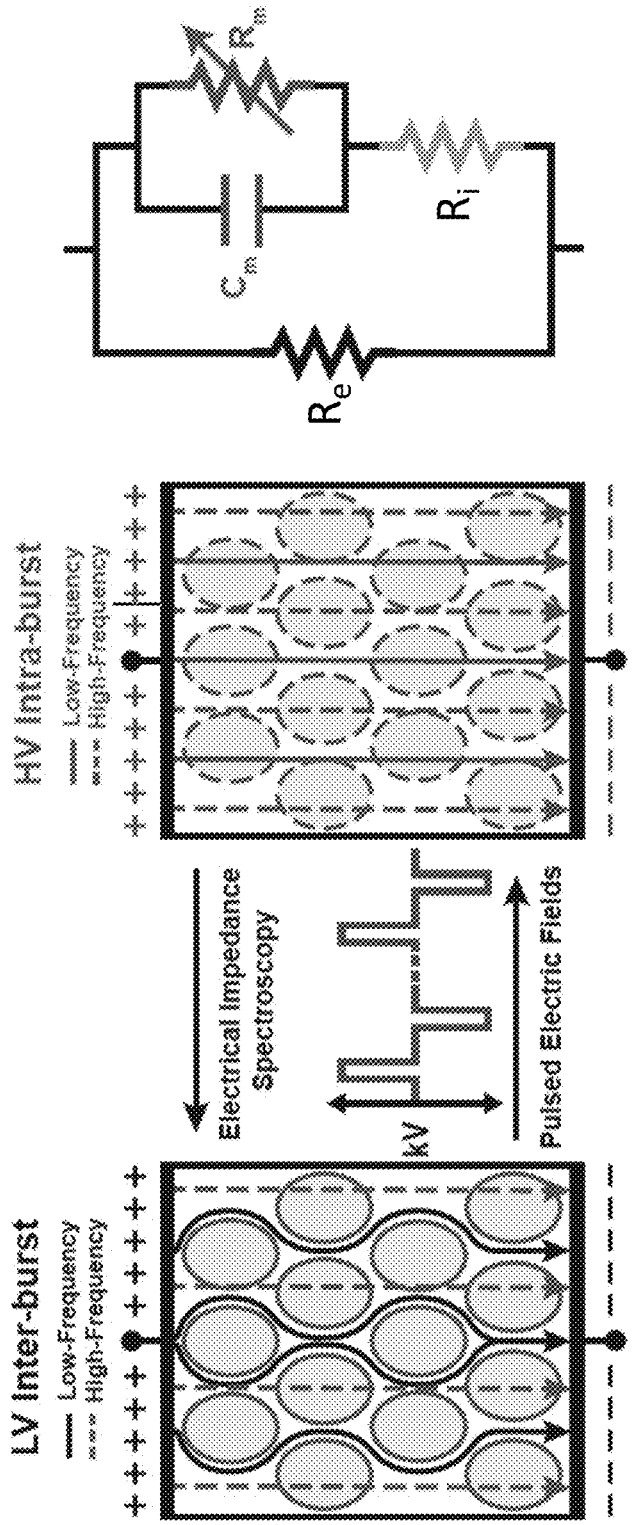
FIG. 1A is diagram showing low voltage inter-burst current paths (of low and high-frequency) during electroporation (EP), where low-voltages are voltages applied such that minimal electroporation effects and minimal heating effects are incurred (e.g., in the range of 0 V to 100 V).
FIG. 1B is a diagram showing high voltage intra-burst current paths (of low and high frequency) during electroporation (EP), where high voltages are voltages which induce desired electroporation effects (such as in the range of 100 V to 15,000 V).
FIG. 1C is an illustration depicting a circuit model representation of biological cells.

As shown in FIGS. 1A-C, at low voltages, the intact cell membrane restricts low frequency electric currents to the extracellular domain. High frequency currents short the membrane reactance, allowing current flow through the cell. Very high voltage PEFs compromise the cell membrane, allowing current to flow through the cell. Changes in low voltage inter-burst and high-voltage intra-burst impedance have been used to quantify EP and this behavior can be described using a circuit model representation of biological cells.

As low frequency currents are mostly restricted to the extracellular domain prior to EP, due to a high membrane resistance, membrane permeabilization throughout PEF treatment greatly influences impedance changes. In addition, Joule Heating effects also shift the impedance spectrum as a function of temperature change. Therefore, it is difficult to isolate thermal and EP effects from the measured impedance. High frequency currents, within the β-dispersion band, short the cell membrane reactance and impedance changes are less susceptible to EP-effects (FIG. 1A). Therefore, this phenomenon was used to investigate use of high frequency impedance measurements to delineate thermal impact from EP. A flat plate EP configuration was used to uniformly heat potato tissue (FIG. 2C).

A therapeutic FAST/H-FIRE waveform of 2-5-2-100 µs pulses was used to simultaneously heat the tissue while resolving in a large enough frequency band to monitor changes in high frequency impedance. H-FIRE waveforms were delivered using a custom bipolar pulse generator (EPULSUS-FBM1-5, Lisboa, Portugal) to output stainless steel electrodes. This generator consists of two unipolar Marx generators capable of producing voltage waveforms with pulse risetimes of 100 ns and a maximum voltage/current output of 5 kV/50 A.

As opposed to the previous 2D electroporation setup, a 1D electroporation setup consisting of flat plate stainless steel electrodes were utilized to expose the tissue to a uniform electric field. A rectangular shape factor of length, width, and thickness dimensions 2 cm×2 cm×7 mm was used. The rectangular shape factor allows for analytical calculation of the tissue conductivity using the following equation: $\sigma = (I \cdot t)/(V \cdot A_c)$, where I is the induced current, t is the sample thickness, V is the applied voltage, and $A_c$ is the cross-sectional area. The H-FIRE treatment comprised 400 bursts of bipolar pulses, each energized for 100 µs at an electric field of 1,500 V/cm.

A russet potato was sectioned to a rectangular shape of length, width, and thickness 2×2×0.7 cm. Prior to treatment, an impedance spectrum was quantified using a low-voltage therapeutic FAST scheme with energized time 100 µs; this scheme was implemented to match the impedance attained during treatment. Thereafter, high voltage therapeutic FAST was delivered using a custom-built H-FIRE generator; due to pulse-generator limitations, output voltage was restricted to 1200 V with an energized time of 40 µs per burst and 400 bursts delivered. Temperature was monitored using a FLIR A325SC thermal camera (FLIR, Wilsonville, OR, USA). High voltage waveforms were recorded using a 1000 high voltage probe (Enhancer 3000, BTX, Holliston, MA) and current was captured using a 10 current probe (3792, Pearson Electronics, Palo Alto, California).

The difference between pre-treatment inter-burst impedance and the $N^{th}$ burst intra-burst impedance is used to quantify temperature increase. By assuming temperature increases linearly with a fixed temperature coefficient of resistance, equation (3) was used to calculate ΔT based on changes in tissue impedance:

$$\Delta T(t) = \frac{Z(t) - Z_0}{Z_0} \cdot \frac{1}{\alpha} \quad (3)$$

Here, ΔT(t) is the calculated increase in temperature, Z(t) is the impedance at the $N^{th}$ burst, $Z_0$ is the pre-treatment impedance, and α the temperature coefficient of resistance. An average α value of 2.8%/° C. was used. (N. Boussetta, N. Grimi, N. I. Lebovka, and E. Vorobiev, ""cold" electroporation in potato tissue induced by pulsed electric field," Journal of food engineering, vol. 115, no. 2, pp. 232-236, 2013).

Nonlinear regression analysis was performed and a null hypothesis describing "a single curve fit" between the commercial potentiostat and FAST impedance data was tested. Here, a p-value<0.05 was considered statistically significant (null hypothesis rejected). The $R^2$ reported are those relative to the global/shared curve fit between the potentiostat and FAST-measured impedance. The real part of the impedance for all data sets was fit to a 4-parameter logistic regression model, an adaptation to the Cole-Cole equations:

$$Z_{real} = Z_\infty + \frac{Z_0 - Z_\infty}{1 + (f \cdot b)^c} \quad (4)$$

The measured ablations were compared using a one-way ANOVA with a post-hoc Tukey's multiple comparisons test. A p-value<0.05 was considered statistically significant. Statistical analysis was conducted in GraphPad Prism v8.2.

Figures 8A, 8B, 8C:
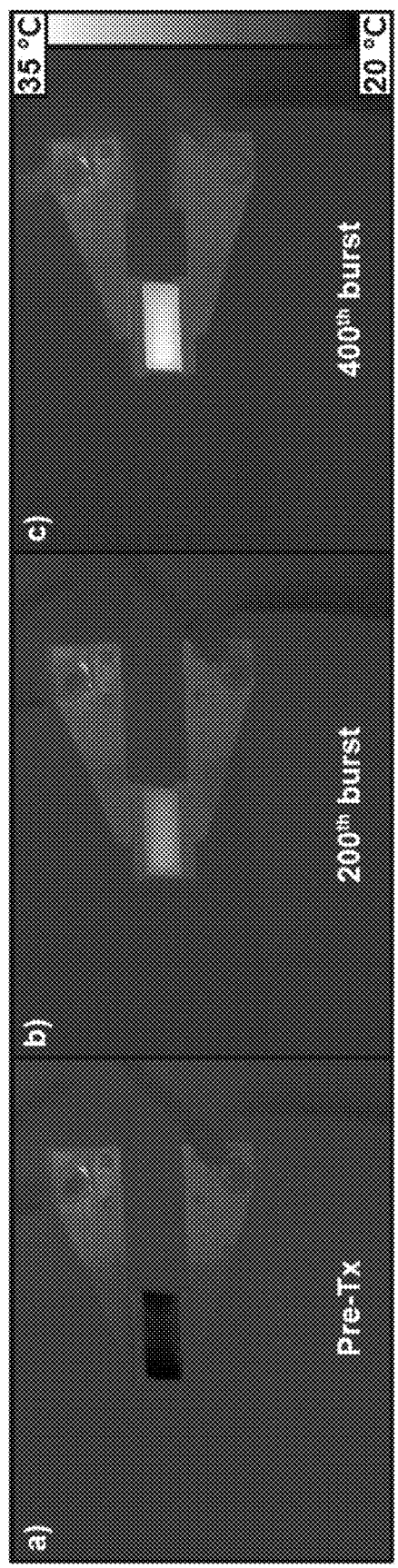
FIGS. 8A-C are photographs taken by a FLIR camera of a russet potato placed between two flat plate electrodes.

More specifically, a FLIR thermal camera was used to record the increase in temperature at a rate of 10 Hz during treatment (FIGS. 8A-C, G). The maximum $\Delta T$ occurred at the end of treatment, measured as 14.8° C. (FIG. 8G). Following pre-treatment impedance characterization with low voltage therapeutic FAST (2-5-2-100 µs, 15 V, 25 cycles, 400 bursts of bipolar pulses (high voltage therapeutic FAST) were delivered (2-5-2-100 µs, 1200 V, 10 cycles), see FIGS. 8D-E).

Figure 9B:
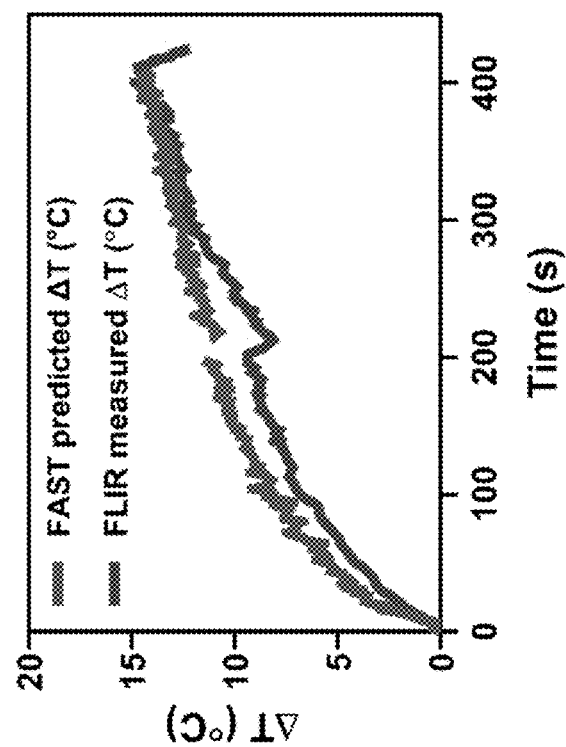
FIG. 9B is a graph showing the application of equation 1, an alpha 2.25%/° C. allows for accurate approximation of temperature changes due to Joule Heating only.
Figure 9A:
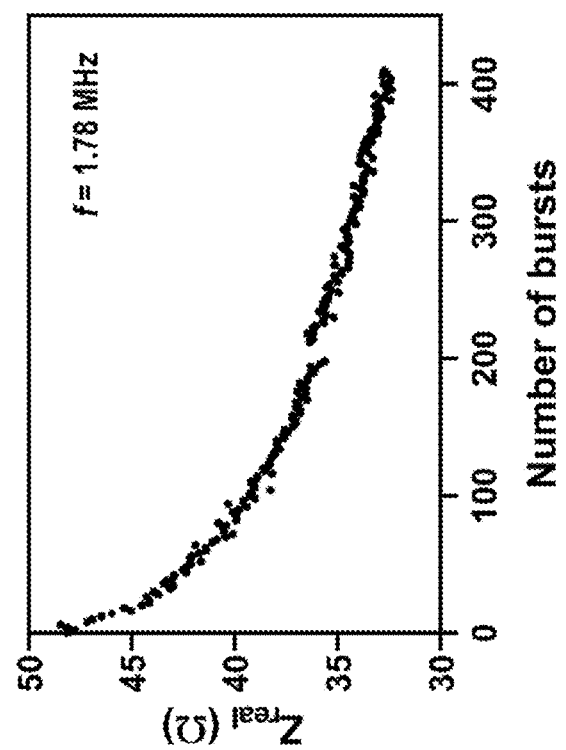
FIG. 9A is a graph depicting high frequency impedance changes to predict temperature changes (electrical impedance vs. number of bursts applied for therapeutic FAST), with a frequency of 1.78 MHz chosen to be sufficiently high to negate impedance changes due to electroporation.

Therapeutic FAST schemes were recorded on the oscilloscope at a rate 0.5 Hz and subsequently transferred to MATAB for analysis. By assuming that the changes in tissue temperature vary linearly with high frequency tissue impedance ($\alpha$=2.25%/° C.), equation 1 is used to predict the $\Delta T$ based off the experimentally varied voltage and current waveforms (FIG. 9B). More specifically, a frequency of 1.78 MHz for this analysis in combination with the therapeutic FAST scheme allowed for the measurement of changes in tissue impedance due to temperature. The estimated temperature profile, seen in FIG. 9B, closely matches that measured using a FLIR thermal camera. Modification of this scheme can yield similar results incorporating higher bandwidth and/or resolution. An H-FIRE treatment containing a (relatively) high EF for potatoes and a (relatively) high number of bursts was applied and resulted in tissue heating. Analysis of the treated potato revealed significant oxidation due to irreversible electroporation of the tissue. The changes in tissue impedance during therapeutic FAST/H-FIRE is seen in FIG. 9A, which depicts the changes in tissue impedance at a frequency 1.78 MHz; this frequency was chosen as this is the location where the tissue impedance varied the least during pulsing, signifying extent of electroporation played a minimal role for the changes in tissue impedance.

Figure 8E:
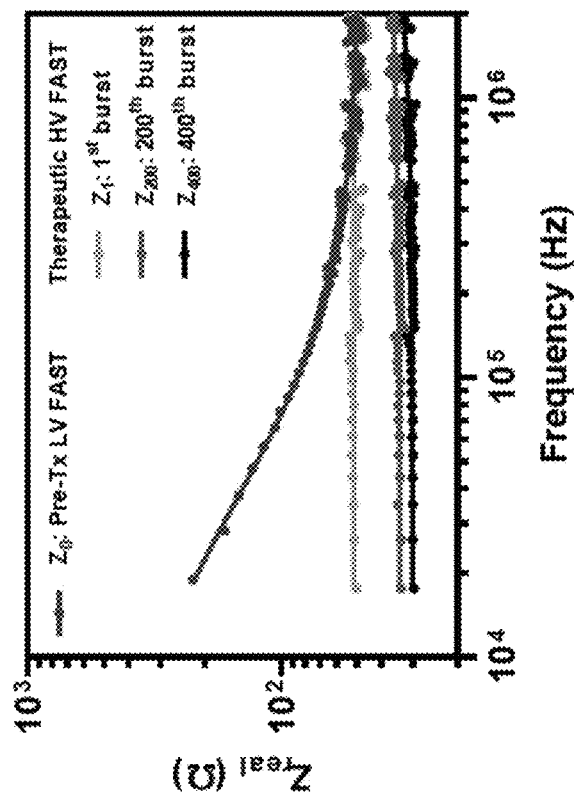
FIG. 8E is a graph showing thermal effects from those of EP, $\Delta T$ was calculated for the impedance change between pre-treatment impedance $Z_0$ and $1^{st}$ burst intra-burst impedance Z1.
Figure 8D:
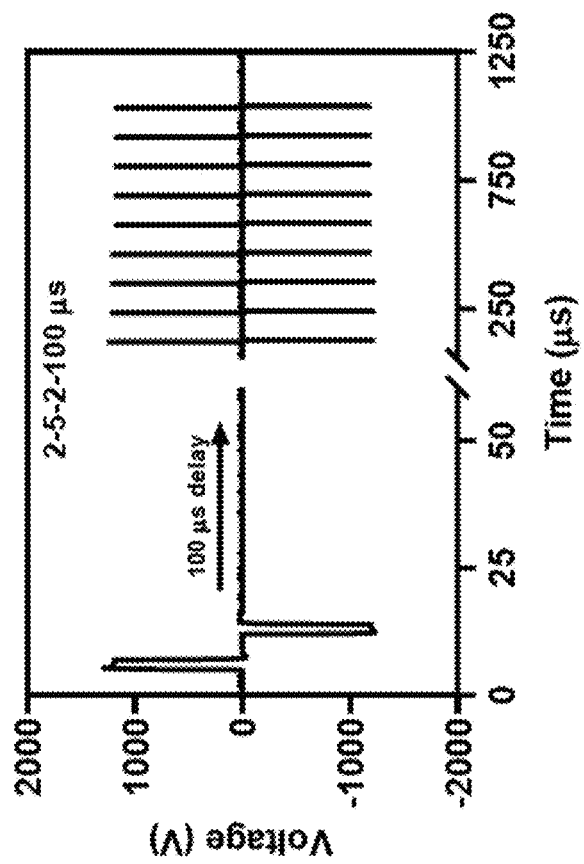
FIG. 8D is a graph depicting a therapeutic FAST (2-5-2-100 µs, 400 bursts, 1200 V, 40 µs energized-time per burst) waveform being applied, for example to delineate thermal and EP effects.
Figure 8G:
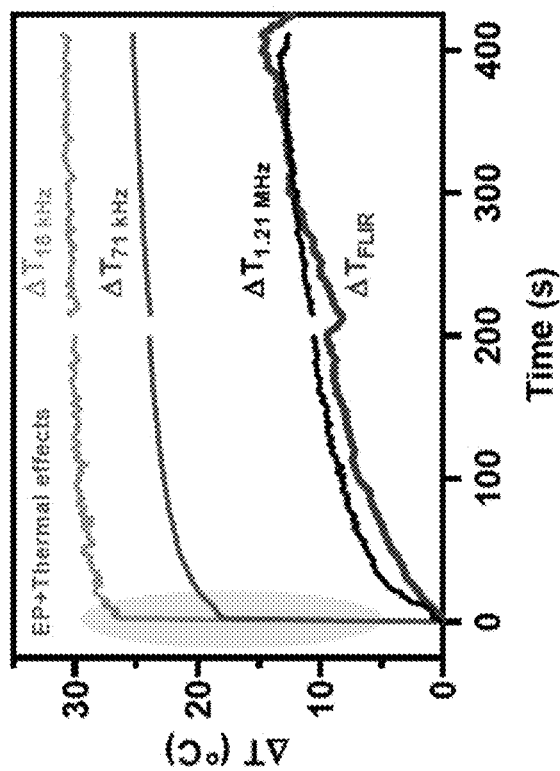
FIG. 8G is a graph demonstrating a negligible temperature rise following the $1^{st}$ HV therapeutic FAST ($\Delta T$ 0.04° C.).

With respect to the circuit model analogy (FIG. 1C), once the applied voltage is sufficiently high to reduce the resistance of the variable resistor component of the cell membrane, the intra-burst impedance is a function of $R_e$ $R_i$; in this experiment, in order to heat the tissue, the applied voltage was seemingly beyond this point and resolved in a relatively flat intra-burst impedance spectrum within the $1^{st}$ burst (FIG. 8E). Subsequently, measurements of intra-burst impedance maintained the flat profile with a shift downwards attributed to a decrease in impedance due to thermal effects.

Figure 8F:
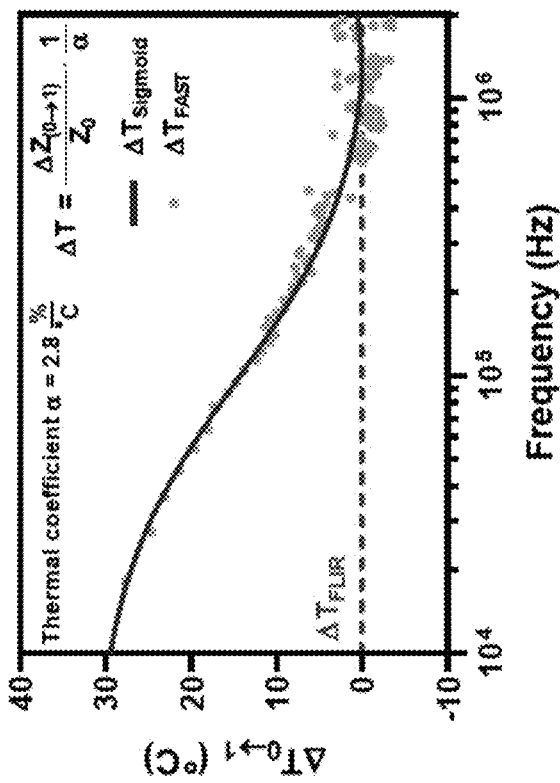
FIG. 8F is a graph showing the impedance changes at temperatures exceeding 25° C. at 18.2 kHz. Analysis of the $\Delta T$ from $Z_0$ to the end of the $400^{th}$ burst intra-burst impedance (Z400).

Between low voltage pre-treatment impedance ($Z_0$) and the $1^{st}$ burst high voltage intra-burst impedance ($Z_1$), a negligible temperature rise was measured $\Delta T$ 0.04° C. (FIG. 8G). Therefore, to delineate thermal effects from those of EP, a calculation of $\Delta T$ for the impedance change between pre-treatment and $1^{st}$ burst intra-burst impedance was conducted to identify nonthermal impedance changes. By assuming the temperature change varies linearly ($\alpha$=2.8%/° C.), equation 3 is used to calculate $\Delta T$ based off $\Delta Z_{0-1}$. As seen in FIG. 8F, if impedance changes at low frequencies are attributed to that of Joule heating, a $\Delta T$ exceeding 25° C. is calculated at 18.2 kHz. To interpolate within the results, equation 4 was used to fit the $Z_0(f)$ and $Z_1(f)$ curves; this fit, in addition the raw calculations, is shown in FIG. 8F. From this fitting, the frequency which minimizes the $\Delta T$ spike, presumably due to EP, after 1 burst was determined as 1.21 MHz.

Therefore, the predicted temperature starting at the $400^{th}$ burst was calculated and is seen in FIG. 8G. Here, the impedance data attained at 1.21 MHz best predicts the measured $\Delta T$, as this frequency is able to penetrate the cell membrane prior to EP and minimizes the impedance changes from initial EP effects. It is stressed again, in order to heat potato tissue, a voltage much higher than that needed to partially EP the tissue was required. In translation to biological tissue, as demonstrated in Bhonsle et al. 2017, fields that partially EP tissue and inherently heat tissue are within the same magnitude and therefore it is expected that EP effects continually contribute to low-frequency intra-burst impedance change as a function of number of bursts.

Low frequency impedance changes are sensitive to EP-effects due to increased cell membrane permeabilization. If high-energy PEFs heat the tissue, this impedance change is a multivariate signal affected by both EP and thermal effects. High frequencies can short the cell membrane reactance and are therefore less susceptible to EP-effects. Potato tissue was uniformly heated (FIGS. 8A-G), and it was determined for potato tissue in the 1D flat plate configuration, 1.21 MHz was a sufficiently high frequency to void significant EP effects. In comparison, interpreting impedance changes at 18.2 kHz as purely Joule Heating approximated a $\Delta T$ far exceeding what was measured.

Numerical Determination of Select Diagnostic and Therapeutic FAST Schemes

Firstly, the parameters $R_e$, $R_m$, $C_m$, and $R_i$ fitted to the impedance measurements were determined as 2071.2Ω, 9.71E06Ω, 6.53 nF, and 198.35Ω, respectively. It should be noted that a more accurate fit to the impedance spectrum is attained by replacing the membrane elements $R_m \| C_m$ with a constant phase element, though the $R_m \| C_m$ was selected to allow for time dependent circuit analysis using the circuit element nodes in COMSOL. The numerical V(t) and I(t) from COMSOL were processed in MATLAB and a subset of the results are plotted in FIG. 5A-F.

Figures 5A, 5B:
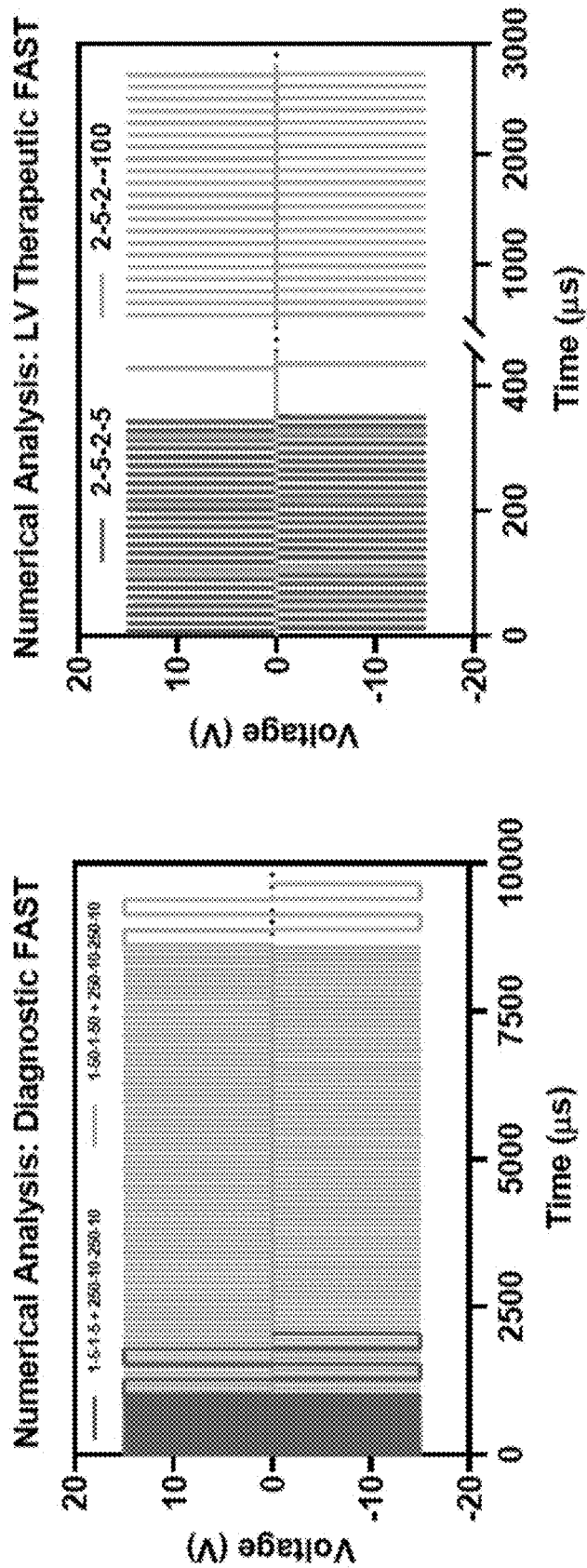
FIGS. 5A-F are graphs depicting the in silico investigation of low voltage diagnostic and therapeutic FAST schemes.

From numerical simulations, two FAST schemes were selected. The diagnostic FAST scheme is a bipolar pulsing scheme consisting of a high frequency signal 1-50-1-50 µs (84 cycles) appended to a low frequency signal 250-10-250-10 µs (2 cycles) for a combined signal duration 9.608 ms (FIG. 5A).

In embodiments, bipolar or unipolar pulses can be used for diagnostic FAST and/or therapeutic FAST, along with any type of waveform (e.g., a waveform with any step, square, sinusoidal, ramp, Gaussian, or sinc function) having constant, increasing, and/or decreasing frequency, or any arbitrary signal designed to achieve a desired frequency spectrum in the range of above 0.1 kHz to 100 MHz.

The total number of pulses/bursts per diagnostic FAST or therapeutic FAST treatment or total number of pulses/bursts per cycle can range from 1 to 5,000 pulses/bursts, such as from at least 1 up to 3,000 pulses/bursts, or at least 2 up to 2,000 pulses/bursts, or at least 5 up to 1,000 pulses/bursts, or at least 10 up to 500 pulses/bursts, or from 10 to 100 pulses/bursts, such as from 20 to 75 pulses/bursts, or from 30 to 50 pulses/bursts, such as 1, 5, 10, 15, 20, 25, 30, 35, 40, 45, 50, 60, 70, or 90 pulses/bursts, or any range in between any of these ranges or endpoints, including as endpoints any number encompassed thereby.

According to any embodiment of diagnostic or therapeutic FAST, each pair of electrodes can be activated by a pulse train with no delay between pulses in the pulse train. In other embodiments, one or more delays can be introduced, such as a delay between one or more pulses in the pulse train, and/or a delay between the activation of one or more pair of electrodes, and/or a delay between one or more of the cycles. The delay can be on the order of microseconds or seconds, such as one to one thousand microseconds, such as 1, 2, 3, 4, 5, 6, 7, 8, 9, 10, 15, 20, 25, 30, 35, 40, 45, 50, 75, 100, 150, 200, 250, 300, 350, 400, 450, 500, 600, 700, 800, 900, or 1,000 microseconds, or one to several seconds such as 1, 1.5, 2, 2.5, 3. 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 24, 26, 28, 30 seconds or more. Cumulatively, the one or more delays may be on the order of seconds or minutes.

Likewise, where cycled pulsing paradigms are used for diagnostic or therapeutic FAST, the number of cycles can be any number of cycles, such as zero cycles, or from 1-100 cycles, or from 2-50 cycles, or from 3-40 cycles, or from 4-30 cycles, or from 5-20 cycles, or from 10-15 cycles, or any range in between any of these ranges or endpoints, including as endpoints any number encompassed thereby.

Figure 5D:
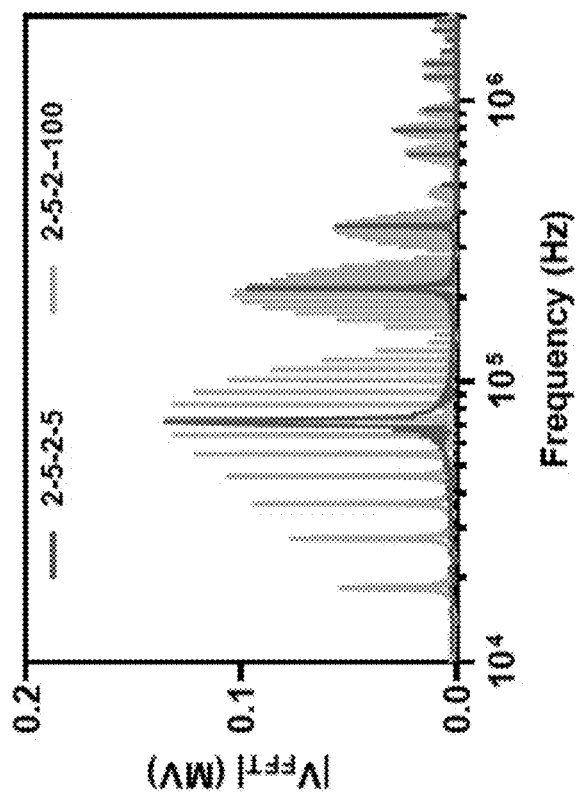
Figure 5C:
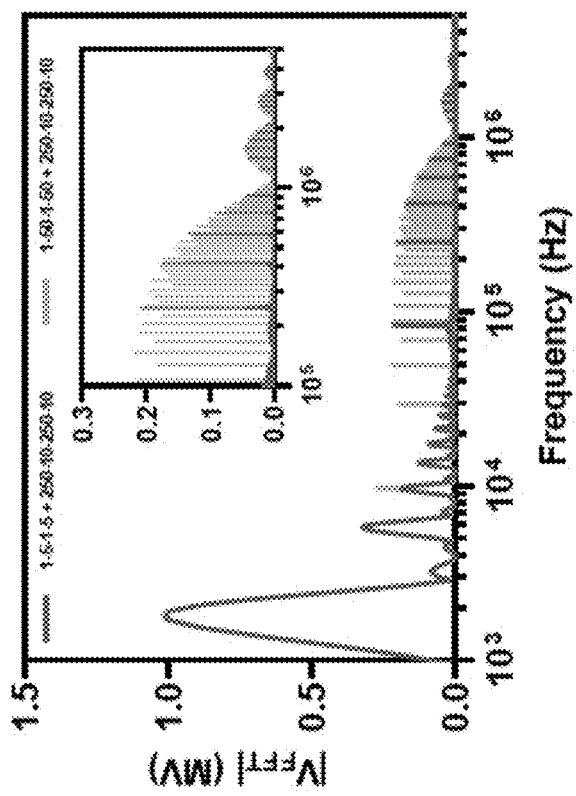
Figure 5E:
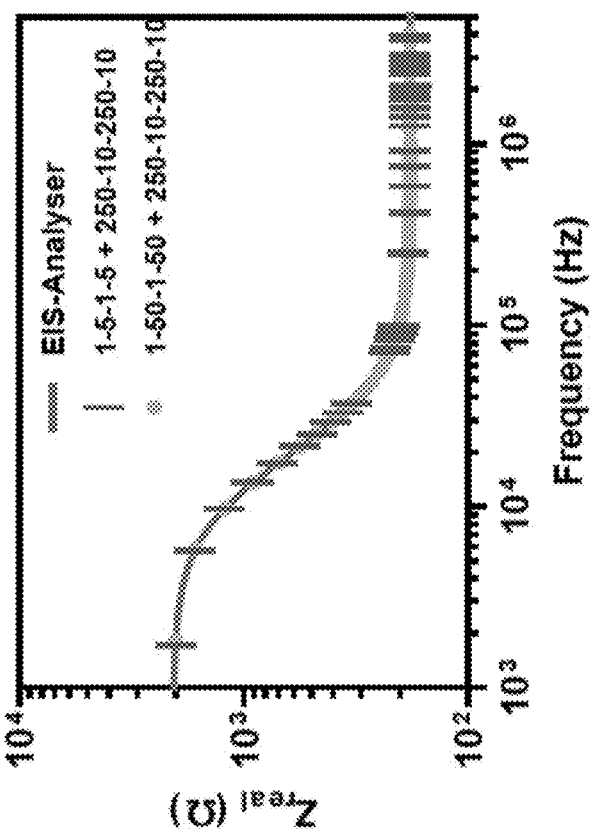
Figure 5F:
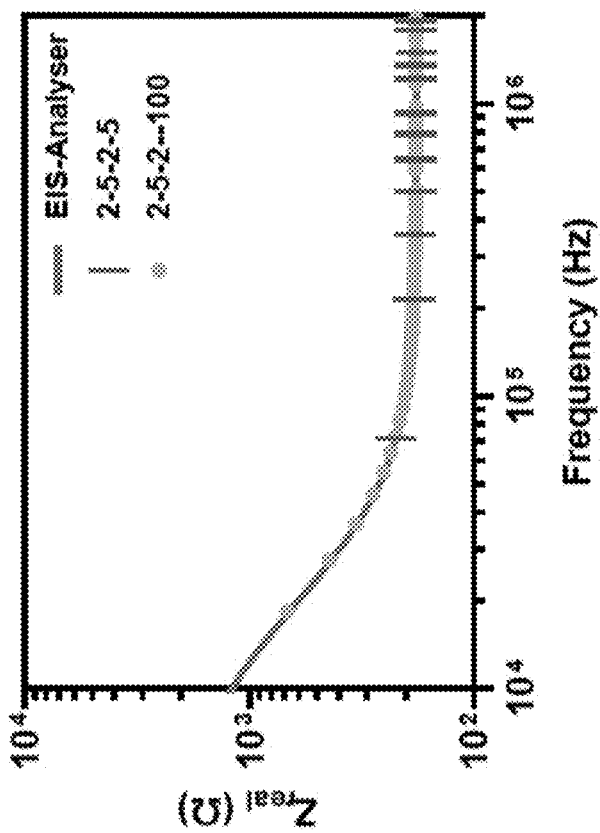

The therapeutic FAST scheme is a modified H-FIRE burst scheme to include an extended inter-pulse delay (e.g., 100 μs): 2-5-2-100 μs burst scheme (25 cycles) energized for 100 μs (FIG. 5B). A comparison between diagnostic FAST of 5 μs and 50 μs intra-phase and inter-pulse delays is seen in FIGS. 5A, 5C, and 5E. Here, it is seen that an increased intra-phase and inter pulse delay seemingly increase the resolution of the frequency band. Therefore, the 50 μs intra-phase and inter-pulse delay was selected. A comparison between therapeutic FAST and a 2-5-2-5 μs H-FIRE burst scheme is seen in FIGS. 5B, 5D, and 5F. The increased inter-pulse delay, from 5 μs to 100 μs increased the resolution of the impedance spectrum.

An FFT algorithm was implemented to attain V(f) and I(f); the magnitude of V(f), labeled $V_{FFT}$, is shown for the diagnostic FAST scheme (FIG. 5C) and the low-voltage (LV) therapeutic FAST schemes (FIG. 5D). For peaks in the $V_{FFT}$ plots containing at least 2% of the maximum power in the signal, impedance was extracted. For diagnostic FAST, the real part of the impedance is seen in FIG. 5E. For therapeutic FAST, the real part of the impedance is shown in FIG. 5F. With the imposed criteria, the 1-50-1-50+250-10-250-10 μs diagnostic FAST scheme produced 204 data points within the frequency range of 1.81 kHz-4.93 MHz and the 2-5-2-100 μs therapeutic FAST produced 164 data points within a frequency range of 18.3 kHz-1.96 MHz.

Diagnostic FAST demonstrates frequency content ranging from ~2 kHz to 5 MHz; 204 data points were extracted within this frequency range (FIG. 5E). Therapeutic FAST demonstrates frequency content ranging from ~20 kHz to 2 MHz; 164 data points were extracted within this frequency range (FIG. 5F).

Broadband Impedance Spectroscopy with Diagnostic FAST

A diagnostic FAST waveform consisting of a high frequency signal 1-50-1-50 μs (84 cycles) appended to a low frequency signal 250-10-250-10 μs (2 cycles) was identified to reliably capture impedance with a frequency range spanning 1.8 kHz-4.9 MHz at 216 discrete frequencies. A broadband impedance spectroscopy is achievable using pulsing parameters currently applied in EBTs.

Although the distribution of frequencies is neither linearly nor logarithmically spaced (B. Sanchez and R. Bragos, "Fast electrical impedance spectroscopy for moving tissue characterization using bilateral quasilogarithmic multisine bursts signals," in 4th European Conference of the International Federation for Medical and Biological Engineering. Springer, 2009, pp. 1084-1087), nonlinear regression demonstrated the real part of the impedance acquired from FAST does not deviate significantly from that of a calibrated commercial potentiostat (FIGS. 6E-F (FIGS. 6E-F show the real parts of the impedance, whereas FIGS. G-H show the imaginary parts). As tissue electroporation occurs on the order of 100's of V/cm for 100 μs pulse-widths, with lower pulse-widths exhibiting higher field thresholds, application of 15 V (~21 V/cm) was considered to remain sub-EP and allowed for high signal-power (and consequently signal-to-noise ratio) in V(f) & I(f).

Therapeutic FAST Allows for High-Bandwidth Intra-burst Impedance Spectroscopy

The therapeutic FAST waveform is proposed to permeabilize/ablate biological cells while simultaneously allowing for high-bandwidth intra-burst impedance spectroscopy. The selected therapeutic FAST is a high voltage 2-5-2-100 μs burst scheme, an H-FIRE burst scheme modified to include an extended inter-pulse delay following the negative polarity pulse. This extended inter-pulse delay increases the resolution of the impedance spectrum, allowing for intra-burst impedance spectroscopy between 18.3 kHz to 1.96 MHz (FIG. 5) at 170 discrete frequencies. Since the intra-phase delay remains 5 μs, minimal impact on the muscle/nerve stimulation thresholds was expected (B. Mercadal, C. B. Arena, R. V. Davalos, and A. Ivorra, "Avoiding nerve stimulation in irreversible electroporation: a numerical modeling study," Physics in Medicine & Biology, vol. 62, no. 20, p. 8060, 2017). Interestingly, an extended inter-pulse delay has been shown to moderately decrease permeabilization and lethal thresholds in vitro (Vizintin et al., 2020).

Monitoring Change in Temperature Using Tissue Electrical Impedance

In contrast to impedance change at low-frequencies being sensitive to both EP effects and Joule heating, the inventors have found that high-frequency impedance measurements, whose corresponding electric currents short the membrane reactance, are less sensitive to EP effects and can uniquely act to distinguish thermal effects. The flat-plate electrode configuration (FIG. 2D) was used for confirmation to uniformly heat potato tissue using high-intensity H-FIRE. Thus demonstrating that analysis of impedance changes throughout electroporation treatment allows for determination of change in temperature.

Figure 10:
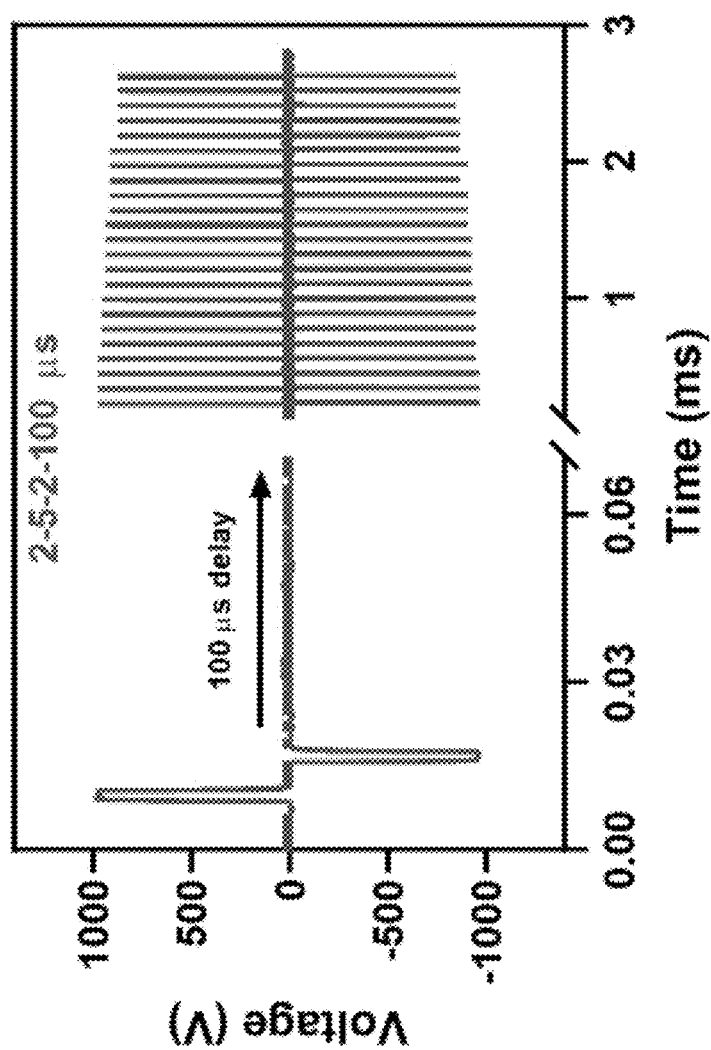
FIG. 10 is a graph showing bursts of bipolar pulses delivered across a rectangular potato tissue section.
Figures 11A, 11B, 11C:
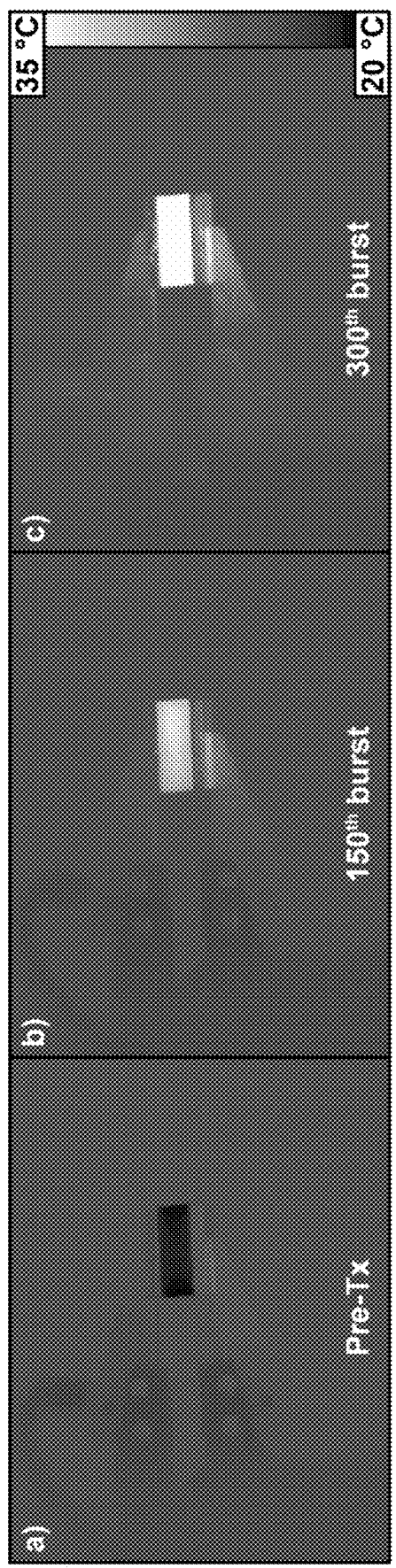
FIGS. 11A-C are photographs taken by a FLIR thermal camera to record tissue temperature during HFIRE treatment.

To demonstrate monitoring of temperature, 300 bursts of bipolar pulses (FIG. 10) were delivered across a rectangular potato tissue section to electroporate and heat the tissue simultaneously (2-5-2-100 μs burst scheme, 1000 V). A FLIR thermal camera was used to monitor temperature change (FIG. 11A-C). As seen in FIG. 11D, high voltage (HV) 2-5-2-100 μs bursts (FIG. 10) were interlaced with low voltage (LV) diagnostic FAST (1-50-1-50 μs (×84)+250-10-250-10 μs (×2)). This allows for continuous monitoring of inter-burst impedance changes (FIGS. 11E-G) throughout treatment, which can be used to determine whether to alter, stop or halt an electroporation treatment. In embodiments, such monitoring can provide for a clearer snapshot of the progress of the treatment and/or higher resolution results giving the practitioner greater confidence that a particular treatment outcome has been achieved. As determined previously, frequencies around ~1 MHz are sufficient to delineate thermal and electroporation effects in this flat plate configuration using rectangular tissue sections of L×W×H dimensions 2×2×0.7 cm. As described previously, the Fast Fourier Transform algorithm was used for analysis of the input voltage v(t) and output current i(t) in the frequency domain. Complex impedance was determined using equation 5:

$$Z(f) = \frac{V(f)}{I(f)} \quad (5)$$

A $6^{th}$ order Butterworth filter was applied to exclude frequency components above cutoff frequency 5 MHz. A linear approximation for Joule heating is assumed relating the impedance and temperature change by means of the temperature coefficient of resistance α.

$$Z_{i+1} = Z_i \cdot (1 + \alpha(T - T_0)) \quad (6)$$

As this analysis is conducted for impedance changes attributed to both electroporation and thermal effects, the term Δθ is utilized, as opposed to ΔT, to represent this relationship. Equation 6 is rewritten as:

$$Z_{i+1} = Z_i \cdot (1 + \alpha(\theta - \theta_0)) \quad (7)$$

Through algebraic manipulation, Equation 7 can be converted into Equation 8.

$$\Delta\theta = \frac{Z_{i+1} - Z_i}{Z_i} \cdot \frac{1}{\alpha} \quad (8)$$

Figure 11E:
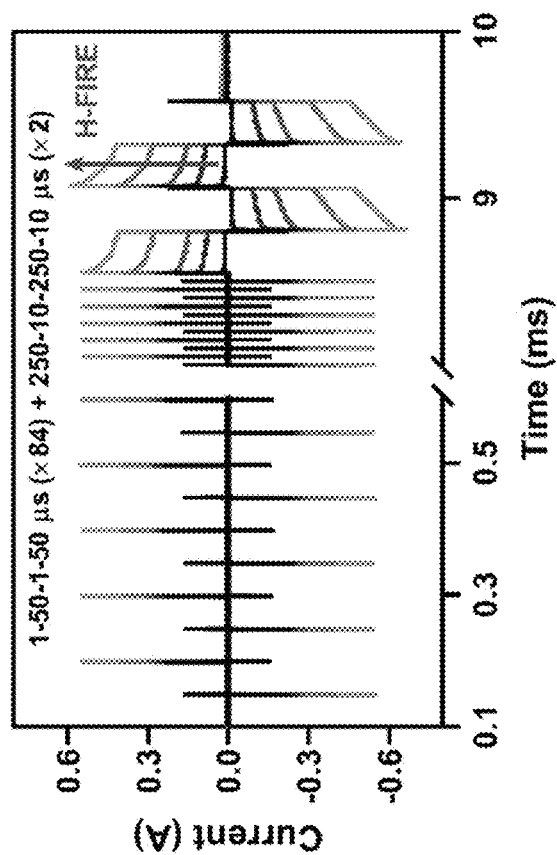
FIGS. 11D-E are schematics showing a high voltage 2-5-2-100 µs FAST pulse protocol intertwined with a low voltage diagnostic FAST protocol (1-50-1-50 µs+250-10-250-10 µs).
Figure 11D:
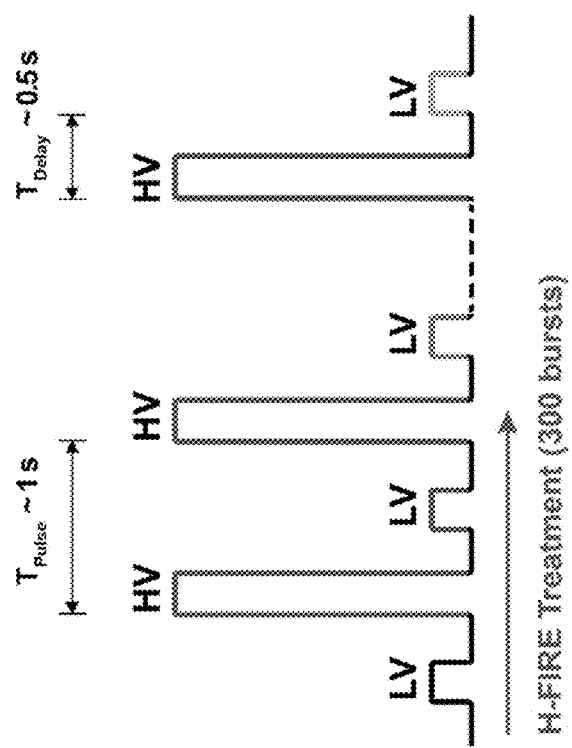
Figure 11F:
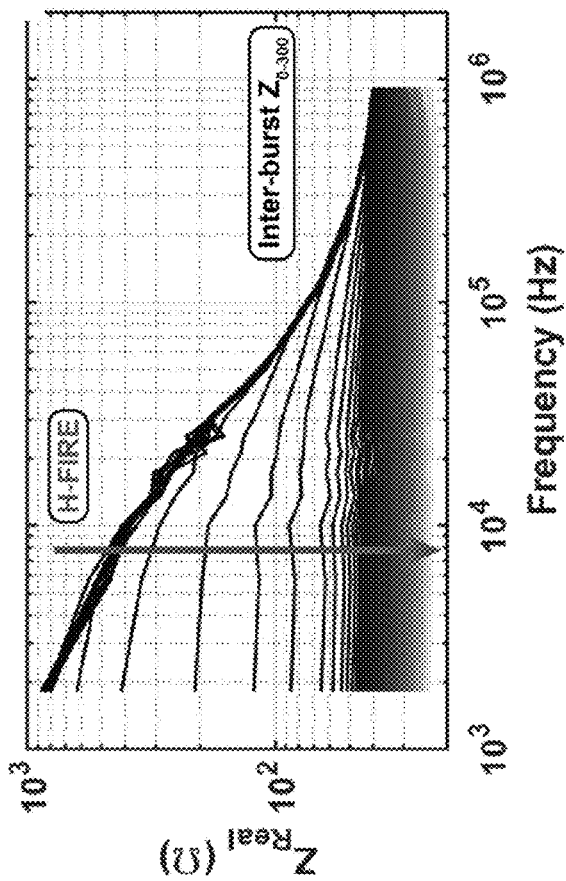
FIG. 11F is a graph showing a continual decrease in tissue impedance throughout a high-voltage treatment, where the arrow indicates the progression of treatment with high-voltage pulses (H-FIRE), which causes a decrease and flattening of tissue inter-burst impedance.
Figure 11G:
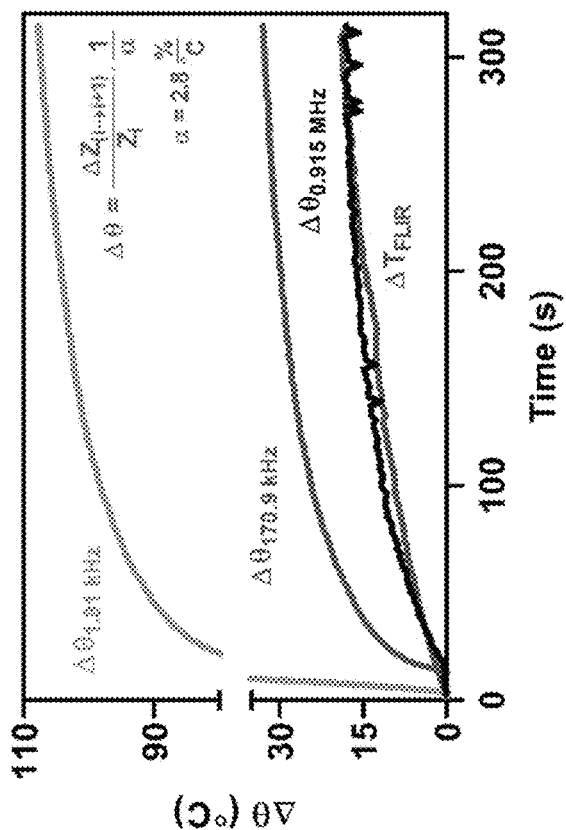
FIG. 11G is a graph showing the relationship between change in temperature and electrical impedance.

FIG. 11E shows the output electric current resulting from the LV diagnostic FAST. As the number of H-FIRE bursts increases (not shown here), the recorded diagnostic FAST electric current increases and is reflected in the frequency domain as a decrease in inter-burst impedance (FIG. 11F). Finally, the calculated Δθ demonstrates electrical impedance measured at high frequencies best approximates the true ΔT. Defining FAST-Controlled Pulsing Endpoint or Pulsing Intervals A circuit model analogy describing tissue response to pulsed electric fields is described by Voyer et al. (D. Voyer et al. "Dynamical modeling of tissue electroporation." Bioelectrochemistry 119 (2018): 98-110). Here, it can be discerned that once a cell membrane is fully electroporated (i.e., a lysed state), the electrical impedance is a function of only the intracellular resistance and extracellular resistance. This phenomenon is reflected by a theoretical flat impedance spectrum in which electroporation would no longer contribute to impedance changes (FIG. 11F). Thus, in embodiments a pulsing endpoint can be defined as achieving a flat impedance spectrum. As depicted in FIGS. 12A-D, such a pulsing protocol would largely mitigate any excessive Joule heating effects and therefore allow for larger volumes of tissue ablation without thermal damage.

In embodiments, for example, a clinical endpoint for electroporation can be defined when low-frequency impedance measurements, either a single frequency or a range of frequencies between 0.1 kHz to 500 kHz, continually decreases to a value within 20% of the reference or baseline high-frequency impedance measurements, either a single frequency or a range of frequencies between 500 kHz to 100 MHz. This is visually depicted as a flattening of the impedance spectrum during electroporation treatment.

Alternatively, or in addition, a clinical endpoint can be defined when the present low-frequency impedance measurements, either a single frequency or a range of frequencies between 0.1 kHz to 500 kHz, is unchanged compared to a prior low-frequency measurement, such as within a window of approximately 1-10%, such as within 5%. In this clinical endpoint, the low-frequency impedance measurement does not decrease to the magnitude of the high-frequency reference and does not satisfy criteria for clinical endpoint defined in above. However, the tissue is still "fully-electroporated." Pulsing in this scenario is terminated to avoid thermal damage. The following equation can be used to calculate the percent change in the present low-frequency impedance relative to the prior measurement:

$$\text{Percent change } (\%) = \frac{z_i - z_{i-1}}{z_0} \cdot 100\% \quad (9)$$

Here, $Z_0$ is the baseline low-frequency impedance measurement, $Z_i$ is the $i^{th}$ pulse/burst in the treatment, and $Z_{i-1}$ is the pulse/burst previous to the $i^{th}$ pulse/burst in the treatment.

Figure 13A:
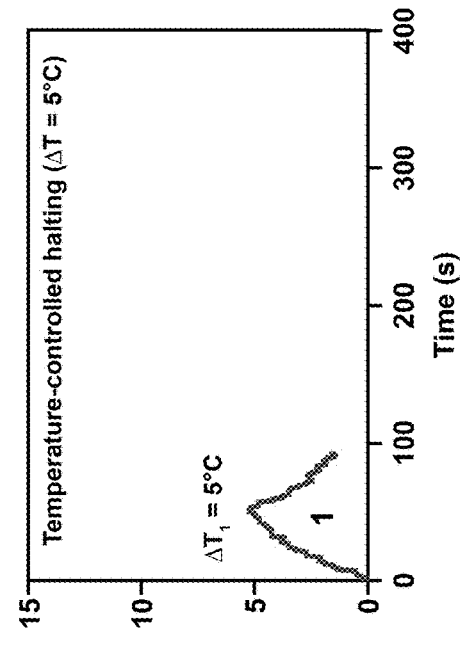
FIGS. 13A-B are graphs showing temperature controlled halting of a pulsing procedure and the corresponding impedance changes associated with administration of electroporation pulses according to a FAST-controlled pulsing method, where the treatment is paused at intervals when a temperature increase of 5° C. is achieved to allow for sufficient cooling before treatment is resumed (FIG. 13B), and the corresponding change in impedance for the treatment at various points in time for the first round of treatment defined by halting point (1) (FIG. 13A).
Figure 13B:
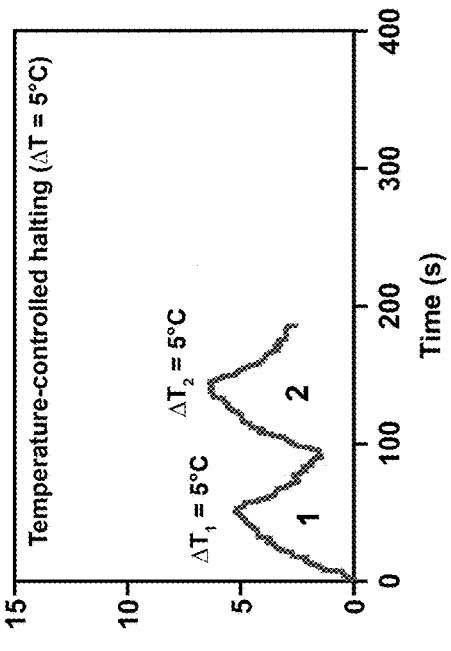
Figure 13C:
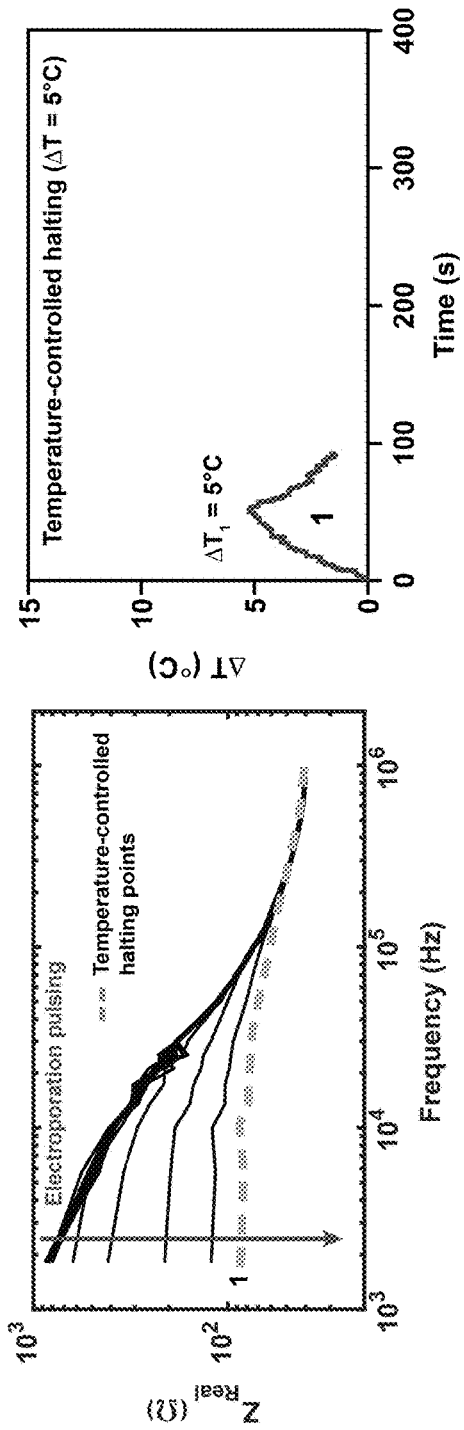
FIGS. 13C-D are graphs showing continuance of the temperature controlled halting of the FAST-controlled EP protocol from FIGS. 13A-B, with the temperature-controlled halting intervals shown in FIG. 13C (halting points 1, 2), and the corresponding impedance changes shown in FIG. 13D for round two of the treatment.
Figure 13D:
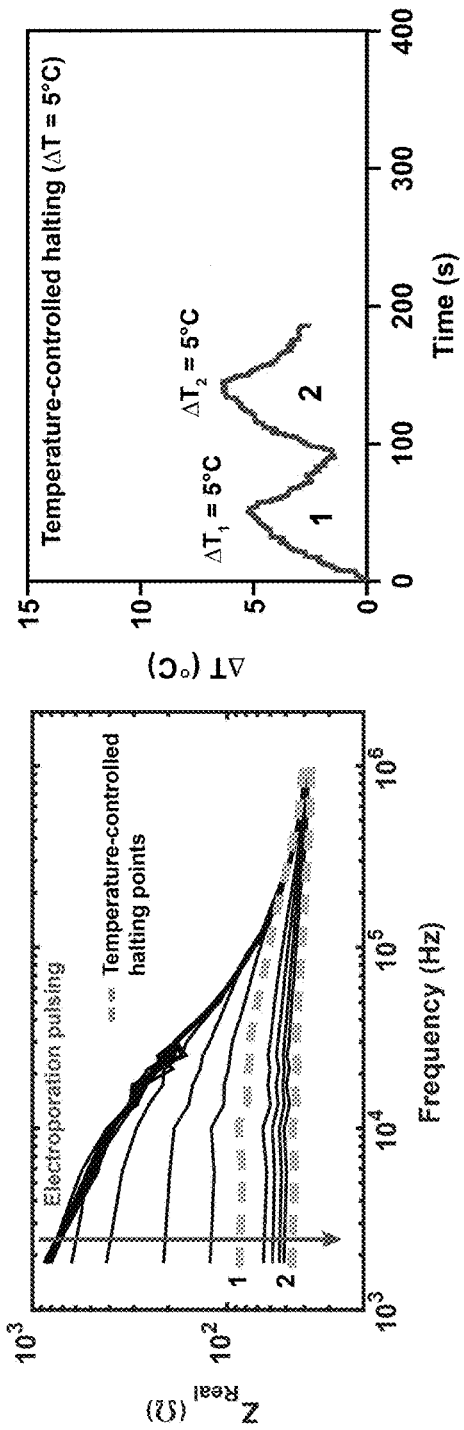

In the event the impedance profile does not saturate following a set of pulses, where the number of pulses is defined either by a predetermined number of pulses or a FAST-calculated ΔT, treatment can be adjusted, stopped, and/or halted to allow for heat dissipation to avoid or prevent excessive tissue heating. The adjusting or stopping/halting of the treatment can be performed automatically by the system and/or the system can provide prompts to the user through a graphical user interface that provide information and/or options to the user on how to proceed. Once the tissue temperature has reached a desirable level, pulsing can continue. This methodology can be repeated until the pulsing endpoint is met (flat impedance profile). A theoretical, representative pulsing profile for which multiple pulsing sets might be used is depicted in FIGS. 13A-B. In this schematic, a pulsing condition of ΔT=5° C. is set, though this condition can be modified as needed. This condition can be controlled as a ΔT, pre-defined number of pulses, or other timing criteria.

Figures 13E, 13F:
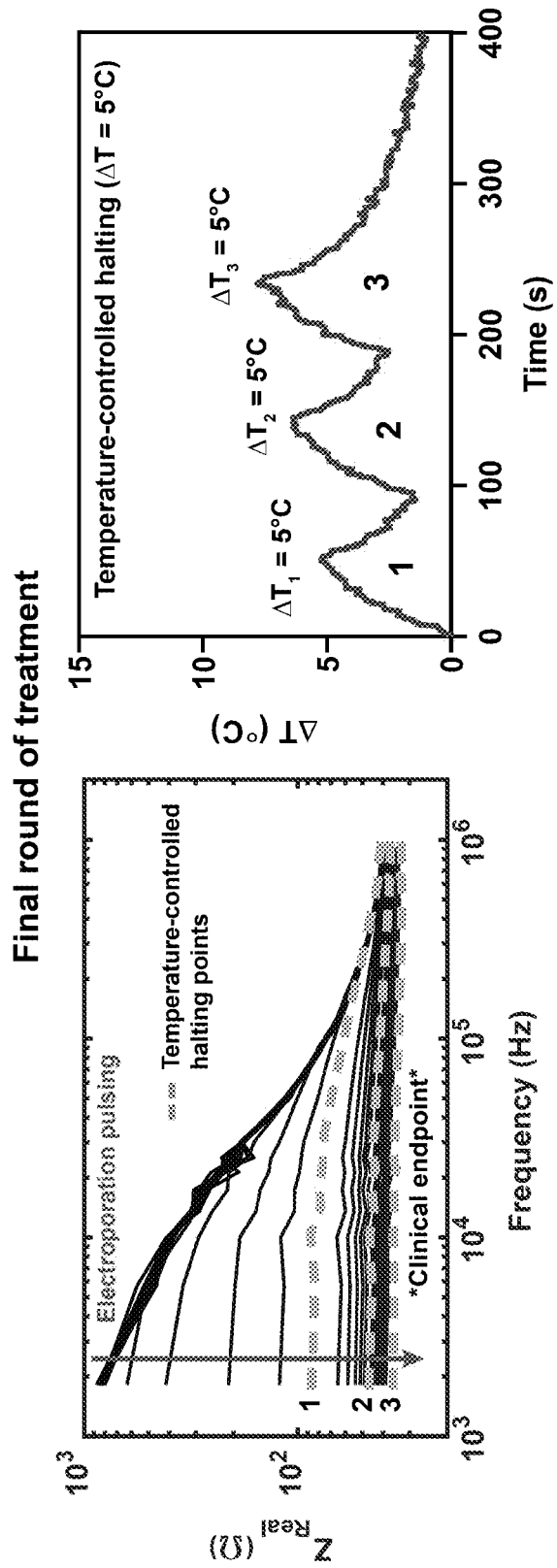
FIGS. 13E-F are graphs showing continuance of the temperature controlled halting of the FAST-controlled EP protocol from FIGS. 13A-D, with the temperature-controlled halting intervals shown in FIG. 13E (halting points 1 and 2 and stopping point 3), and the corresponding impedance changes (FIG. 13F) for the final round of the treatment, where the clinical endpoint is indicated by obtaining a flat impedance profile (as shown by convergence of the curve).

In embodiments, for example, the halting/pausing of electroporation treatment can be defined as delivering a pre-determined number of pulses/bursts (0-1,000) across one or more electrode/probe pair combinations. Once this value is reached, treatment can be paused for a pre-determined time (e.g., 0-600 s), as shown in FIGS. 13A-B. This process can then be repeated (FIGS. 13C-F) until the clinical endpoint, such as determined from diagnostic FAST impedance measurements, is reached (FIG. 13F).

Alternatively, or in addition, the halting/pausing of electroporation treatment can be defined as reaching a pre-determined increase in temperature (e.g., 0-50° C.) across one or more electrode/probe pair combinations. This increase in temperature is measured using either a temperature measurement device (fiber optic temperature sensor, thermocouple, etc.) or by using high-frequency impedance measurements to predict temperature change. Once this temperature increase is reached, treatment will be paused for a pre-determined time (e.g., 0-600 s) or until a temperature decrease (e.g., 0-50° C.) criteria is met. This process will be repeated until the clinical endpoint, such as determined from diagnostic FAST impedance measurements, is reached.

System for Administering FAST Protocol

Figure 23:
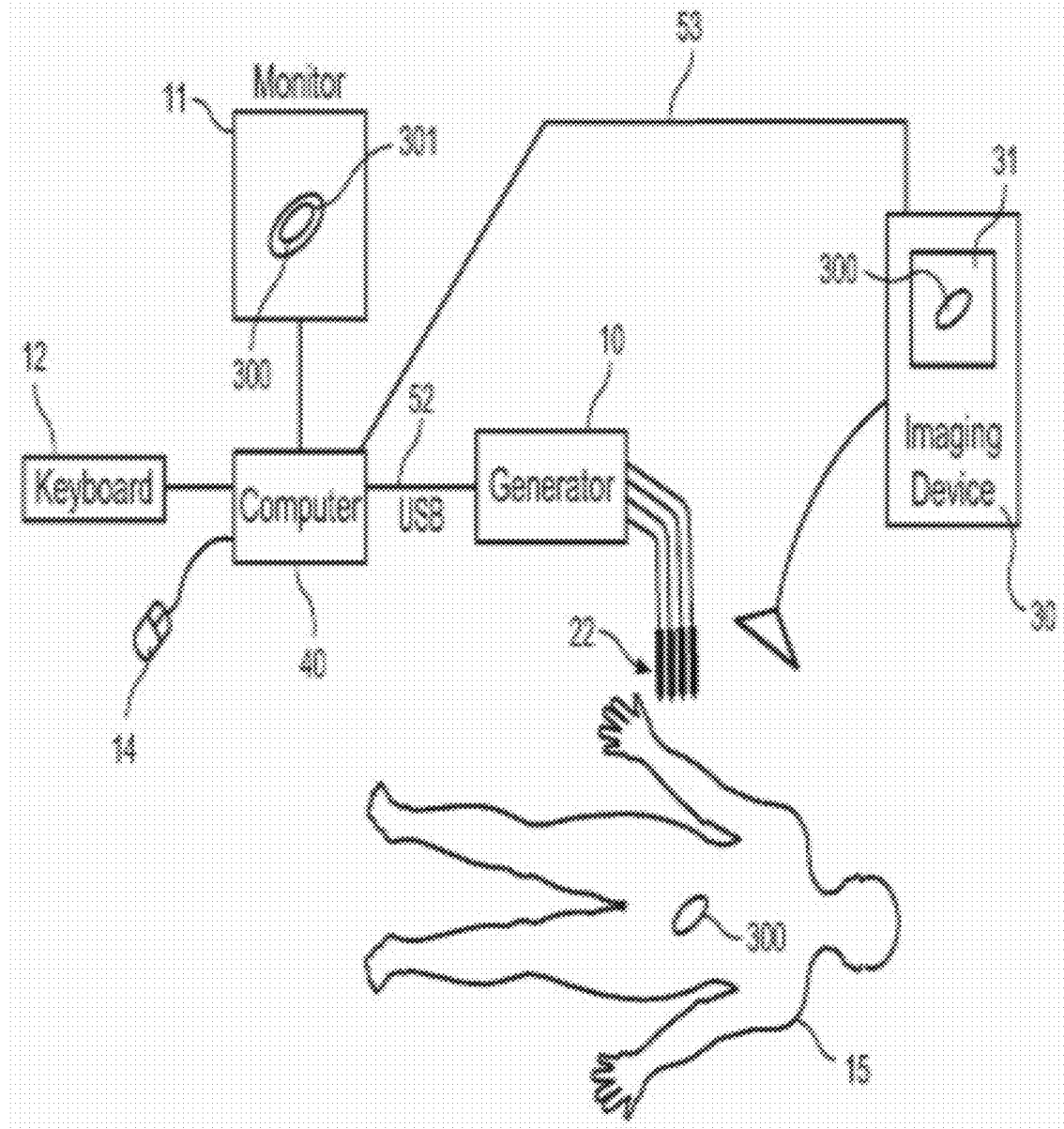
FIG. 23 is a schematic diagram of a representative system of the invention.
Figure 24:
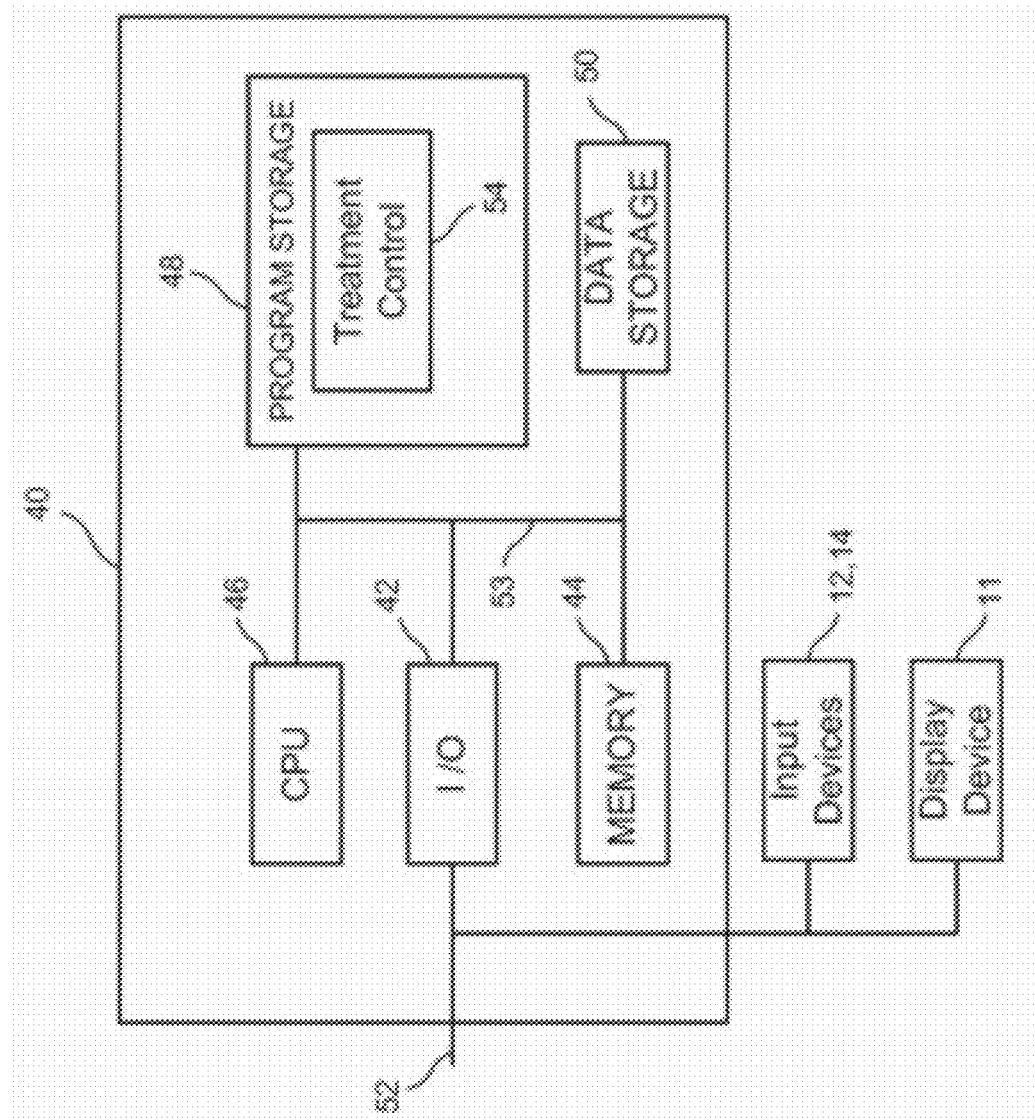
FIG. 24 is a diagram of a representative treatment control computer of the invention.

Embodiments of the present invention can include one or more components as illustrated in FIGS. 23 and 24. For example, in embodiments, one or more probes can be used to deliver therapeutic energy and are powered by one or more voltage pulse generator 10 that generates high or low voltage pulses as therapeutic energy, diagnostic FAST or therapeutic FAST, such as pulses capable of electroporating (e.g., irreversibly electroporating) the tissue cells. In embodiments, the voltage pulse generator(s) can include any number of receptacles for receiving up to any number of individual probes, which probes are adapted to be plugged into the respective receptacle. In embodiments, the voltage pulse generator(s) can have any number of receptacles for receiving for example from 1-20 probes.

For example, a treatment protocol according to the invention could include a plurality of electrodes disposed on any number of probes. According to the desired treatment and/or data acquisition pattern, the plurality of electrodes can be disposed in various positions relative to one another. In a particular example, a plurality of electrodes can be disposed in a relatively circular or square or rectangular pattern. Any configuration of electrodes is possible and the arrangement need not be circular, square or rectangular, but any shape periphery can be used, including triangular, depending on the area to be treated, including any regular or irregular polygon shape, including convex or concave polygon shapes. Any of the electrodes can be a ground electrode and any of the other electrodes in the plurality can be energized. Any number of electrodes can be in the plurality such as from about 1 to 20. Indeed, even 3 electrodes can form a plurality of electrodes, or 4 electrodes can be disposed in a manner to provide two electrode pairs (each pair comprising one ground and one electrode capable of being energized). During treatment, methods of treating can involve energizing the electrodes in any sequence, such as energizing one or more electrode simultaneously, and/or energizing one or more electrode in a particular sequence, such as sequentially, in an alternating pattern, in a skipping pattern, and/or energizing multiple electrodes but less than all electrodes simultaneously, for example.

In embodiments, each probe includes either a monopolar electrode or bipolar electrodes. The amount of exposure of an active portion of the electrode can be adjusted by retracting or advancing an insulating sleeve relative to the electrode. See, for example, U.S. Pat. No. 7,344,533, which is incorporated by reference herein in its entirety. The pulse generator(s) are connected to a treatment control computer 40 having input devices such as keyboard 12 and a pointing device 14, and an output device such as a display device 11, including a graphical user interface (GUI), for viewing information obtained from the FAST protocol. One or more probe is used to treat a lesion, tissue, or area/region of interest (ROI) 300 inside a patient 15 and/or to perform diagnostic and/or therapeutic FAST monitoring in conjunction with such treatment. An imaging device 30 includes a monitor 31 for viewing the lesion 300 inside the patient 15 in real time and for monitoring the diagnostic and/or therapeutic FAST monitoring. Examples of imaging devices 30 include ultrasonic, CT, MRI and fluoroscopic devices as are known in the art.

The present invention includes computer software (treatment monitoring module 54) which assists a user to plan for, execute, and review the results of a medical treatment procedure, as will be discussed in more detail below. For example, the treatment monitoring module 54 assists a user to plan for a medical treatment procedure by enabling a user to more accurately position each of the probes 22 of the therapeutic energy delivery device 20 in relation to the tissue, ROI, or lesion 300 in a way that will generate the most effective treatment zone, and/or provide options for the practitioner/user concerning whether and how to adjust treatment, and/or halt or stop treatment based on the impedance changes being measured by way of the diagnostic and/or therapeutic FAST monitoring. The treatment monitoring module 54 can display the progress of the treatment, such as monitoring with FAST, in real time and can display the results of the treatment procedure and/or results of the diagnostic or therapeutic FAST after it is completed. This information can be displayed in a manner such that it can be used for example by a physician to determine whether the treatment was successful and/or whether it is necessary or desirable to re-treat the patient, continue to treat the patient, or stop treatment based on the FAST results.

Any non-transitory computer-readable media can be used to store the software and/or the output of the software for a particular treatment protocol.

For purposes of this application, the terms "code", "software", "program", "application", "software code", "computer readable code", "software module", "module" and "software program" are used interchangeably to mean software instructions that are executable by a processor. The "user" can be a physician or other medical professional. The treatment monitoring module 54 executed by a processor outputs various data including text and graphical data to the monitor 11 associated with the generator 10.

Referring now to FIG. 24, the treatment control computer 40 of the present invention manages monitoring of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment monitoring module 54 which includes a user interface module that interacts with the user in monitoring, executing and reviewing the result of a treatment. Any of the software program modules in the program storage 48 and data from the data storage 50 can be transferred to the memory 44 as needed and is executed by the CPU 46.

Figure 27:
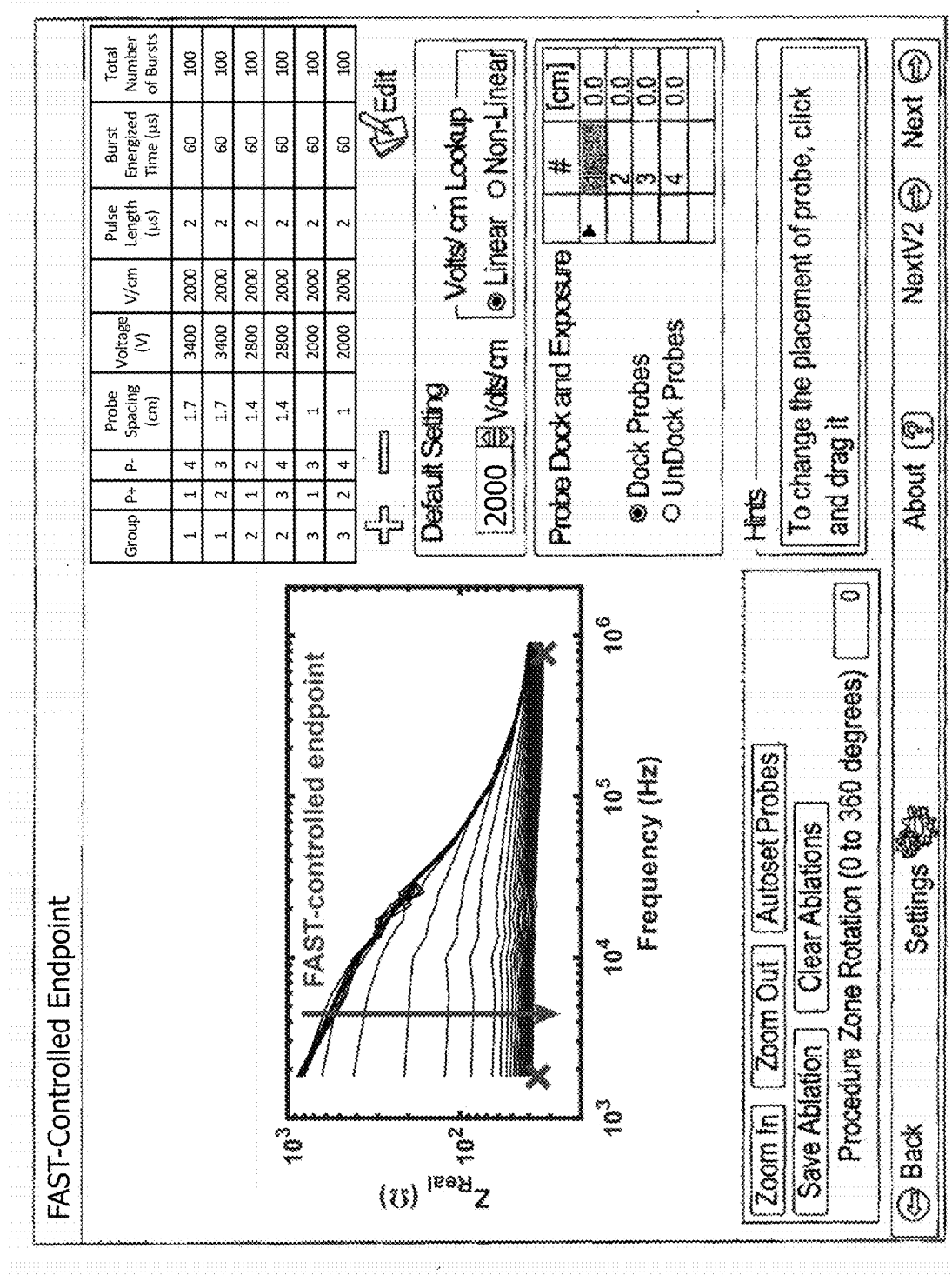
FIG. 27 is an illustration showing an example graphical user interface (GUI) for administering and monitoring diagnostic and/or therapeutic FAST protocols.

In one embodiment, the computer 40 is built into the voltage generator(s) 10. In another embodiment, the computer 40 is a separate unit which is connected to the voltage generator(s) through the communications link 52. In a preferred embodiment, the communication link 52 is a USB link. In one embodiment, the imaging device 30 is a stand-alone device which is not connected to the computer 40. In the embodiment as shown in FIG. 23, the computer 40 is connected to the imaging device 30 through a communications link 53. As shown, the communication link 53 is a USB link. In this embodiment, the computer can analyze the FAST impedance measurements and/or spectra obtained and the computer 40 can display this information on the monitor 11. In this embodiment, the FAST information/analysis/ results obtained and/or recommendations or options for whether and how to proceed with treatment can be provided on a GUI and presented to the user (FIG. 27).

It should be noted that the software can be used independently of the pulse generator(s) 10. For example, the user can monitor the treatment by way of FAST in a different computer as will be explained below and then save the treatment parameters to an external memory device, such as a USB flash drive (not shown). The data from the memory device relating to the treatment parameters can then be downloaded into the computer 40 to be used with the generator 10 for treatment. For example, the data can be evaluated by a human to determine or estimate favorable treatment protocols for a particular patient or programmed into a device for implementing the particular protocol.

Figure 25:
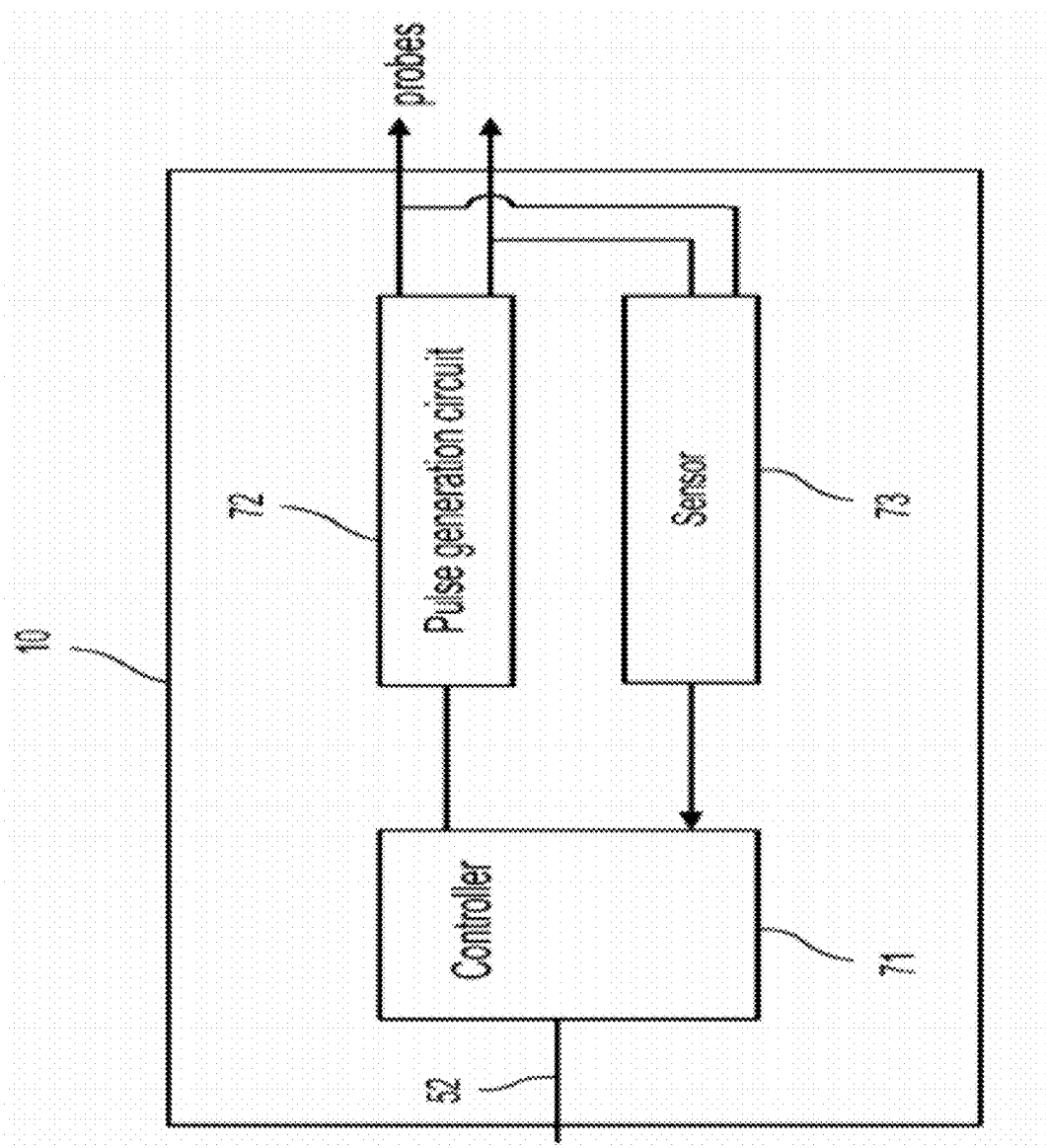
FIG. 25 is diagram illustrating details of the generator shown in the system of FIG. 23.

FIG. 25 illustrates one embodiment of a circuitry to detect an abnormality in the applied pulses such as a high current, low current, high voltage or low voltage condition. This circuitry is located within the generator 10 (see FIG. 23). A USB connection 52 carries instructions from the user computer 40 to a controller 71. The controller can be a computer similar to the computer 40 as shown in FIG. 24. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes are shown. However, the generator 10 can accommodate any number of probes/electrodes (e.g., from 1-10, such as 6 probes) and energizing multiple electrodes simultaneously for customizing the shape of the ablation zone. In the embodiment shown, the pulses are applied one pair of electrodes at a time, and then switched to another pair. The pulse generation circuit 72 includes a switch, preferably an electronic switch, that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes. The treatment monitoring module 54 can further include a feature that tracks the treatment progress and provides the user with an option to automatically retreat for low or missing pulses, or over-current pulses (see discussion below). Also, if the generator stops prematurely for any reason, the treatment monitoring module 54 can restart at the same point where it terminated, and administer the missing treatment pulses as part of the same treatment. In other embodiments, the treatment monitoring module 54 is able to detect certain errors during treatment, which include, but are not limited to, "charge failure", "hardware failure", "high current failure", and "low current failure".

Figure 26:
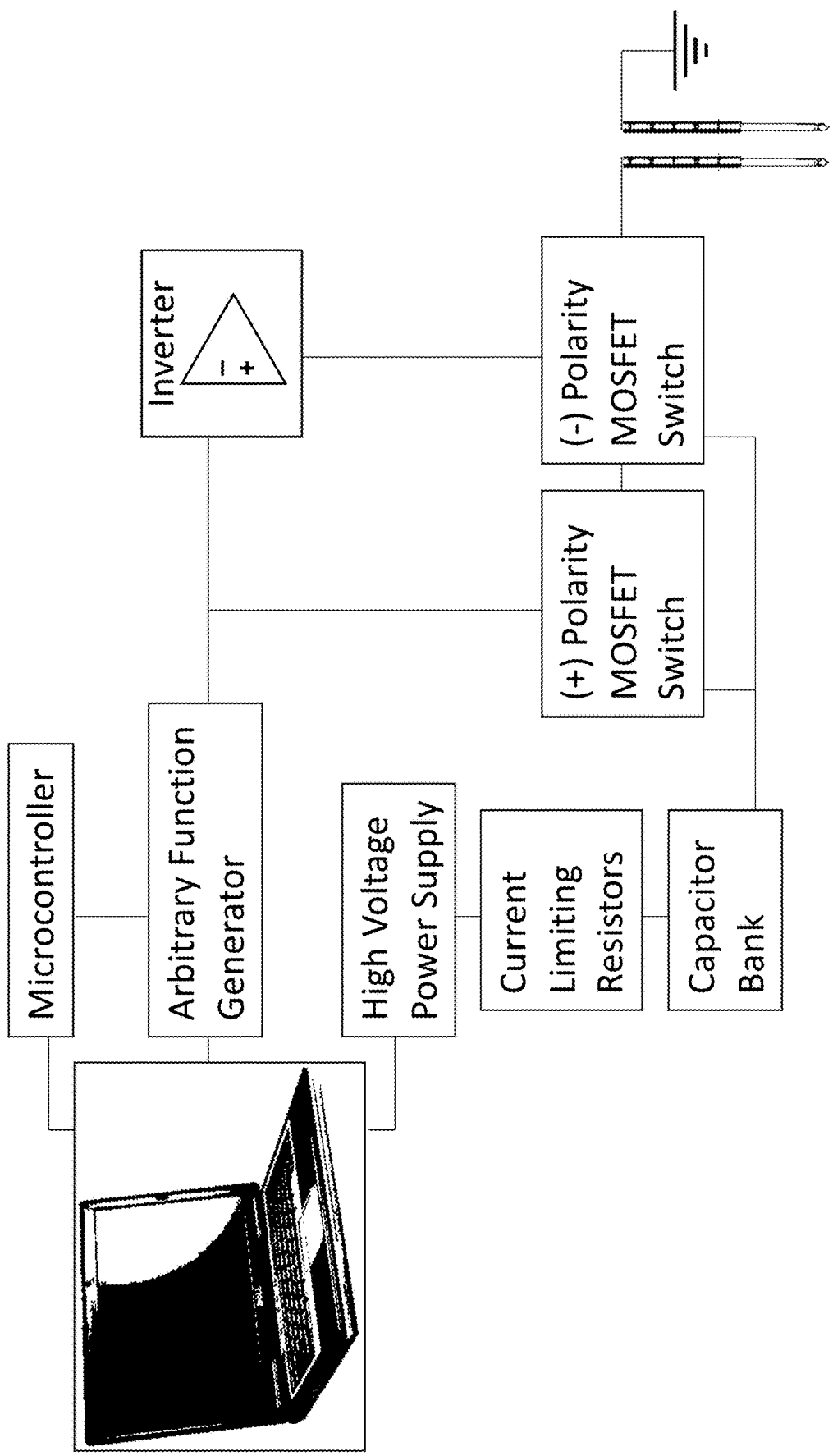
FIG. 26 is a diagram of a system for implementing high-frequency, bipolar pulses for tissue electroporation.

In another embodiment, an electronic drive system for delivering bipolar electroporation signals is schematically depicted in FIG. 26. An arbitrary function generator (e.g., Tektronix AFG 3011) and/or associated software can be programmed to output the desired waveform(s). The burst width, interval between bursts, and total number of bursts can be externally controlled by a microcontroller (e.g., Arduino Duemilanove) through the general purpose input/output (GPIO) pins. The output signal can be simultaneously fed through both positive polarity and negative polarity high voltage MOSFET switches (IXYS Colorado HV 1000). The signal into the negative polarity can be inverted using an amp with a desired slew rate in order to properly sequence the amplification of the positive and negative polarity pulses with or without delay. The input power to each HV 1000 is maintained by a high voltage sequencer, which can regulate voltage up to +/−15,000 V. In order to increase current storage, an external capacitor bank can be included. The total capacitance of the bank can be adjusted depending on the desired voltage and current output or electrode spacing. This system allows for a flexible treatment program that may be tailored to meet a patient's individual needs.

Other systems are available in the literature for generating bipolar pulses, and the invention should not be limited to the system described above. For example, De Vuyst et al. built a generator around an NE555 timer configured as an astable multivibrator capable of producing up to 50 kHz bipolar pulses. De Vuyst, E., M. De Bock, E. Decrock, M. Van Moorhem, C. Naus, C. Mabilde, and L. Leybaert, In situ bipolar Electroporation for localized cell loading with reporter dyes and investigating gap junctional coupling. Biophysical Journal, 2008. 94(2): p. 469-479. However, the frequency of the pulses administered according to embodiments of the invention are an order of magnitude greater, which is easily met by the bandwidth of the AFG 3011. Additionally, the MOSFET switches provide an excellent means to produce high-frequency pulses for high voltage switching. However, MOSFETs are not the only semiconductor devices that can be utilized to produce a pulse. Bipolar Junction Transistors (BJTs), Insulated Gate Bipolar Transistors (IGBTs), and Junction Field Effect Transistors (JFETs) are examples of some of the semiconductor devices that may be used to produce an output pulse.

Embodiments of the invention include an electrical energy monitoring system comprising: one or more probes/electrodes; one or more low voltage generator; one or more high voltage generator; wherein the low voltage and high voltage generators are in operable connection with the probes/electrodes; wherein the low and/or high voltage generators are capable of generating a plurality of electrical pulses; wherein the system is configured to cause electroporation of tissue, obtain one or more low-frequency and/or high-frequency impedance measurement and/or impedance spectrum, identify any change in impedance relative to a reference impedance measurement, and based on the change determine whether a desired endpoint of treatment is reached.

For example, a treatment monitoring system according to the invention for administering electrical pulses can comprise: one or more electrical pulse generator(s); one or more probe(s) capable of connection with the electrical pulse generator(s); one or more controller(s) capable of controlling one or more of the electrical pulse generator(s) and/or one or more of the probe(s) to: administer a plurality of electrical pulses; obtain one or more impedance measurement or spectrum; and identify any impedance change relative to a reference impedance measurement. Additionally, treatment monitoring systems for administering electrical pulses according to embodiments can comprise: one or more probe configured to deliver electrical energy; a low-voltage pulse generator, and optionally a high-voltage pulse generator; an impedance analyzer in communication with one or more of the probes; wherein the impedance analyzer is configured to: obtain one or more impedance measurement or spectrum; and identify any impedance change relative to a reference impedance measurement; a treatment monitoring module configured to adjust, halt or stop delivering of the electrical energy based on the impedance change.

The treatment control module may control the delivery of electrical energy based on the various functions/outputs of the FAST technology as described above. Also, the module is connected to GUI allowing a user to receive real-time feedback on the FAST outputs and provides user options to adjust/halt/stop/continue delivery of electrical pulses based on this feedback.

FAST Board

Figure 14:
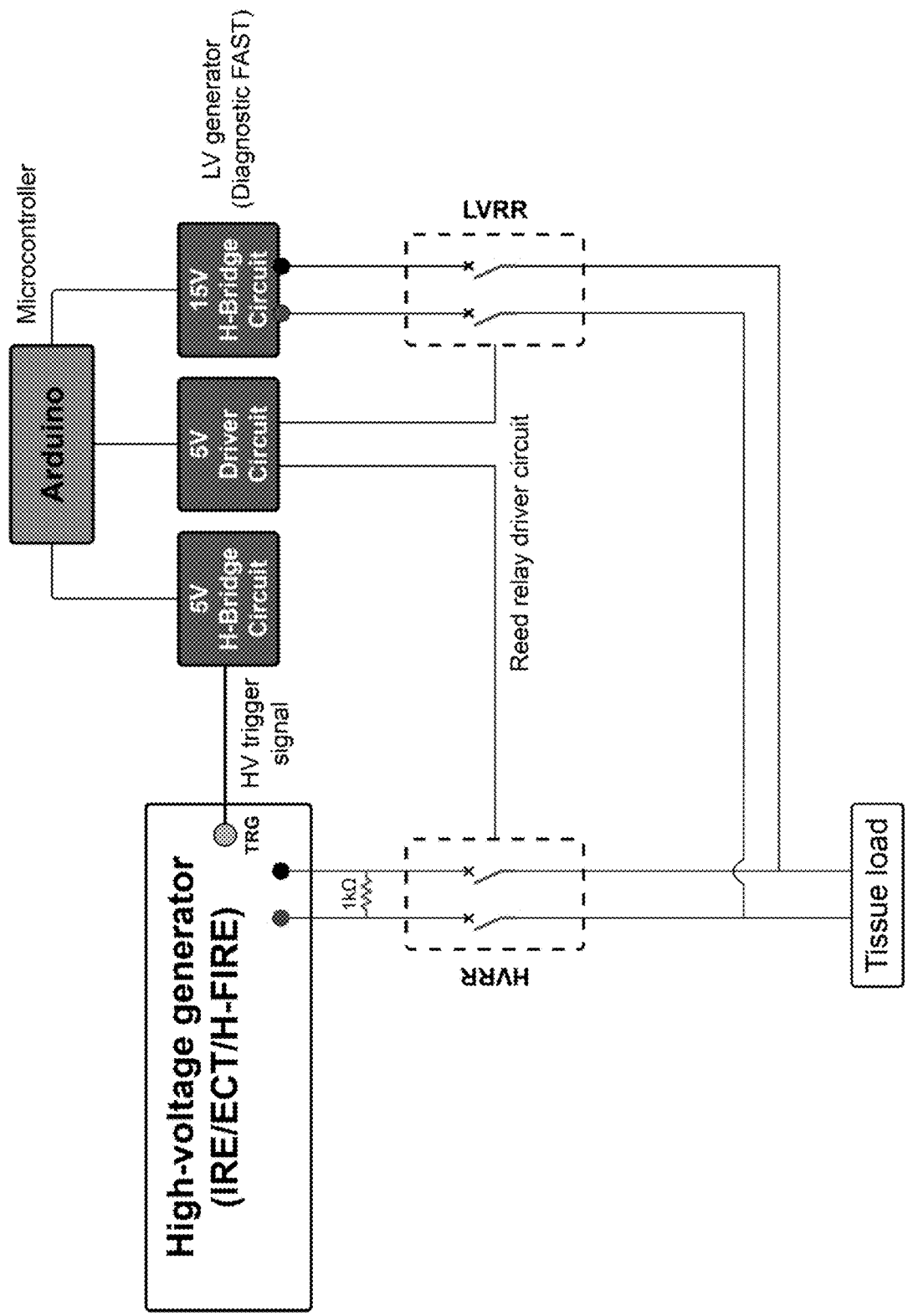
FIG. 14 is a schematic diagram depicting a representative FAST board comprising a microcontroller, a high-voltage pulse generator, 4 Reed relays, an H-Bridge low-voltage pulse generator, and driving circuitry (2 additional H-Bridge circuits).

A FAST board was developed to interlace high-voltage ECT/IRE/H-FIRE pulses with low-voltage diagnostic FAST pulses. This board comprises a microcontroller, a high-voltage pulse generator, one or more relays (here, 4 Reed relays), an H-Bridge low-voltage pulse generator, and driving circuitry (with two additional H-Bridge circuits). FIG. 14 shows a schematic of a representative system/device. In particular embodiments, the device can comprise an Arduino Uno R3 (Digikey, 1050-1041-ND), four Reed Relays 5503-05-1 (Digikey, 306-1300-ND), three commercial H-Bridge Circuits TB6612FNG (Digikey, 1568-1756-ND), a custom high-voltage pulse generator (EPULSUS-FBM1-5), and two resistors in series (500 Ohm, 50 W—Digikey, MP850-500-F-ND). The part numbers are listed as examples and are not intended to limit the invention. In embodiments, the FAST board can be incorporated into an electrical pulse generator or provided as a separate component.

Figure 15:
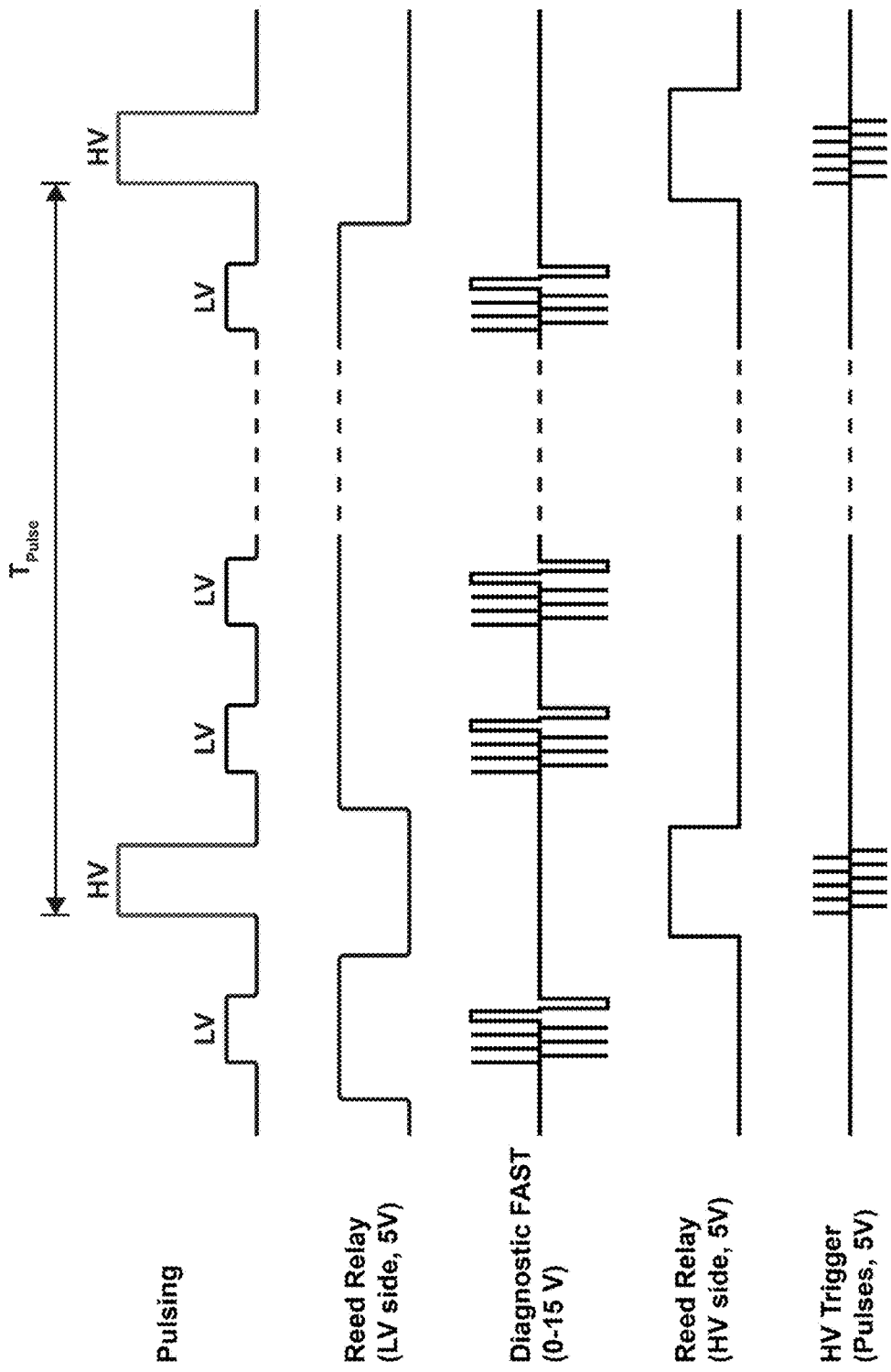
FIG. 15 is a schematic depicting exemplary microcontroller timing protocols for low voltage and high voltage pulsing.
Figure 17:
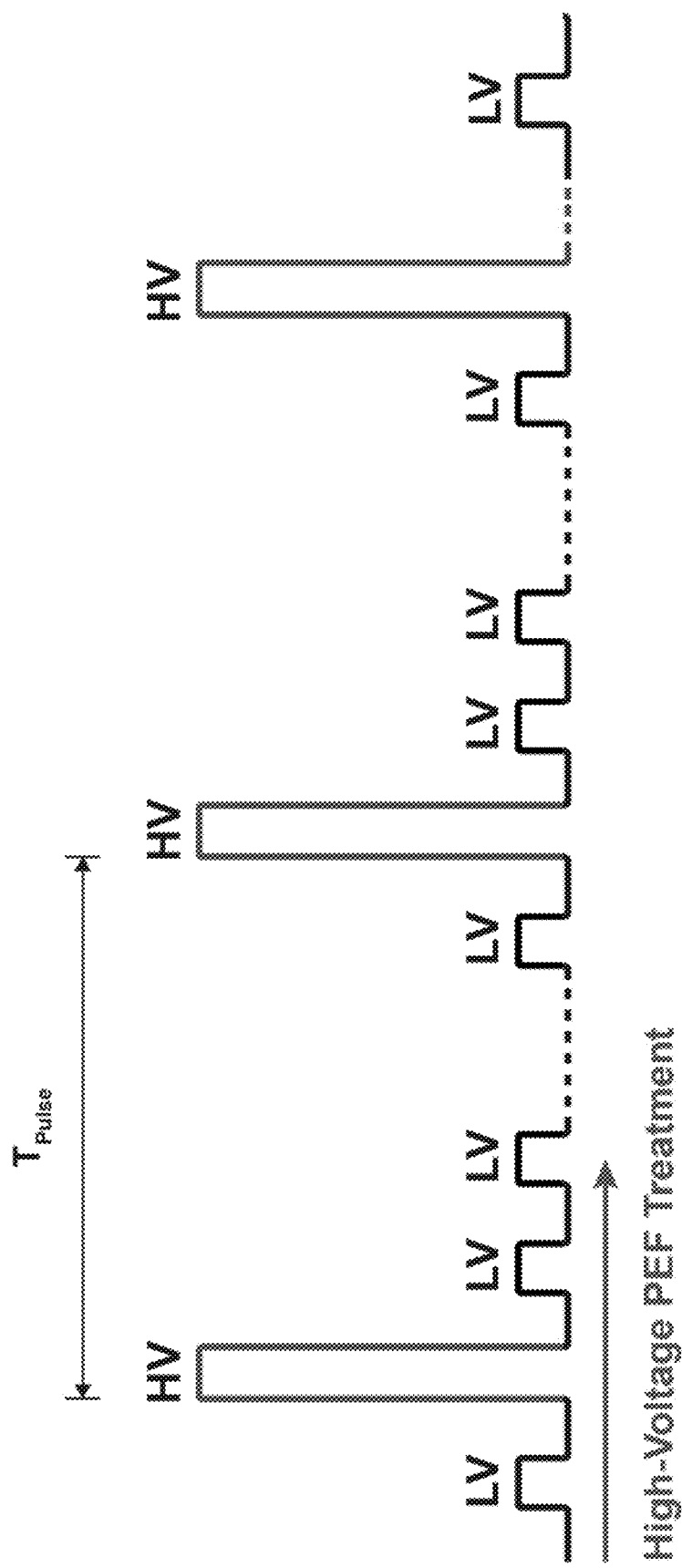
FIG. 17 is a schematic showing a pulsing protocol in which low-voltage pulses are interleaved between high-voltage pulses.

In the device, the microcontroller (Arduino Uno) is used to synchronize all trigger signals. The Arduino Uno is a logic board and cannot supply the necessary current to sustain a 5V/15V signal. Therefore, commercial H-Bridge circuits were used in combination with power supplied by an external DC power supply to produce the 5 V and 15 V signals needed to drive the Reed relays, high-voltage pulse generator, and low-voltage diagnostic FAST pulse generator. In embodiments, the timing is such that there is ~500 ms delay between the high-voltage and low-voltage pulsing. Any amount of delay between administering high-voltage and low-voltage pulses can be used depending on a particular application. In embodiments, the delay between a high-voltage pulse and a low-voltage pulse is preferably at minimum of about 1 ms and up to however long is desired, such as about 10 s. By adjusting the delay, a single low-voltage pulse can be applied between the high-voltage pulses or a plurality of low-voltage pulses, such as 1,000 low-voltage pulses can be applied (FIGS. 15 and 17).

At all times, the Reed relays form an open circuit unless triggered by the microcontroller. In embodiments, the microcontroller can trigger in the following order:
1) Reed relays on the low-voltage circuit (LVRR), are triggered to close thereby completing the low-voltage circuit;
2) the low-voltage pulse generator is triggered to deliver diagnostic FAST;
3) the LVRR trigger signal is ceased, forming an open circuit on both LV and HV sides;
4) after approximately 500 ms, the Reed relays on the high-voltage circuit (HVRR) are triggered to close thereby completing the high-voltage circuit;
5) the high-voltage pulse generator is triggered to deliver electroporation pulses.

The use of Reed Relays allows for the physical isolation of the low voltage and high voltage circuitry, so as to not pulse high voltage into the low voltage side. One H-bridge circuit is used to drive the EPULSUS high-voltage generator with a 5V monopolar trigger signal. In the event the Reed Relays malfunction and the HVRR do not close, a 1 kW resistor load (here, two 500 W resistors placed in series) is placed in parallel with the tissue load to prevent high-voltage pulsing into an open circuit. A second H-Bridge is used to drive four reed relays each at 5V. The final H-Bridge is used to deliver 15V diagnostic FAST across the tissue load. The microcontroller synchronizes the timing of these circuits. An exemplary timing protocol is given in FIG. 15.

Figure 16B:
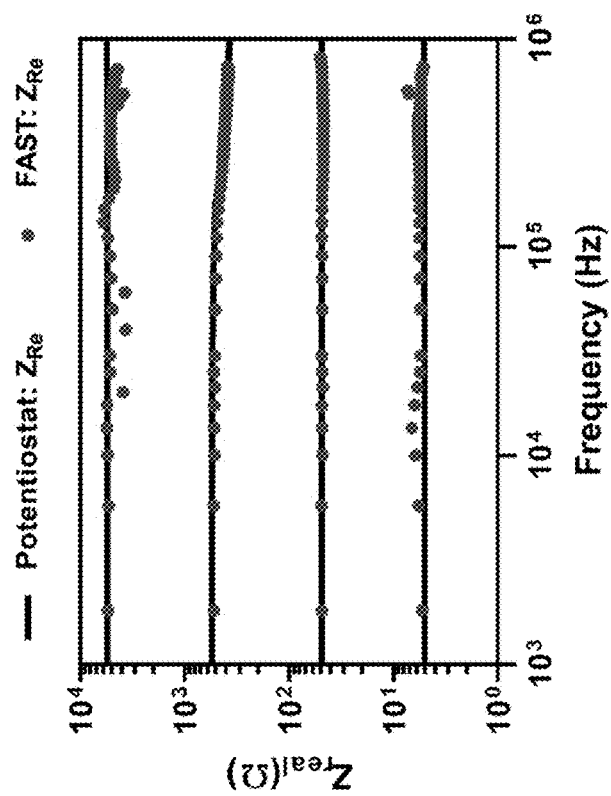
FIG. 16B is a graph comparing the real part of the impedance of the FAST board and that from a commercial potentiostat.
Figure 16A:
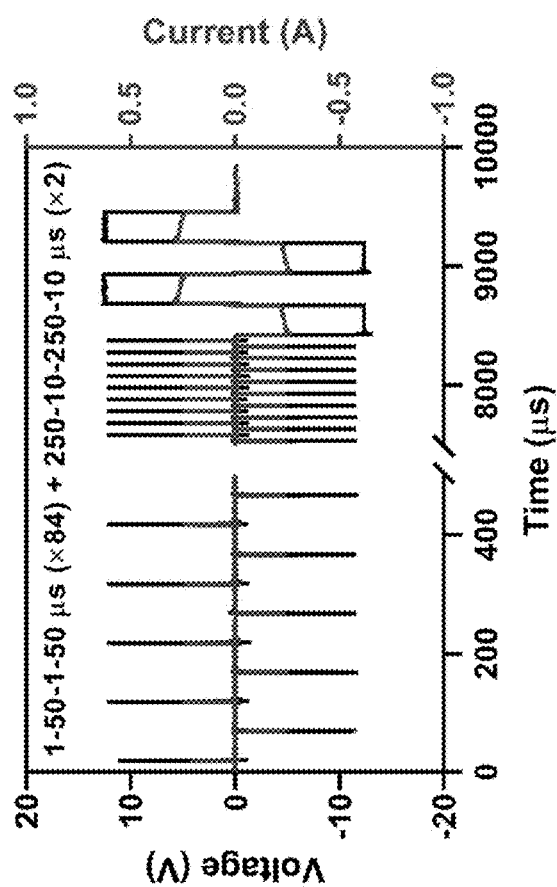
FIG. 16A is a graph showing the diagnostic FAST pulse protocol used during validation of the FAST board.

Validation of the FAST board was conducted using four resistors of varying resistance: 5, 50, 500, and 5,000 W. A diagnostic FAST comprising a pulsing scheme of 1-50-1-50 μs (×84)+250-10-250-10 μs (×2) (FIG. 16A) was used and good agreement between the real part of the impedance of the FAST board and that from a commercial potentiostat was shown (FIG. 16B).

The FAST board enables synchronous pulsing as demonstrated in FIG. 17. Multiple (1-1000) low-voltage diagnostic FAST pulses can be interleaved in between high-voltage pulses. This method of pulsing can be repeated for any portion of or the duration of treatment so as to monitor impedance changes throughout treatment.

Other Potential Applications for FAST

Figure 1D:
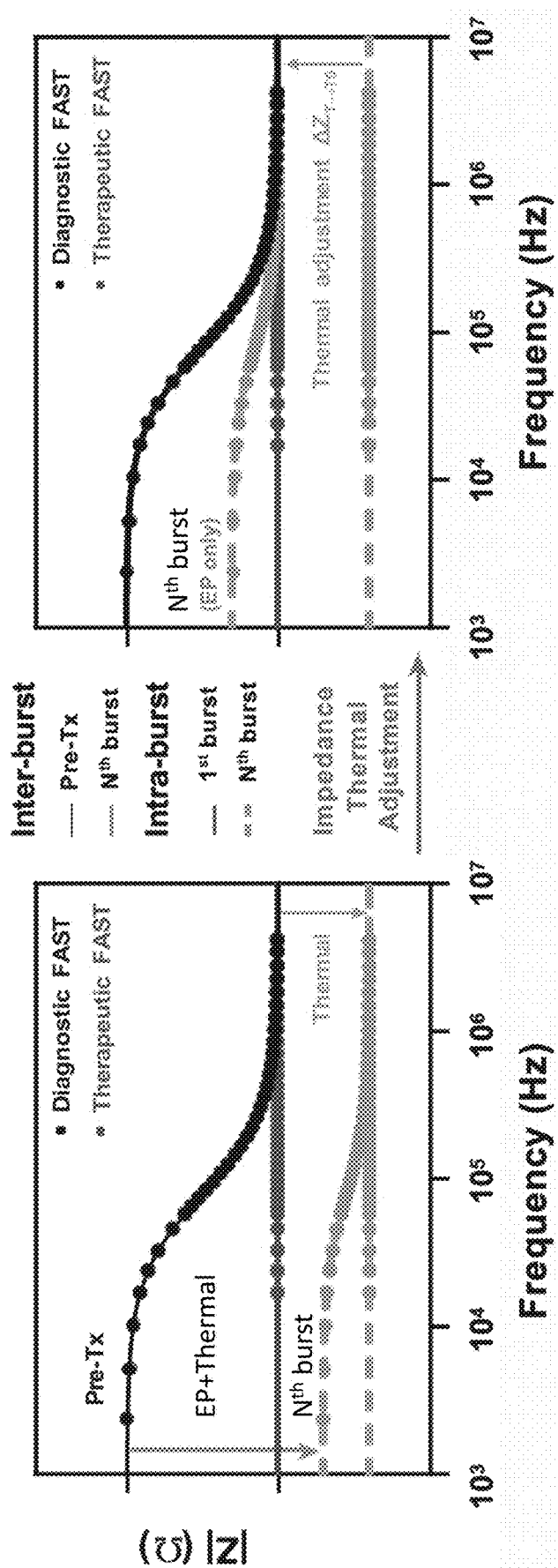
FIG. 1D is a graph depicting the thermal adjustment to the impedance spectrum.

Extrapolating these findings to clinical EP, it is possible to describe an EBT where a series of diagnostic FAST interlaced with a series of therapeutic FAST are used to measure high-bandwidth intra-burst and inter-burst impedance throughout treatment. This combination of pulsing can be used to continually monitor the absolute change in tissue impedance with a high-frequency reference to subtract thermal effects, like that shown in FIG. 1D. Here, Fourier Analysis SpecTroscopy is introduced as a methodology to measure inter-burst impedance and high-voltage intra-burst impedance, represented as dots in the impedance spectrum in FIG. 1D, using modified EBT waveforms with subsequent Fourier analysis. As high-frequency currents are less susceptible to EP effects, these impedance changes can be used to delineate EP effects from thermal effects.

Once temperature effects on impedance are determined, this impedance can then be subtracted to effectively isolate changes in tissue impedance due solely to EP. In a flat plate configuration, this may be further extended to utilizing high frequency impedance to predict and monitor temperature rise during treatment. Finally, recovery dynamics (inter-burst and intra-burst impedance) can be further explored. Previously, Neal et al. described the use of a combination low-frequency (kHz) and high-frequency (MHz) impedance to approximate the nonelectroporated and fully electroporated tissue conductivity for purposes of predicting the electric field distribution and informing treatment planning algorithms. In contrast, here, the inventors have found that change in impedance can be used for determining whether and how to proceed with electroporation therapy. Here, a diagnostic FAST can be utilized for such an approximation, and therapeutic FAST to verify the intra-burst impedance spectrum saturates to this high frequency impedance, as was the case for the potato tissue tested in FIGS. 8A-G.

Furthermore, cell lysis accomplished with therapeutic FAST can potentially be monitored using the β-dispersion hypothesis. The intra-burst impedance spectrum saturates to that of $R_e$ $R_i$ once a high enough voltage is reached, fully bypassing the cell membrane. Once a cell is lysed (i.e. cell membrane is fully compromised), cell lysis is confirmed once the intra-burst impedance spectrum is matched to the inter-burst impedance spectrum. Though cell death with IRE varies from cell lysis—necroptosis—apoptosis, this phenomenon again presents novel opportunities of monitoring treatment progression. Tissue impedance changes during EBTs are indicative of treatment progression from baseline. Therefore, Fourier Analysis SpecTroscopy (FAST) is provided as a methodology for monitoring tissue impedance changes during EP-based therapies in real-time. A diagnostic FAST (1-50-1-50+250-10-250-10 µs), aimed towards monitoring inter-burst impedance, demonstrated impedance capture between 1.8 kHz-4.93 MHz at a resolution 216 data points within this frequency range. A therapeutic FAST (2-5-2-100 µs), aimed towards inducing tissue EP while simultaneously monitoring high voltage intra-burst impedance, demonstrated impedance capture between 18.3 kHz-1.96 MHz at a resolution 170 data points within this frequency range. Therapeutic FAST was used to identify a frequency at which EP effects on tissue impedance are minimized, 1.21 MHz in the case of potatoes.

Additional FAST Waveform Considerations

As discussed previously, the impedance data obtained using FAST matches that from a commercial potentiostat, and the FAST method can be used to translate impedance information into a waveform used for H-FIRE treatment. Another embodiment of the invention includes a method to quantity a specific waveform for treatment with known frequency points gathered from the FAST method.

To determine the theoretical plot of the burst scheme, the Unit Step function in Mathematica was used to define a magnitude spectrum around frequencies of interest in combination (FIG. 19A) with a phase of zero. Then, the frequency domain signal inverted using the Inverse Fourier Transform to obtain the desired waveform in the time domain (FIG. 19B). This is the diagnostic waveform that should be applied by a function or pulse generator to obtain data around the frequencies of interest. As a test, the Fourier Transform of the desired waveform was applied to show a return to the original magnitude spectrum (FIG. 19C).

In the example shown in FIG. 19A-C, 10,000 Hz-long square waves have been plotted around frequencies of: 45,000 Hz; 95,000 Hz; 185,000 Hz; 250,000 Hz; 365,000 Hz; 495,000 Hz; 650,000 Hz; 730,000 Hz; 870,000 Hz; 995,000 Hz. Another example is shown in FIG. 20A-C, with a single, 50,000 Hz-long burst from 50,000 Hz to 100,000 Hz. In both of these examples, a variance is applied around the frequencies to account for discrepancies in both voltage and current readings with commercial instruments. As mentioned, in practice, the Fourier Transform of voltage readings would be divided by the Fourier Transform of current readings to get the impedance as a function of frequency. Theoretically, the voltage and current readings should be nearly identical so as to get a consistent impedance result, however, there may be variation. This is what is accounted for in the demonstrated example. FIG. 21A-C illustrates the time domain waveform from FIG. 20A-C at different "zoom" levels. The oscillation of various sine waves that produces the collection of frequencies defined in the initial plot (FIG. 20A) can be seen.

Cycled Pulsing FAST Protocol

In embodiments of the invention, multiple electrodes, e.g., an electrode array, can be used to deliver the electroporation pulses and/or the diagnostic FAST pulses. With an electrode array, one or more of the electrical pulses can be administered using a "cycled pulsing" protocol. Examples of cycled pulsing protocols are provided in FIG. 22, with the corresponding pulse/protocol parameters provided in Table 2:

TABLE 2

Example Cycled Pulsing Protocol

| Group (#) | P+ | P− | Probe Spacing (cm) | Voltage (V) | V/cm | Pulse Length (µs) | Burst Energized Time (µs) | Total Number of Bursts (#) |
|---|---|---|---|---|---|---|---|---|
| 1 | 1 | 4 | 1.7 | 3400 | 2000 | 2 | 60 | 100 |
| 1 | 2 | 3 | 1.7 | 3400 | 2000 | 2 | 60 | 100 |
| 2 | 1 | 2 | 1.4 | 2800 | 2000 | 2 | 60 | 100 |
| 2 | 3 | 4 | 1.4 | 2800 | 2000 | 2 | 60 | 100 |
| 3 | 1 | 3 | 1 | 2000 | 2000 | 2 | 60 | 100 |
| 3 | 2 | 4 | 1 | 2000 | 2000 | 2 | 60 | 100 |

Although protocols with an array of four probes are illustrated, any number of electrodes can be used, including a single probe comprising any number of electrodes and/or multiple electrodes arranged in an electrode array, such as 2, 3, 4, 5, 6, 7, 8, 9, or 10 electrodes and so on. In a "cycled pulsing" protocol, active pairs of electrodes are alternated until a total number of desired pulses have been applied. In these examples, a select number of H-FIRE pulses are administered. For example, electrodes 1 and 4 (Table 2, Group 1—see FIG. 22 for labels) are used to administer a desired number of H-FIRE bursts, here 20 bursts. Following delivery of the H-FIRE pulses/bursts (or other electroporation treatment), another set of probes/electrodes, such as electrodes 2 and 3, are used to deliver another desired number of H-FIRE bursts/pulses. In embodiments, the number of pulses/bursts can be any number and the number of pulses/bursts can be the same or different for each set of pulses/bursts. Indeed, any of the parameters can be adjusted to meet particular goals/needs, including electrode spacing or arrangement, magnitude of voltage, number of electrodes and/or probes, etc. After administration of the H-FIRE/electroporation pulses/bursts, diagnostic FAST pulses can be administered. Typically, in transitioning from H-FIRE pulses/bursts to diagnostic FAST, if using a single generator to administer both HV and LV pulses the voltage is stepped down to a lower voltage, or separate HV and LV generators can be used to administer high-voltage and low-voltage pulses, respectively. In embodiments, the low-voltage diagnostic FAST can be applied either by performing a voltage step-down with the high-voltage generator, where the high-voltage is reduced to a voltage 0-100V, or by integrating a separate low-voltage pulse generator. This sequence of administration of electroporation delivery, followed by diagnostic FAST delivery is repeated until a desired number of therapeutic electrical pulses have been delivered for the treatment. Other possible patterns/protocols for delivery of the electrical pulses are possible, with a couple additional examples provided in Table 2/FIG. 22. The grouping of electrodes described in Table 2/FIG. 22 is intended as an example only. Cycled pulsing protocols can proceed with any electrode configuration/arrangement and/or by activating electrode pairs in any order.

Example Scenarios for Clinical Implementation of FAST

EXAMPLE 1

This treatment constitutes an IRE treatment using a pair (2) of needle electrodes placed into the desired target tissue (tumor). The applied voltage, electrode spacing, and electrode exposure are defined by the clinician. The pulse width is also defined by the clinician. The number of pulses to be applied and duration of treatment is dictated by the FAST technique.

A clinician will insert the IRE electrodes into the tumor tissue. The clinician will initiate the pulse generator software and a low-voltage diagnostic FAST will be automatically implemented to acquire a baseline impedance spectrum of the patient. A high-frequency reference, ~10 MHz, will serve to quantify the clinical endpoint and will be stored in the pulse generator software.

High-voltage pulsing will commence. A series of pulses will be applied, where diagnostic FAST is interlaced in between each high voltage pulse. The pulse generator is pre-programmed with a halting criterion defining an increase in 5° C. at the electrode-tissue interface as measured using a fiber optic temperature sensor. Pulsing will continue until either the halting criteria is met, or the clinical endpoint is reached.

Clinical Endpoint:

The software continually verifies if the clinical endpoint criteria is met:

The low-frequency impedance measurement, ~5 kHz, falls within 10% of the reference high-frequency impedance measurement.

The change in low-frequency impedance, $Z_{i-1}-Z_i$ (where i is the last pulse delivered and i−1 is the pulse prior to that) referenced to the impedance $Z_{i-1}[(Z_{i-1}-Z_i)/Z_{i-1}*100\%]$ falls within 5%.

Halting Criteria:

The software halts pulsing for a preprogrammed time such as 10 s to allow for heat dissipation. Following this delay, pulsing will commence.

Pulsing continues intermittently in this way, until one of the two clinical endpoints is met.

Once the clinical endpoint is met, a final diagnostic FAST is delivered to measure the end state of tissue impedance.

EXAMPLE 2

This treatment constitutes an IRE treatment using a pair (2) of needle electrodes placed into the desired target tissue (tumor). The applied voltage, electrode spacing, and electrode exposure are defined by the clinician. The pulse width is also defined by the clinician. The number of pulses to be applied and duration of treatment is dictated by the FAST technique.

A clinician will insert the IRE electrodes into the tumor tissue. The clinician will initiate the pulse generator software and a low-voltage diagnostic FAST will be automatically implemented to acquire a baseline impedance spectrum of the patient. A high-frequency reference, ~10 MHz, will serve to quantify the clinical endpoint and will be stored in the pulse generator software.

High-voltage pulsing will commence. A series of pulses will be applied, where diagnostic FAST is interlaced in between each high voltage pulse. The pulse generator is pre-programmed with a halting criterion defining application of 25 pulses prior to halting, followed by a 20 seconds delay to allow for heat dissipation. This method of pulsing will continue until the clinical endpoint is reached.

Clinical Endpoint:

The software continually verifies if the clinical endpoint criteria is met:

The low-frequency impedance measurement, ~5 kHz, falls within 10% of the reference high-frequency impedance measurement.

The change in low-frequency impedance, $Z_{i-1}-Z_i$ (where i is the last pulse delivered and i−1 is the pulse prior to that) referenced to the impedance $Z_{i-1}[(Z_{i-1}-Z_i)/Z_{i-1}*100\%]$ falls within 5%.

Pulsing continues intermittently in this way, until one of the two clinical endpoints is met.

Once the clinical endpoint is met, a final diagnostic FAST is delivered to measure the end state of tissue impedance.

The diagnostic FAST pulses can be applied at any time, for example, before, during and/or after any of the electroporation pulses are delivered. Preferably, diagnostic FAST is used in between and/or following any part of the electroporation treatment, such as between individual pulses and/or between bursts of pulses. Diagnostic FAST can also be administered between a single electrode pair or between several electrode pairs.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method for monitoring administration of electrical pulses comprising:
administering a plurality of electrical pulses to a material or a tissue;
obtaining a reference impedance measurement or spectrum relating to the material or tissue;
identifying any change in impedance relative to the reference impedance measurement or spectrum by measuring inter-burst and intra-burst impedance; and monitoring the administering to determine if a desired endpoint is reached as indicated by the change in impedance, and i) adjusting one or more parameters of, ii) stopping, iii) halting, and/or iv) continuing the administering based on the monitoring.

2. The method of claim 1, wherein the desired endpoint is a point during the administering where the administering of the electrical pulses no longer contributes to any change in impedance.

3. The method of claim 1, wherein the reference impedance measurement is:
a prior low-frequency impedance measurement or spectrum; or
a reference high-frequency impedance measurement or spectrum.

4. The method of claim 3, wherein the desired endpoint is a point where the impedance measurement or spectrum decreases to a value within:
20% of the reference high-frequency impedance measurement or spectrum; or
0-10% of the prior low-frequency impedance measurement or spectrum.

5. The method of claim 3, wherein the administering comprises applying one or more low-voltage pulses interleaved between one or more high-voltage pulses.

6. The method of claim 1, further comprising halting the administering to allow tissue temperature to reach a desired level or to allow for a selected amount of time to pass, then resuming the administering to the desired endpoint.

7. The method of claim 1, wherein:
delivering a low-voltage, wideband signal of electrical pulses; and
the monitoring comprises monitoring inter-burst, intra-burst, intra-pulse, and/or inter-pulse impedance by capturing voltage and current and performing discrete Fourier transform analysis.

8. The method of claim 7, wherein the signal comprises a waveform with any step, square, sinusoidal, ramp, Gaussian, or sinc function having constant, increasing, or decreasing frequency, or any arbitrary signal designed to achieve a desired frequency spectrum in the range of above 0.1 kHz to 100 MHz.

9. The method of claim 7, wherein the delivering comprises applying pulses in the range of 0.1 µs to 10 ms.

10. The method of claim 7, wherein the delivering comprises administering the electrical pulses using a cycled pulsing protocol whereby pairs of electrodes are activated according to a selected sequence until a desired number of electrical pulses is delivered.

11. The method of claim 1, wherein:
the administering comprises delivering one or more high-voltage bursts of pulsed electric fields; and
the monitoring comprises monitoring tissue response through monitoring high-voltage inter-pulse, intra-pulse, intra-burst, and/or inter-burst impedance by capturing voltage and current and performing discrete Fourier transform analysis.

12. The method of claim 1, wherein the reference impedance measurement or spectrum and/or measured impedance is obtained by:
reference to an impedance spectrum based on standard impedance values for a particular material or tissue;
measuring impedance of a material or tissue over a selected frequency band;
measuring voltage and/or current and calculating impedance therefrom; and/or
calculating impedance as a function of frequency using the formula:

$$Z(f) = \frac{V(f)}{I(f)},$$

wherein: Z is impedance; V is voltage; and I is current.

13. The method of claim 1, further comprising using a change in impedance measured at high frequencies to predict temperature change for the administering.

14. The method of claim 1, wherein the change in impedance indicates:
whether irreversible or reversible electroporation of a tissue has, is or will occur;
whether chemical cell death and/or decellularization has, is or will occur;
whether death and/or decellularization has, is or will occur due to a physical disruption;
whether a tissue is healthy or cancerous;
whether a tissue has damage from a stroke and/or traumatic brain injury;
whether cell lysis has, is or will occur as evidenced by flattening of the impedance spectrum with no recovery following pulse cessation;
whether cell necrosis has, is or will occur as evidenced by flattening of the impedance spectrum with minimal recovery following pulse cessation; and/or
whether cell apoptosis has, is or will occur as is evidenced by flattening of the impedance spectrum with moderate recovery following pulse cessation.

15. The method of claim 1, wherein the monitoring comprises:
monitoring tissue decellularization and/or cell death;
monitoring gene-transfection efficiency and uptake;
monitoring thermal and/or non-thermal tissue ablation for cardiac arrythmias; and/or
monitoring cell lysis for immunotherapies.

16. The method of claim 1, wherein the administering comprises a diagnostic pulsing scheme comprising 50-100 cycles of 1-50-1-50 µs pulsing and 1-5 cycles of 250-10-250-10 µs pulsing.

17. The method of claim 1, wherein the administering comprises 10-50 cycles of a pulsing scheme chosen from:
1-5-1--100 µs,
5-5-5--100 µs,
10-5-10--100 µs,
2-1-2--100 µs,
2-10-2--100 µs,
2-100-2--100 µs,
2-5-2--1 µs,
2-5-2--10 µs, or
2-5-2--100 µs.

18. A method for monitoring administration of electrical pulses comprising:
administering high-voltage bursts of electrical pulses to a material or a tissue using a high-frequency irreversible electroporation burst scheme;
obtaining a reference impedance measurement or spectrum relating to the material or tissue;
identifying any change in impedance, at a frequency in the range of 18.3 kHz to 2 MHZ, relative to the reference impedance measurement or spectrum;
monitoring tissue response to the administering by monitoring high-voltage inter-pulse, intra-pulse, intra-burst, and/or inter-burst impedance by capturing voltage and current and performing discrete Fourier transform analysis to determine if a desired endpoint is reached as indicated by the change in impedance; and adjusting one or more parameters of, stopping, halting, and/or continuing the administering based on the monitoring;

wherein the high-frequency irreversible electroporation burst scheme comprises pulse widths and intra-phase delays ranging from 0.1 µs to 10 ms and inter-pulse delays ranging from 0.1 µs to 1 s.

* * * * *